United States Patent
Weiman et al.

(10) Patent No.: US 11,491,020 B2
(45) Date of Patent: Nov. 8, 2022

(54) ARTICULATING AND EXPANDABLE INTERBODY FUSIONS DEVICES

(71) Applicant: GLOBUS MEDICAL, INC., Audubon, PA (US)

(72) Inventors: Mark Weiman, Downingtown, PA (US); Myles Sullivan, Philadelphia, PA (US); Tyler Hessler, Phoenixville, PA (US); Chad Glerum, Pennsburg, PA (US); Albert Hill, Richboro, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 16/924,423

(22) Filed: Jul. 9, 2020

(65) Prior Publication Data
US 2022/0008213 A1  Jan. 13, 2022

(51) Int. Cl.
*A61F 2/44* (2006.01)
*A61F 2/46* (2006.01)
*A61F 2/30* (2006.01)

(52) U.S. Cl.
CPC .......... *A61F 2/4425* (2013.01); *A61F 2/4657* (2013.01); *A61F 2/447* (2013.01); *A61F 2002/30131* (2013.01); *A61F 2002/30317* (2013.01); *A61F 2002/30327* (2013.01); *A61F 2002/30405* (2013.01); *A61F 2002/30471* (2013.01); *A61F 2002/30579* (2013.01); *A61F 2002/443* (2013.01); *A61F 2002/4415* (2013.01); *A61F 2002/4666* (2013.01)

(58) Field of Classification Search
CPC ........ A61F 2/44; A61F 2/4425; A61F 2/4455; A61F 2002/443; A61F 2002/448; A61F 2002/4485; A61F 2002/4415
See application file for complete search history.

(56) References Cited

U.S. PATENT DOCUMENTS

| | | | |
|---|---|---|---|
| 4,349,921 A | 9/1982 | Kuntz |
| 4,599,086 A | 7/1986 | Doty |
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |

(Continued)

FOREIGN PATENT DOCUMENTS

| | | |
|---|---|---|
| CA | 2088066 A1 | 1/1992 |
| DE | 4012622 C1 | 7/1991 |

(Continued)

*Primary Examiner* — Anu Ramana

(57) ABSTRACT

Expandable fusion devices, systems, and methods thereof. The expandable implant may include first and second lateral legs and link plates pivotably joined between them. The lateral legs may include upper and lower endplates configured to engage adjacent vertebrae, an actuator assembly including a rotatable actuator having a shaft and a rotatable nut, and driving ramps positioned along the shaft of the actuator. The actuator assembly may cause independent movement of one or more of the driving ramps, thereby causing an expansion in height of the upper and lower endplates of the lateral legs and passive expansion of the connected link plates.

14 Claims, 45 Drawing Sheets

(56) References Cited

U.S. PATENT DOCUMENTS

| | | |
|---|---|---|
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochschuler et al. |
| 6,080,193 A | 6/2000 | Hochshuler |
| 6,099,531 A | 8/2000 | Bonutti |
| 6,126,689 A | 10/2000 | Brett |
| 6,176,882 B1 | 1/2001 | Biedermann |
| 6,258,125 B1 | 7/2001 | Paul et al. |
| 6,558,423 B1 | 5/2003 | Michelson |
| 6,562,074 B2 | 5/2003 | Gerbec et al. |
| 6,576,016 B1 | 6/2003 | Hochshuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 7,985,256 B2 | 7/2011 | Grotz et al. |
| 8,062,375 B2 | 11/2011 | Glerum |
| 8,070,813 B2 | 12/2011 | Grotz et al. |
| 8,123,810 B2 | 2/2012 | Gordon |
| 8,137,405 B2 | 3/2012 | Kostuik |
| 8,192,495 B2 | 6/2012 | Simpson et al. |
| 8,303,663 B2 | 11/2012 | Jimenez et al. |
| 8,377,140 B2 | 2/2013 | DeFalco et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | Jimenez et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,358,125 B2 | 6/2016 | Jimenez et al. |
| 9,532,883 B2 | 1/2017 | McLuen et al. |
| 9,622,878 B2 | 4/2017 | Grotz |
| 2002/0045945 A1 | 4/2002 | Liu |
| 2002/0068976 A1 | 6/2002 | Jackson |
| 2002/0068977 A1 | 6/2002 | Jackson |
| 2004/0030387 A1 | 2/2004 | Landry |
| 2004/0049271 A1 | 3/2004 | Biedermann |
| 2004/0054412 A1 | 3/2004 | Gerbec et al. |
| 2004/0087947 A1 | 5/2004 | Lim et al. |
| 2004/0153065 A1 | 8/2004 | Lim |
| 2005/0021041 A1 | 1/2005 | Michelson |
| 2005/0021145 A1 | 1/2005 | de Villiers |
| 2005/0033432 A1 | 2/2005 | Gordon |
| 2005/0080422 A1 | 4/2005 | Otte |
| 2005/0113916 A1 | 5/2005 | Branch, Jr. |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0015184 A1 | 1/2006 | Winterbottom |
| 2006/0058878 A1 | 3/2006 | Michelson |
| 2006/0084986 A1 | 4/2006 | Grinberg |
| 2006/0122701 A1 | 6/2006 | Kister |
| 2006/0129244 A1 | 6/2006 | Ensign |
| 2006/0142859 A1 | 6/2006 | McLuen |
| 2006/0149385 A1 | 7/2006 | McKay |
| 2006/0195192 A1 | 8/2006 | Gordon et al. |
| 2006/0229729 A1 | 10/2006 | Gordon |
| 2006/0241770 A1 | 10/2006 | Rhoda |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote |
| 2008/0140207 A1 | 6/2008 | Olmos |
| 2008/0147194 A1 | 6/2008 | Grotz |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy |
| 2009/0076616 A1 | 3/2009 | Duggal |
| 2009/0125062 A1 | 5/2009 | Arnin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger |
| 2010/0286783 A1 | 11/2010 | Lechmann |

(56) References Cited

U.S. PATENT DOCUMENTS

| | | |
|---|---|---|
| 2011/0035011 A1 | 2/2011 | Cain |
| 2011/0093074 A1 | 4/2011 | Glerum |
| 2011/0160861 A1 | 6/2011 | Jimenez |
| 2011/0172774 A1 | 7/2011 | Varela |
| 2011/0276142 A1 | 11/2011 | Niemiec |
| 2011/0301713 A1 | 12/2011 | Theofilos |
| 2011/0319997 A1 | 12/2011 | Glerum |
| 2012/0035729 A1 | 2/2012 | Glerum |
| 2012/0059470 A1 | 3/2012 | Weiman |
| 2012/0059472 A1 | 3/2012 | Weiman |
| 2012/0109308 A1 | 5/2012 | Lechmann |
| 2012/0130496 A1 | 5/2012 | Duffield |
| 2012/0158140 A1* | 6/2012 | Miller ............... A61F 2/4465 623/17.11 |
| 2012/0165945 A1 | 6/2012 | Hansell |
| 2012/0185049 A1 | 7/2012 | Varela |
| 2012/0209386 A1 | 8/2012 | Triplett |
| 2012/0215313 A1 | 8/2012 | Saidha |
| 2012/0265309 A1 | 10/2012 | Glerum |
| 2012/0277861 A1 | 11/2012 | Steele et al. |
| 2012/0277870 A1 | 11/2012 | Wolters |
| 2012/0323329 A1 | 12/2012 | Jimenez |
| 2012/0330426 A1 | 12/2012 | McLaughlin |
| 2013/0023993 A1 | 1/2013 | Weiman |
| 2013/0023994 A1 | 1/2013 | Glerum |
| 2013/0123924 A1* | 5/2013 | Butler ................ A61F 2/446 623/17.16 |
| 2013/0158669 A1 | 6/2013 | Sungarian |
| 2013/0274883 A1 | 10/2013 | McLuen et al. |
| 2014/0088714 A1 | 3/2014 | Miller et al. |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0166396 A1 | 6/2016 | McClintock |
| 2016/0324654 A1 | 11/2016 | Loebl et al. |
| 2017/0100258 A1 | 4/2017 | Jimenez et al. |
| 2017/0119543 A1 | 5/2017 | Dietzel et al. |
| 2021/0186709 A1* | 6/2021 | Weiman ............ A61F 2/4611 |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| FR | 2794968 | 12/2000 |
| JP | 2000-513263 | 10/2000 |
| SU | 1424826 A1 | 9/1988 |
| WO | 9201428 A1 | 2/1992 |
| WO | 9525485 A1 | 9/1995 |
| WO | 199942062 A1 | 8/1999 |
| WO | 199966867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2012031267 A1 | 3/2012 |

* cited by examiner

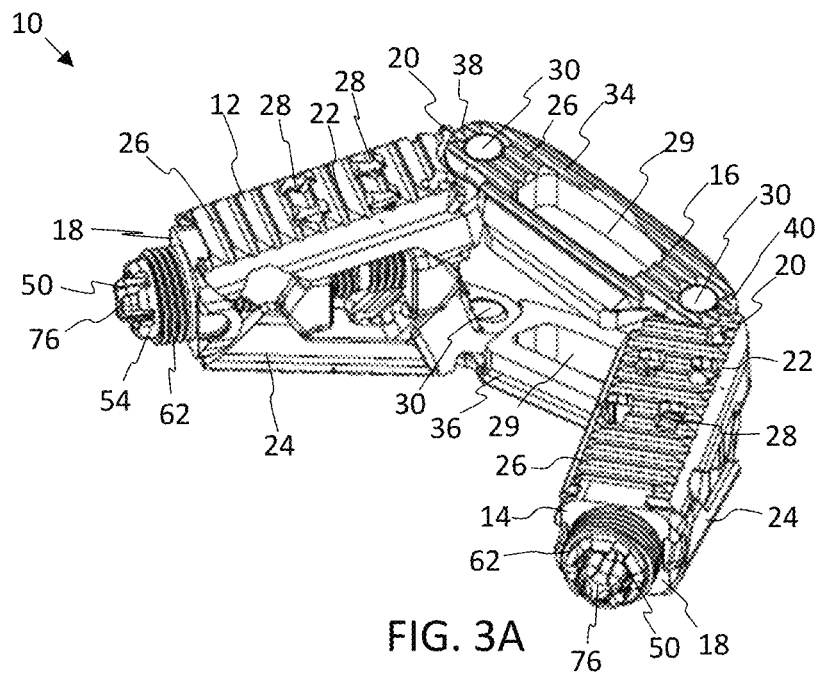
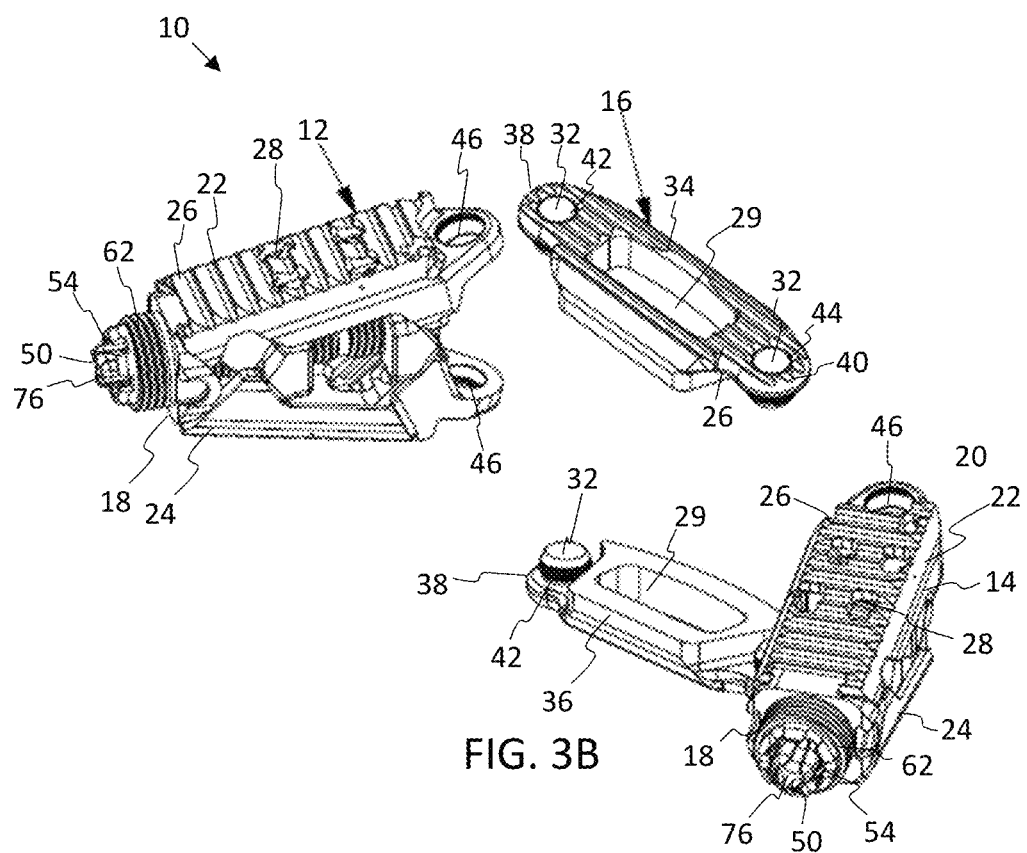

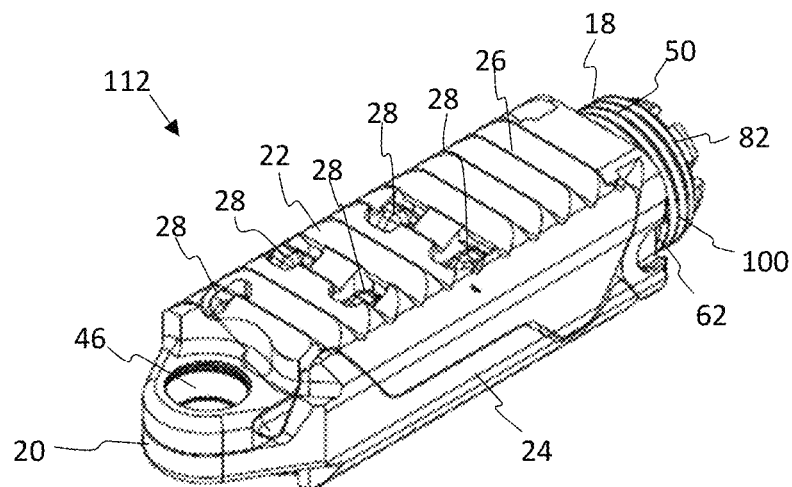
FIG. 11A
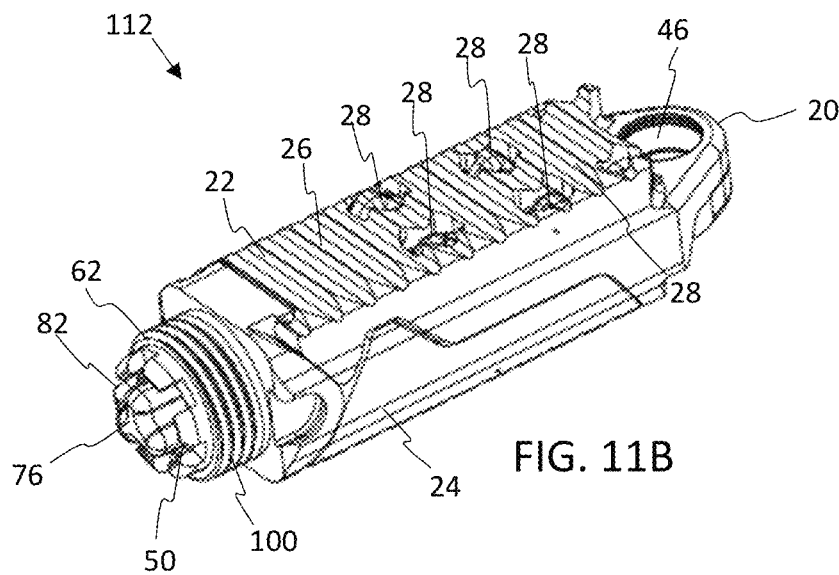
FIG. 11B
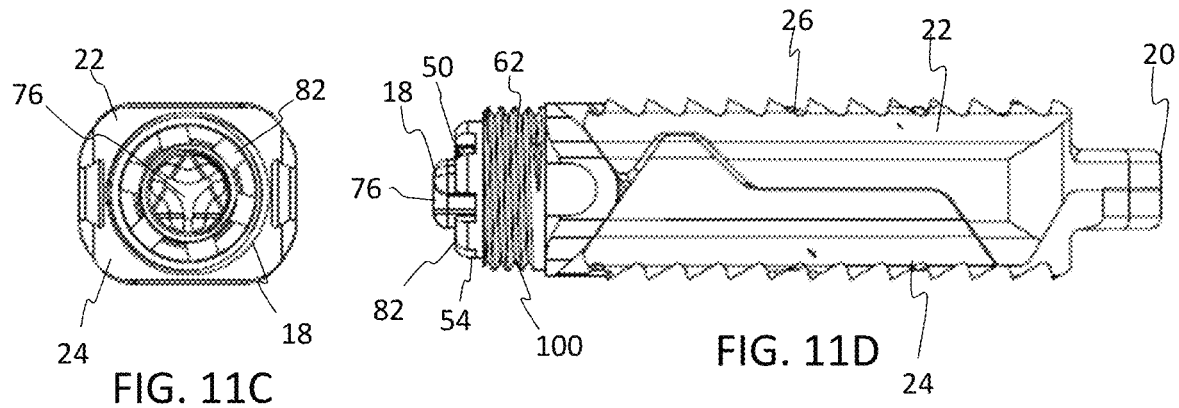
FIG. 11C
FIG. 11D

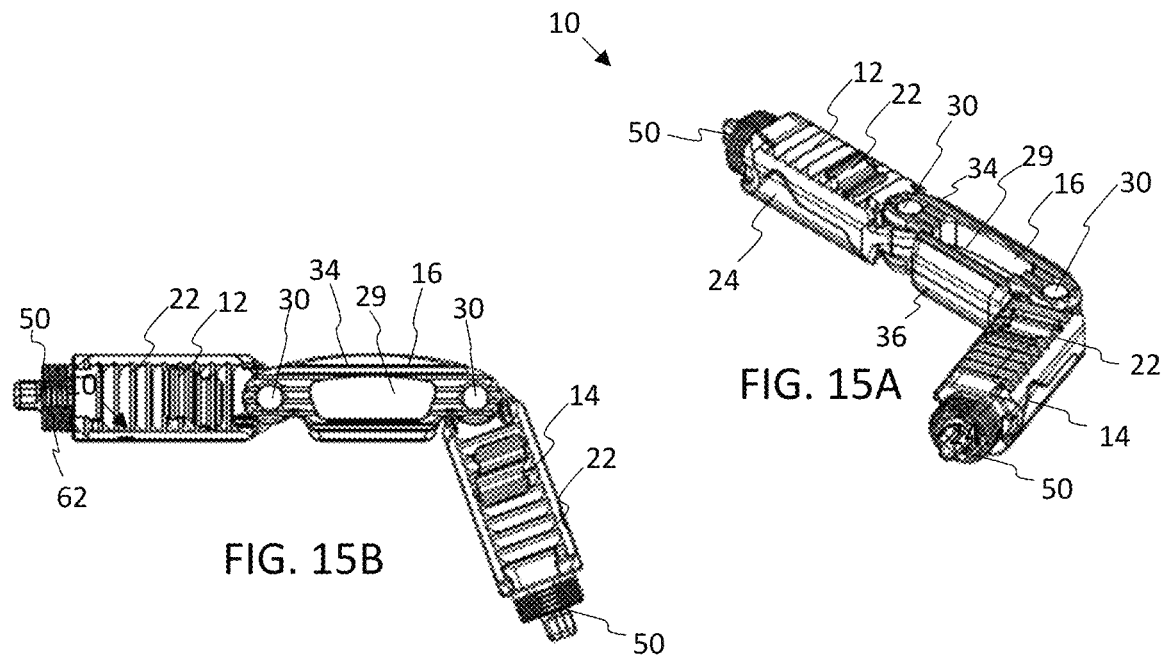
FIG. 15A
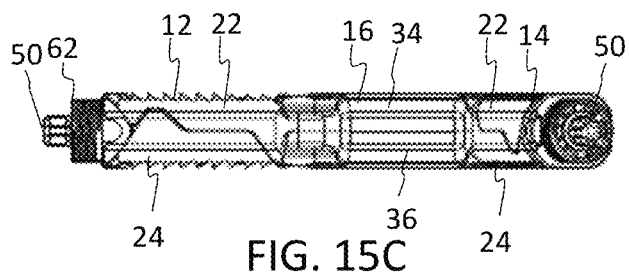
FIG. 15B
FIG. 15C
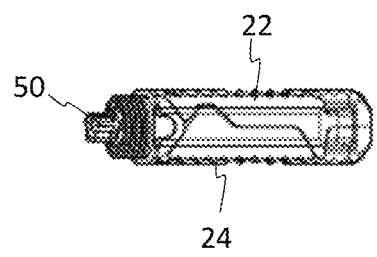
FIG. 15D
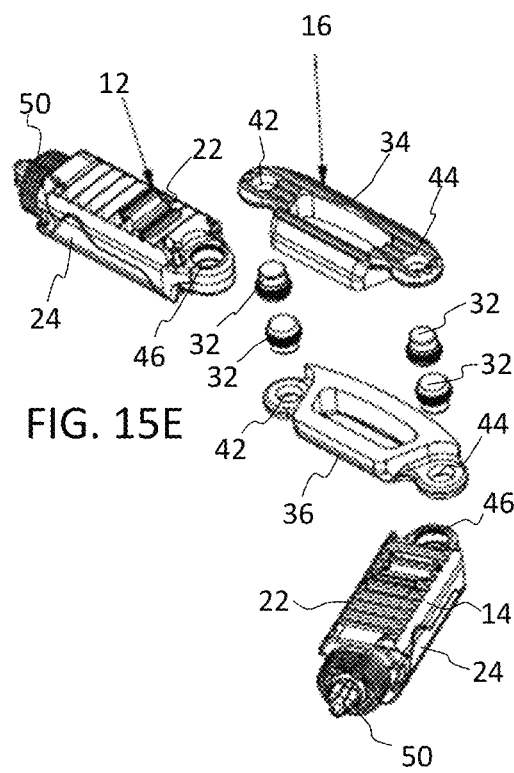
FIG. 15E

A-A

C-C

ARTICULATING AND EXPANDABLE INTERBODY FUSIONS DEVICES

FIELD OF THE INVENTION

The present disclosure relates to surgical devices, and more particularly, to articulating and expandable fusion devices capable of being deployed inside an intervertebral disc space and then expanded to maintain disc spacing, restore spinal stability, and/or facilitate an intervertebral fusion.

BACKGROUND OF THE INVENTION

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc is first partially or fully removed. An intervertebral fusion device is then typically inserted between neighboring vertebrae to maintain normal disc spacing and restore spinal stability, thereby facilitating an intervertebral fusion.

Interbody devices have been used to provide support and stability in the anterior column of the spinal vertebrae when treating a variety of spinal conditions, including degenerative disc disease and spinal stenosis with spondylolisthesis. Clinical treatment of spinal pathologies with anterior vertebral body interbody devices relies on precise placement of the interbody device to restore normal anterior column alignment. Iatrogenic pathologies may result from the surgical access window to the disc space, failure to precisely place the interbody on hard cortical bone often found on the apophyseal ring of the vertebral body, and/or failure to precisely control and restore normal anatomical spinal alignment.

As such, there exists a need for a fusion device capable of precise placement of interbody support that both increases interbody contact with hard cortical bone and provides precise control of anterior column alignment while reducing the profile of the access window to the disc space.

SUMMARY OF THE INVENTION

To meet this and other needs, and in view of its purposes, the present application provides devices, systems, and methods for installing, articulating, and expanding the interbody implant. In particular, an expandable fusion device is provided, which has first and second lateral legs and one or more link plates pivotably coupled between the first and second lateral legs. The lateral legs and link plates may be aligned to form a linear orientation, and the lateral legs may be pivotable relative to the link plates to form a widened U-shaped orientation for the implant. The lateral legs and attached link plates may be expanded to adjust lordosis and/or coronal balance. The device may be installed in an open, semi-open, or minimally invasive surgical procedure. The expandable fusion device may be capable of being placed into the disc space, for example, down a guide tube or cannula and then expanded in height into an expanded configuration.

According to one embodiment, an expandable implant includes first and second lateral legs and a link plate joined to each of the first and second lateral legs by a hinge. The first and second lateral legs each include upper and lower endplates configured to engage adjacent vertebrae, an actuator assembly including a rotatable actuator having a shaft and a rotatable nut, and a plurality of driving ramps including a front ramp, a mid-ramp, and a rear ramp positioned along the shaft of the actuator. The upper and lower endplates may be engaged with the plurality of driving ramps. Rotation of the actuator and/or the nut may cause movement of one or more of the driving ramps, thereby causing an expansion in height of the upper and lower endplates. The first and second lateral legs and link plate may be positionable along a central longitudinal axis of the implant, thereby forming a linear orientation configured to be inserted through a cannula. The first and second lateral legs may be pivotable about the respective hinges, thereby allowing for a widened U-shaped configuration of the implant.

The implant may include a first or upper link plate and a second or lower link plate. The first link plate may be hingedly connected to the upper endplates of the first and second lateral legs, and the second link plate may be hingedly connected to the lower endplates of the first and second lateral legs. The first and second link plates may be passively expanded when either or both of the first and second lateral legs are actively expanded.

The rotatable nut may be configured to move the rear ramp independent of the mid-ramp and the front ramp. In one embodiment, the shaft of the actuator may include a first threaded portion, a second threaded portion, and a third threaded portion. The front ramp may be positioned on and moveable along the first threaded portion of the actuator. The mid-ramp may be positioned on and moveable along the second threaded portion of the actuator. The rear ramp may be positioned on and moveable along the third threaded portion of the actuator. In another embodiment, the shaft of the actuator includes a first threaded portion, a second threaded portion, and a non-threaded portion. The front ramp may be positioned on the non-threaded portion of the actuator. The mid-ramp may be positioned on and moveable along the first threaded portion of the actuator. The rear ramp may be positioned on and moveable along the second threaded portion of the actuator. The threaded portions may have the same or different attributes including outer diameters, handedness, thread form, thread angle, lead, pitch, etc. In one embodiment, the first threaded portion may have a smaller outer diameter and different handedness than the second threaded portion of the actuator.

According to another embodiment, an expandable implant includes upper and lower link plates each extending from a first end to a second end and first and second lateral legs. The first and second lateral legs may each include upper and lower endplates configured to engage adjacent vertebrae, an actuator assembly including a rotatable actuator having a shaft and a rotatable nut, and a plurality of driving ramps including a front ramp, a mid-ramp, and a rear ramp positioned along the shaft of the actuator. The upper and lower endplates may be engaged with the plurality of driving ramps. Rotation of the actuator and/or the nut may cause movement of one or more of the driving ramps, thereby causing an expansion in height of the upper and lower endplates. The upper link plate may be pivotably coupled to the first lateral leg at the first end of the upper link plate and may be pivotably coupled to the second lateral leg at the second end of the upper link plate. The lower link plate may be pivotably coupled to the first lateral leg at the first end of the lower link plate and may be pivotably coupled to the second lateral leg at the second end of the lower link plate. The upper and lower link plates may be passively expanded when either or both of the first and second lateral legs are expanded.

The first and second lateral legs and upper and lower link plates may be positionable along a central longitudinal axis of the implant, thereby forming a linear orientation configured to be inserted through a cannula. The first and second lateral legs may be pivotable relative to the link plates, thereby allowing for a widened U-shaped configuration of the implant.

According to another embodiment, an expandable implant includes a strain gauge embedded in at least one of the first lateral leg, the second lateral leg, and the link plate. The strain gauge may include a plurality of sensors and a circuitry connecting the plurality of sensors. The strain gauge may measure the force, pressure, tension, and/or weight distribution across the surface area of the implant. A first strain gauge may be embedded in the upper endplate of the first lateral leg. A second strain gauge may be embedded in the upper endplate of the second lateral leg. A third strain gauge may be embedded in the upper link plate. At least one of the strain gauges may have a different circuitry that the other strain gauges. A fourth strain gauge may be embedded in the lower endplate of the first lateral leg. A fifth strain gauge may be embedded in the lower endplate of the second lateral leg. A sixth strain gauge may be embedded in the lower link plate. The first and second lateral legs and the link plates may be 3D printed. The strain gauges may be embedded in each of the first and second lateral legs and the link plates during the 3D printing process to provide a complete integration between the 3D printed material and the strain gauges.

According to yet another embodiment, methods of installing the expandable implants are provided. A disc space of a patient may be accessed and prepared from a posterior approach. A collapsed implant having a linear orientation may be positioned within the disc space via a cannula. The collapsed implant may be articulated into a widened U-shaped configuration. One or both of the lateral legs of the implant may be expanded in height, thereby passively expanding the attached link plates, to provide an expanded configuration for the implant. The cannula may be withdrawn from the patient's body, thereby leaving the implant in the expanded position.

Also provided are kits including expandable fusion devices of varying types and sizes, rods, fasteners or anchors, k-wires, insertion tools, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIGS. 3A-3G show perspective, exploded, top, front, rear, and side views, respectively, of the expandable fusion device of FIGS. 2A-2E with both lateral legs hinged with respect to the link plates and the lateral legs are non-uniformly expanded in height;

FIGS. 11A-11G show perspective, rear, side, top and cross-sectional views, respectively, of the lateral leg shown in FIG. 10 in a fully collapsed configuration;

FIGS. 15A-15E show perspective, top, rear, side, and exploded views of the expandable fusion device in FIGS. 14A-14E with a first lateral leg hinged at an angle with respect to link plates joining the two lateral legs;

DETAILED DESCRIPTION OF THE INVENTION

Figure 1A:
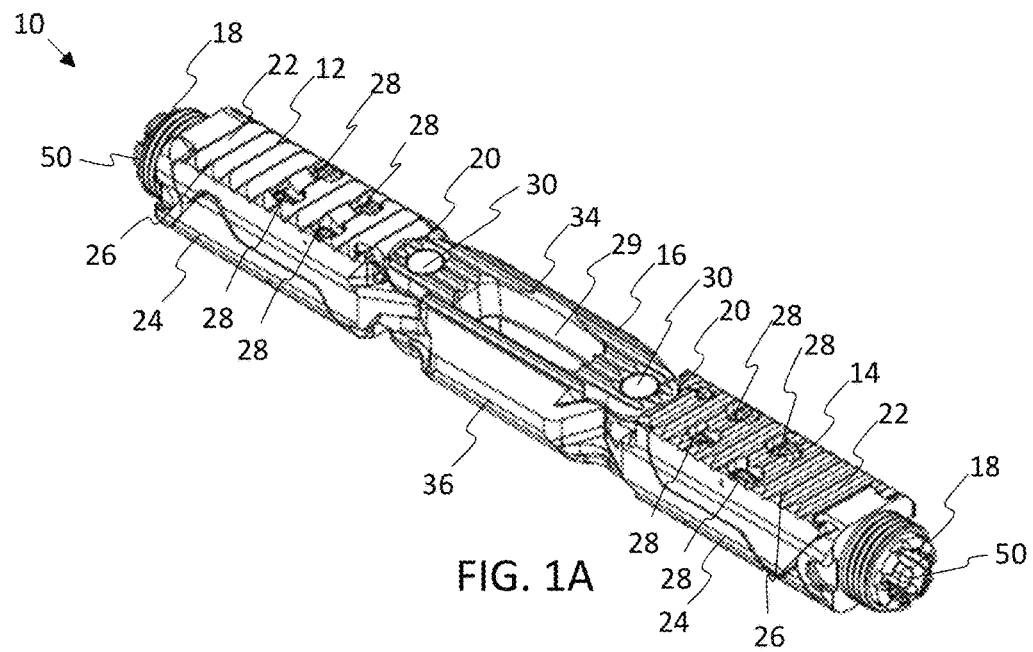
FIGS. 1A-1E are perspective, exploded, top, cross-sectional, and side views, respectively, of an expandable fusion device according to one embodiment, in a fully collapsed and linear orientation configured to be inserted into the body.
Figure 1B:
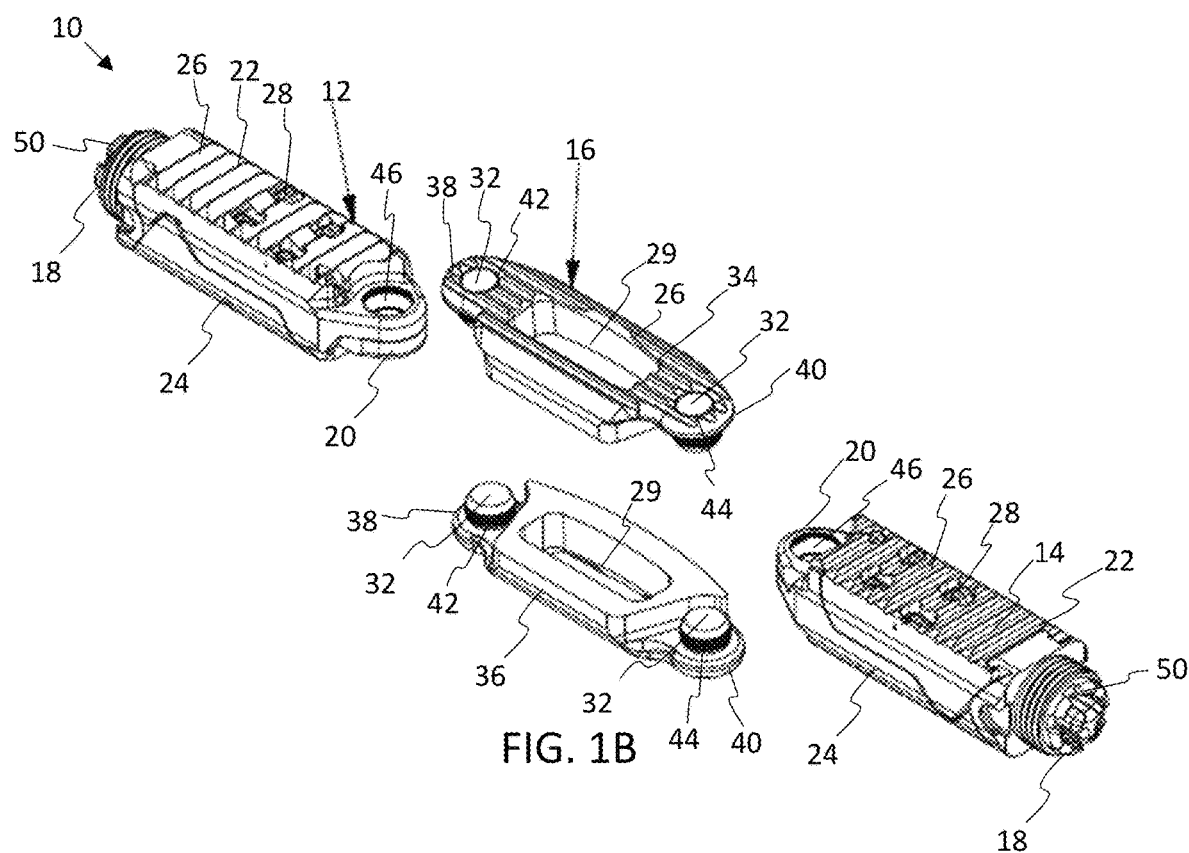
Figure 1C:
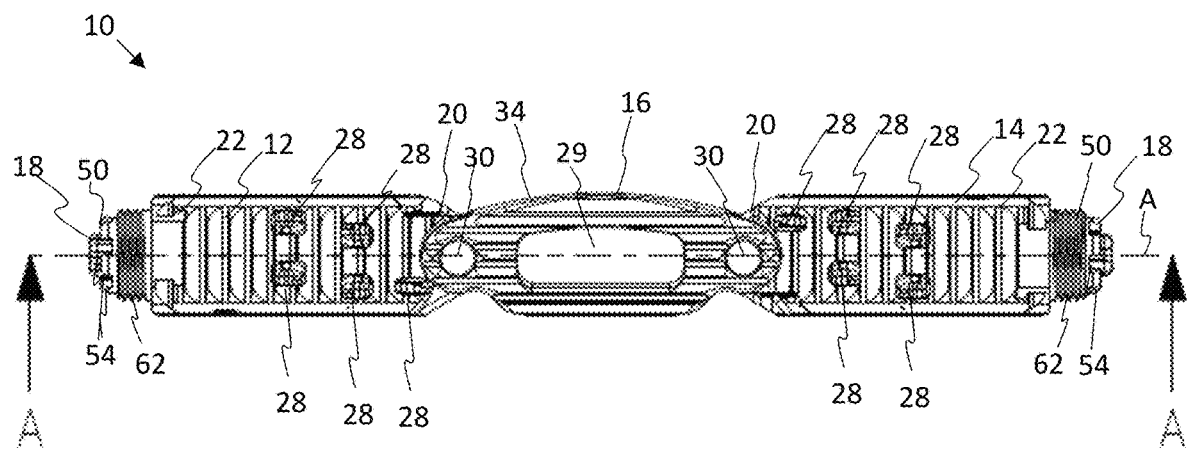
Figure 1D:
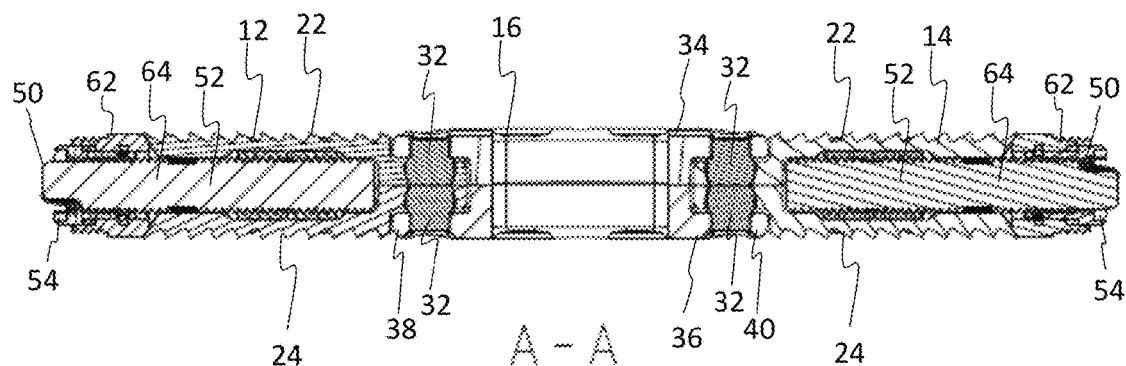
Figure 1E:
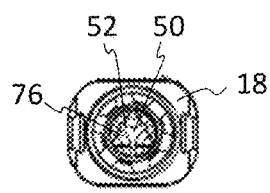
Figure 2A:
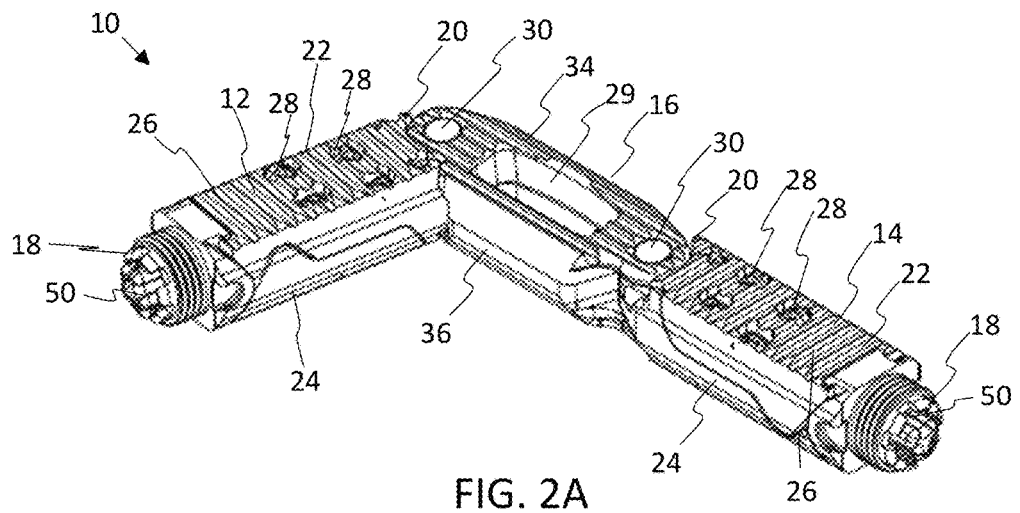
FIGS. 2A-2E show perspective, exploded, top, cross-sectional, and side views, respectively, of the expandable fusion device of FIGS. 1A-1E with a first lateral leg hinged at an angle with respect to link plates joining the two lateral legs.
Figure 2B:
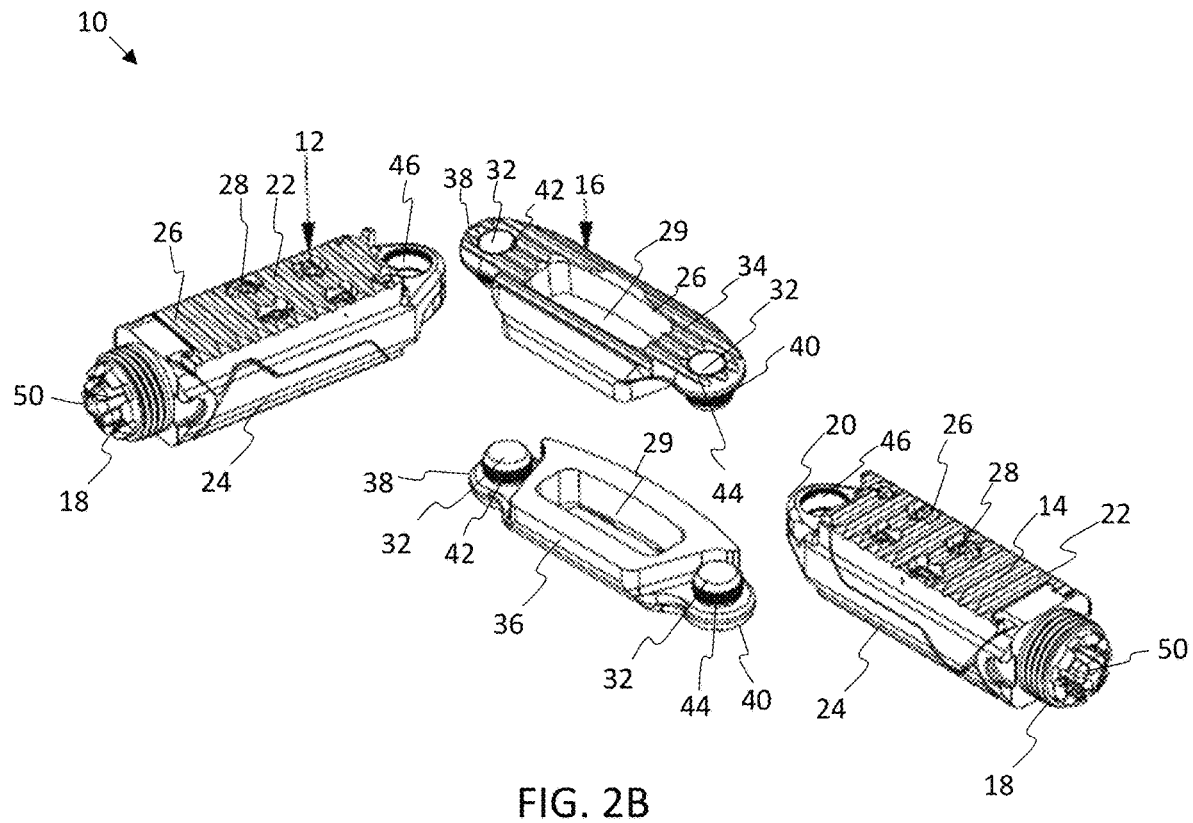
Figure 2C:
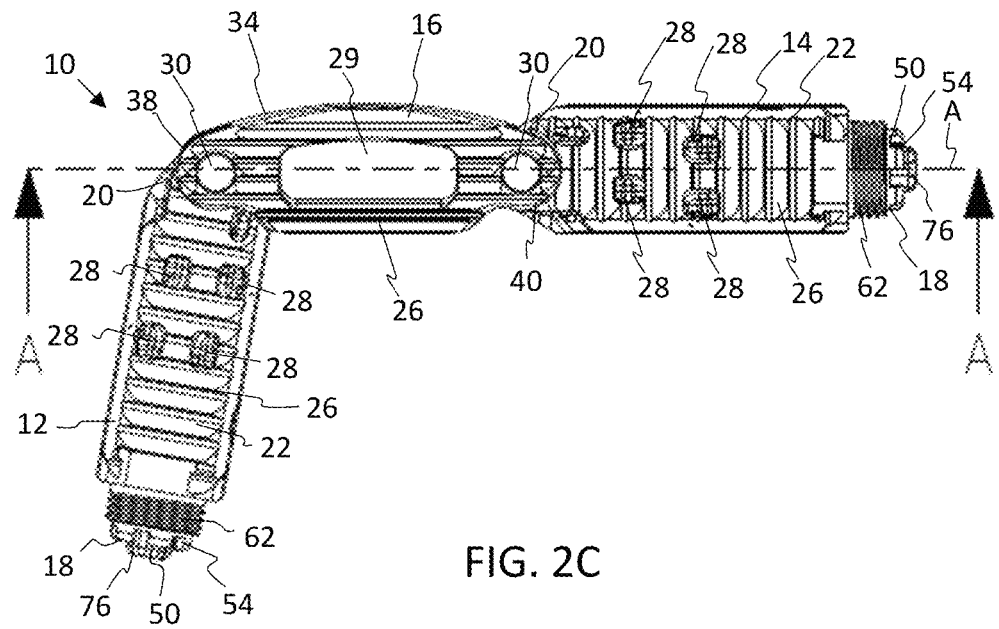
Figure 2D:
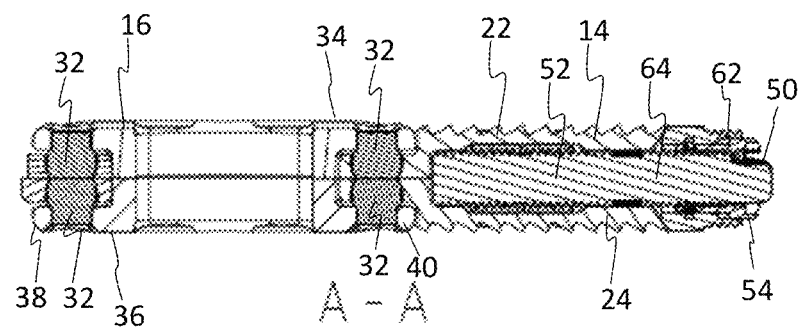
Figure 2E:
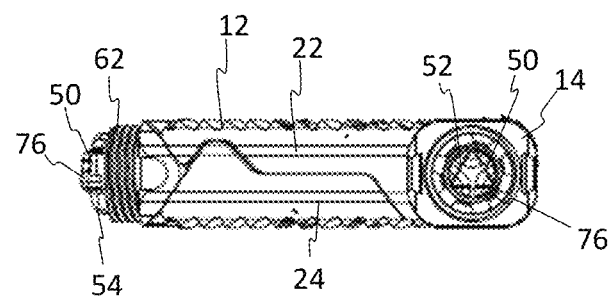
Figure 3C:
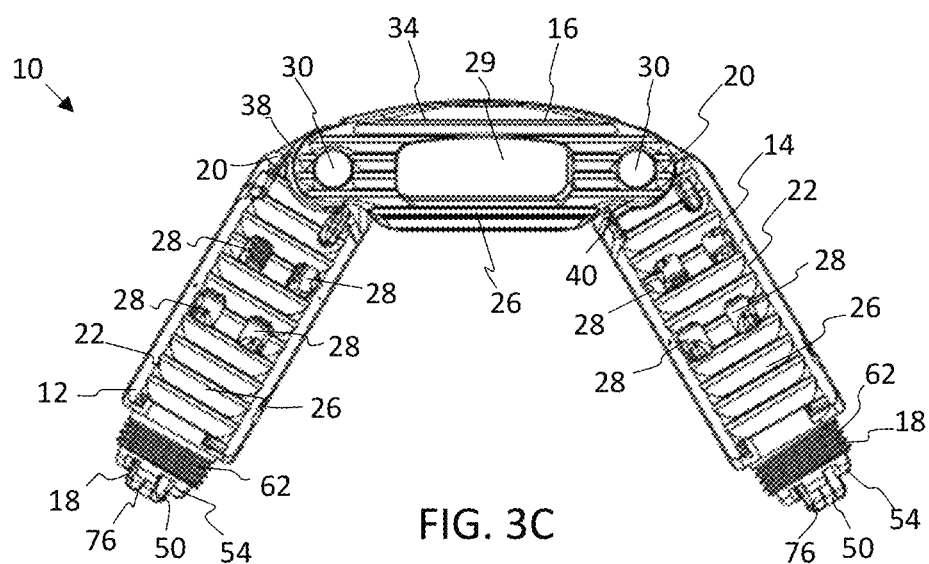
Figure 3D:
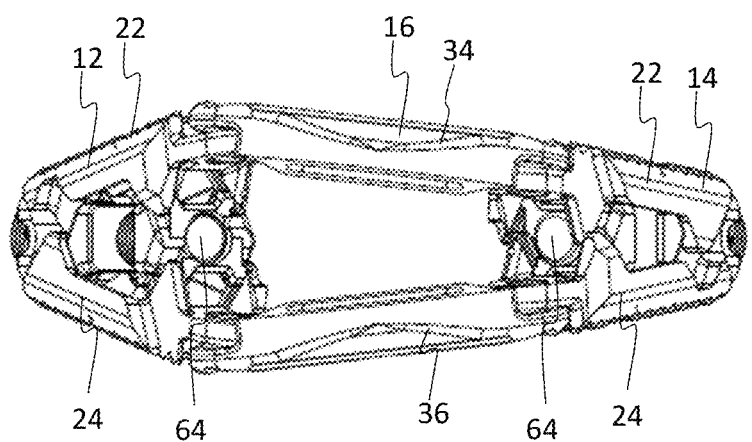
Figure 3E:
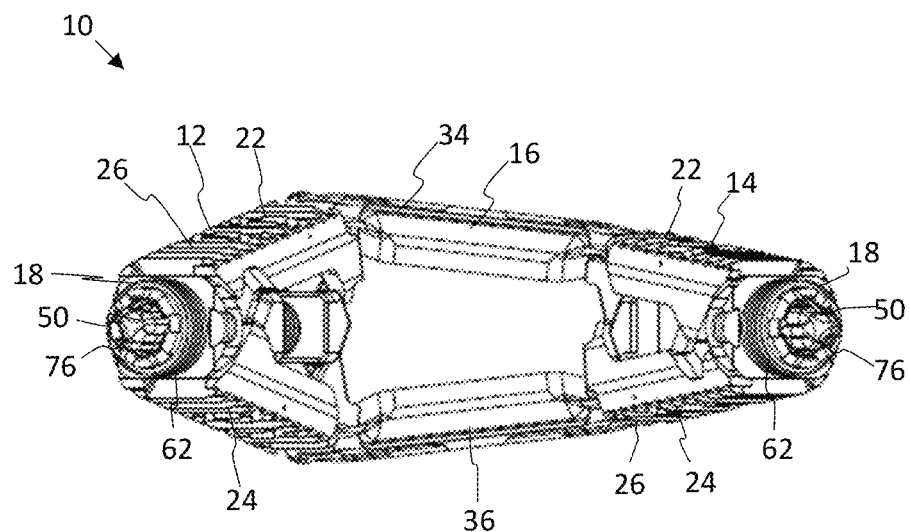
Figure 3F:
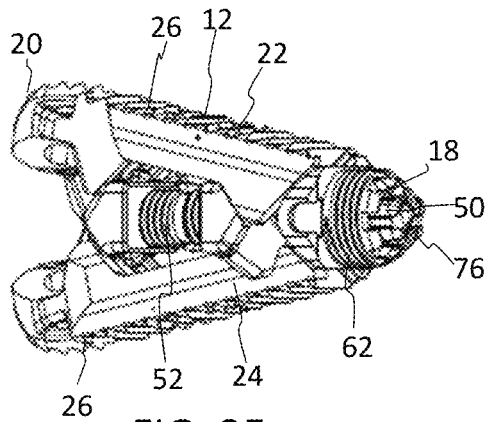
Figure 3G:
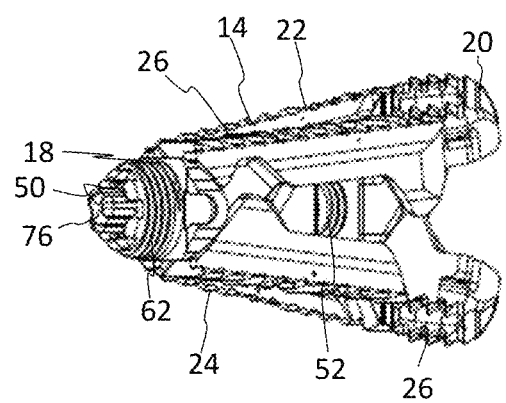
Figure 4A:
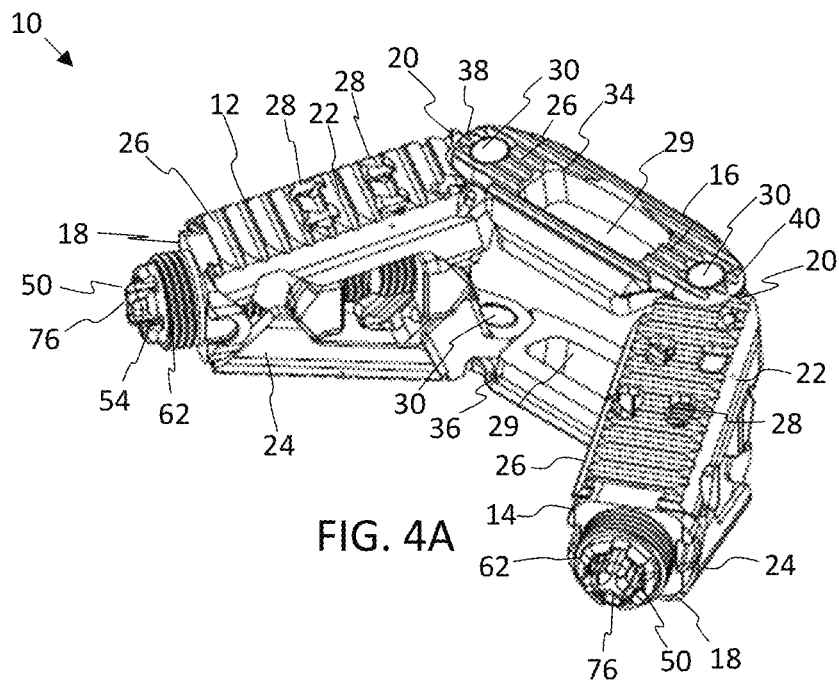
FIGS. 4A-4F show perspective, exploded, top, front, rear, and side views, respectively, of the expandable fusion device of FIGS. 3A-3G uniformly expanded in height.
Figure 4B:
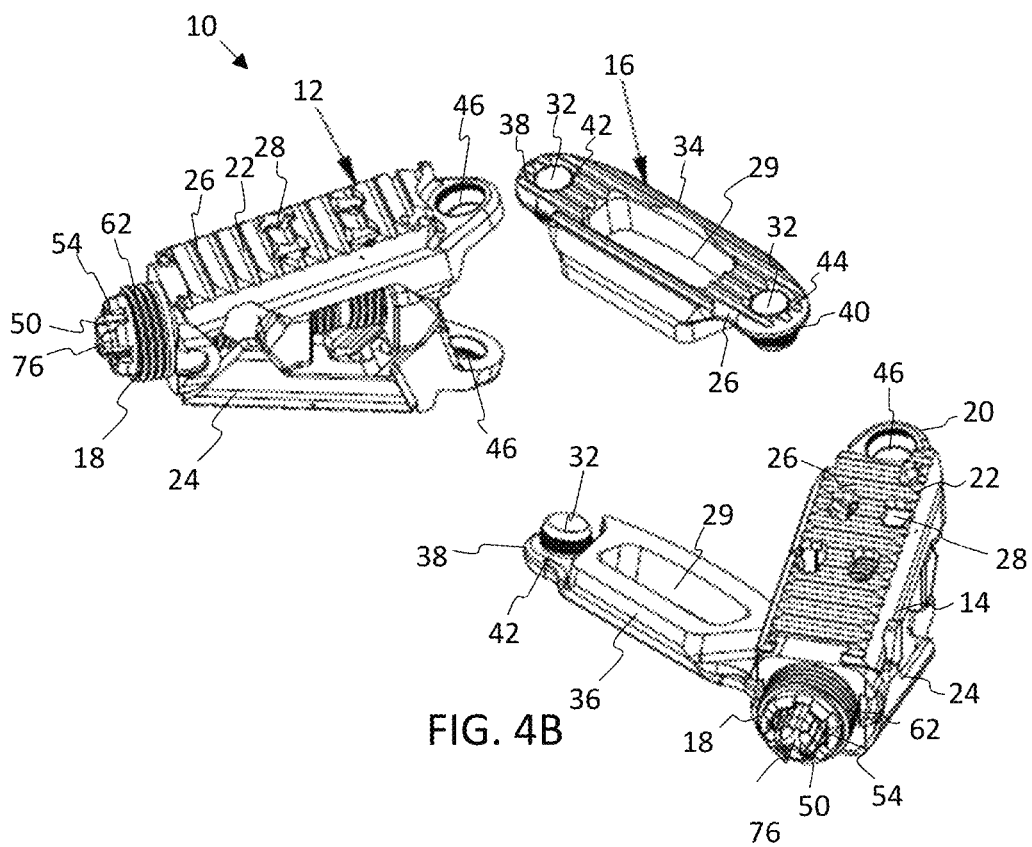
Figure 4C:
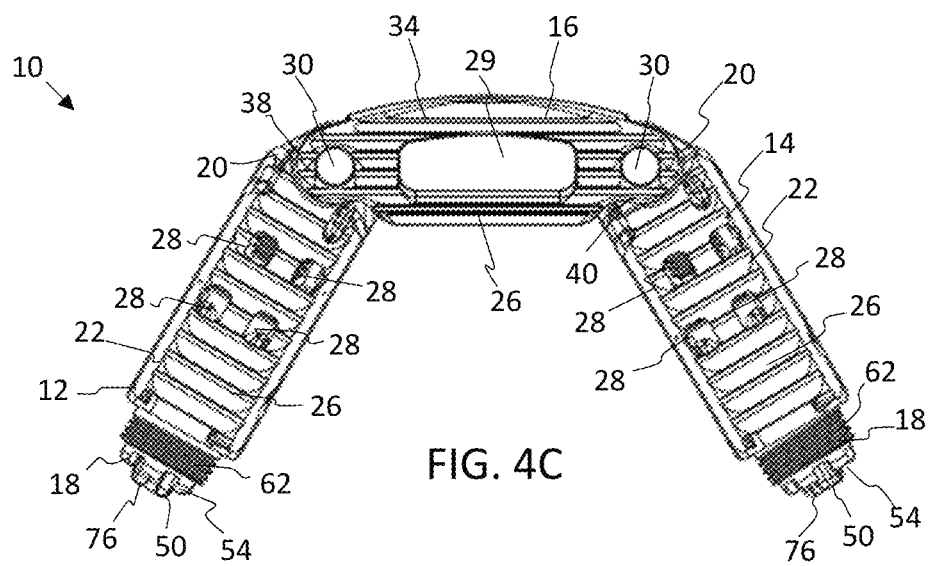
Figure 4D:
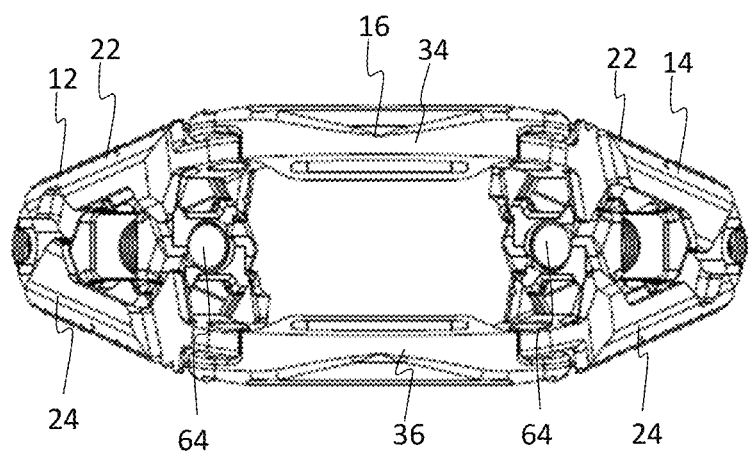
Figure 4E:
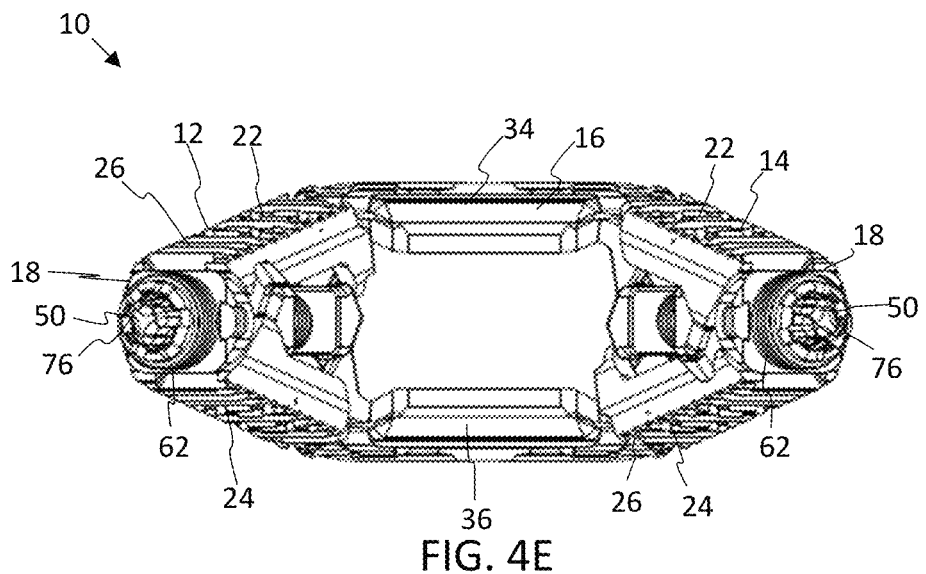
Figure 4F:
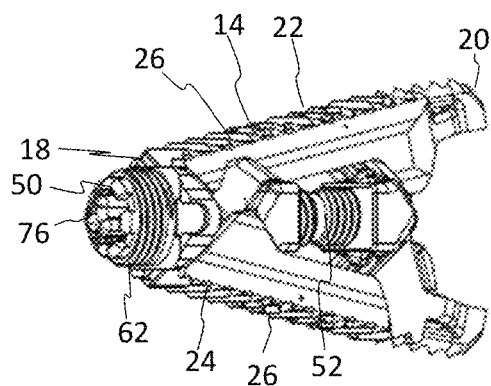
Figure 5A:
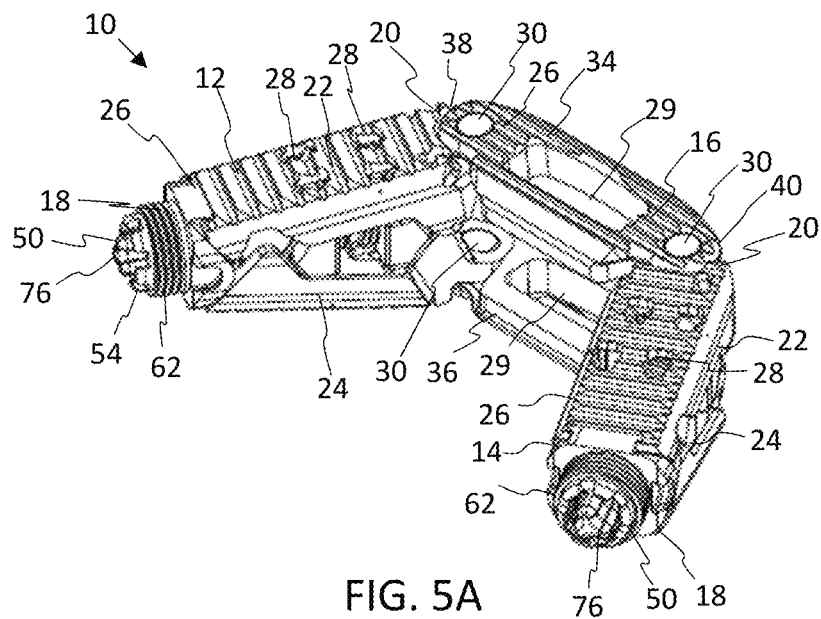
FIGS. 5A-5E show perspective, exploded, top, rear, and side views, respectively, of the expandable fusion device of FIGS. 4A-4F uniformly expanded in height.
Figure 5B:
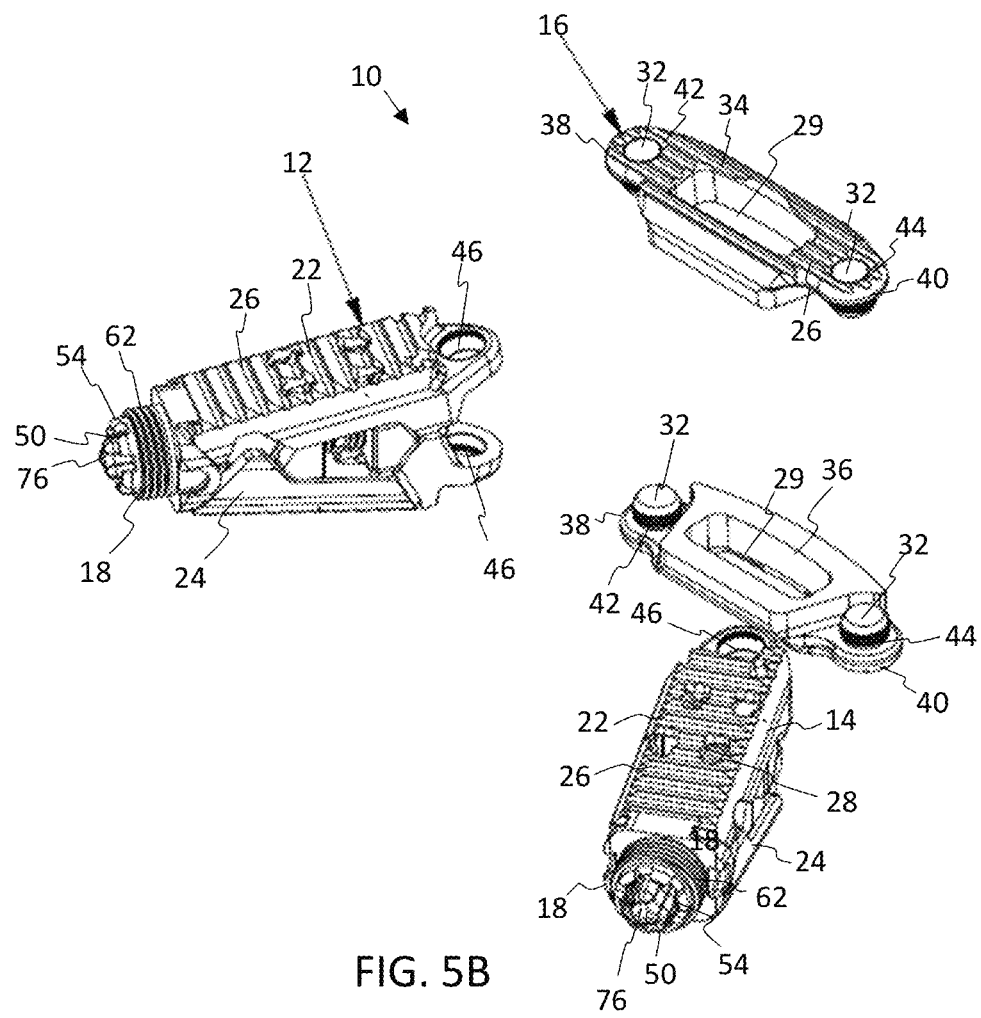
Figure 5C:
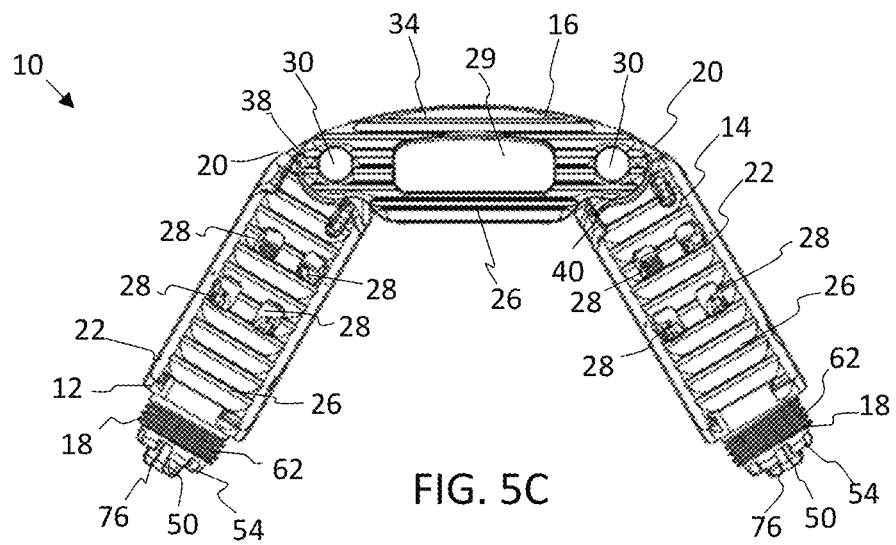
Figure 5D:
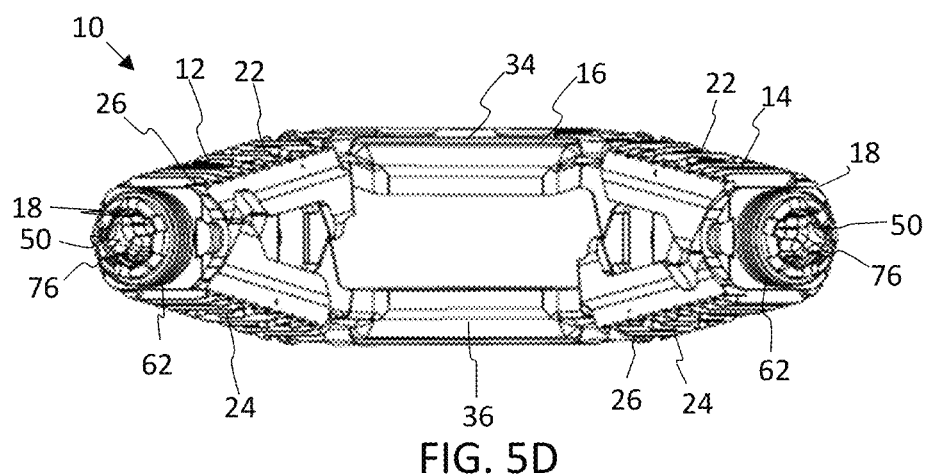
Figure 5E:
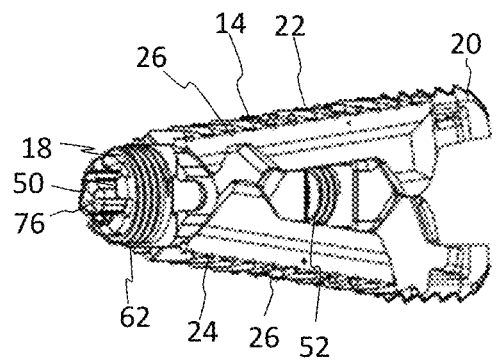

In order to improve the access profile of the interbody while maximizing cortical bone contact surface area, the interbody implant may be positioned within the disc space in a linear configuration, articulated into a widened configuration to increase surface area contact, and expanded in height to restore anatomical spinal alignment. While expanding in height, the respective heights of the lateral legs may be individually adjusted. The anterior side of the implant may be adjusted in height relative to the posterior side, thereby changing the lordotic angle. Expanding one side of the implant differently than the other will also allow for coronal adjustments. Accordingly, embodiments of the present application are generally directed to devices, systems, and methods for installing, articulating, and expanding the interbody implant. The terms implant, interbody, interbody implant, fusion device, spacer, cage, and expandable device may be used interchangeably herein.

Referring now to FIGS. 1A-1E, an articulating expandable fusion device or implant 10 is shown. The implant 10 may include three or more sections or legs, which are configured to articulate or pivot relative to one another to increase the overall width or footprint of the implant 10. The implant 10 may include a first expandable lateral leg 12, a second expandable lateral leg 14, and a third central leg with one or more link plates 16, which connect the first and second lateral legs 12, 14. When the first and/or second lateral legs 12, 14 are independently expanded in the height, the attached link plate or plates 16 are configured to passively increased in height, thereby providing lordotic and/or coronal adjustments.

The expandable lateral legs 12, 14 will be described with reference to the first lateral leg 12. It will be appreciated that the second lateral leg 14 is identical, or a mirror image, of the first lateral leg 12. The lateral leg 12 may extend from a rear end or proximal end 18 to a front end or distal end 20. It will be appreciated that when the legs 12, 14 and link plates 16 are aligned as shown in FIGS. 1A-1E, the front ends 20 of the lateral legs 12, 14 may face toward one another, but when the lateral legs 12, 14 are articulated relative to the link plates 16 as shown in FIGS. 3A-3E, the front ends 20 may face toward the anterior of the spine and the rear ends 18 may face toward the posterior of the spine.

The lateral leg 12, 14 includes a first or upper endplate 22 and a second or lower endplate 24 configured to engage adjacent vertebrae. The lateral leg 12, 14 is connected to one or more link plates 16, and the lateral leg 12, 14 is configured to articulate relative to the link plate 16 about one or more pivot or spherical joints 30. The spherical joint 30 may allow for free rotation in two planes at the same time while preventing translation. The spherical joint 30 may be a revolute joint such as a ball joint, pin joint, or hinge joint.

The lateral legs 12, 14 and link plates 16 may be able to rotate freely about each respective pin 32. The pin 32 may include a cylinder portion, spheroidal portion, oval portion, and/or other curved shape portion. A portion of the pin 32 may be positioned within a portion of endplate 22, 24 and an opposite portion of the pin 32 may be positioned within the link plate 34, 36. A portion of the pin 32 may be affixed to one of the endplate 22, 24 and/or the link plate 34, 36, for example by a press fit, interference fit, adhesive, or other fastening method, and the opposite portion may remain movable with respect to the socket of the other endplate 22, 24 and/or link plate 34, 36. This may enable the endplate 22, 24 to hingedly connect to the link plate 34, 36 and for these hinged elements to be movable with respect to each other along more than one axis. Other hinge types may also be used, such as a living hinge or piano hinge, as nonlimiting examples.

Although spherical joints 30 are exemplified herein, it will be appreciated that other joint geometries may be used. The spherical joints 30 may allow for differential adjustment of the expandable legs 12, 14 during expansion or in the final construct as the surgeon intends. The spherical joints 30 may account for different insertion angles of the legs 12, 14 relative to each other, without locking the implant 10 into a forced shape and/or allowing for anatomical variations.

The one or more link plates 16 may include a first or upper link plate 34 and a second or lower link plate 36 configured to engage adjacent vertebrae. It will be appreciated that the lower link plate 36 is identical, or a mirror image, of the upper link plate 34. The link plate 34 extends from a first end 38 to a second end 40. The first end 38 of the link plate 34 includes a first opening 42 configured to receive a first portion of a first pin 32 and the second end 40 of the link plate 34 includes a second opening 44 configured to receive a first portion of a second pin 32. Similarly, the distal ends 20 of the upper endplates 22 of the respective first and second legs 12, 14 each include an opening 46 configured to receive second portions of the first and second pins 32, respectively. In this manner, the upper endplate 22 of the first leg 12 is pivotally connected to the first end 38 of the upper link plate 34 and the upper endplate 22 of the second leg 14 is pivotally connected to the second end 40 of the upper link plate 34.

Similarly, the first end 38 of the lower link plate 36 includes a first opening 42 configured to receive a first portion of a third pin 32 and the second end 40 of the lower link plate 36 includes a second opening 44 configured to receive a first portion of a fourth pin 32. Likewise, the distal ends 20 of the lower endplates 24 of the respective first and second legs 12, 14 each include an opening 46 configured to receive second portions of the third and fourth pins 32, respectively. In this manner, the lower endplate 24 of the first leg 12 is pivotally connected to the first end 38 of the lower link plate 36 and the lower endplate 24 of the second leg 14 is pivotally connected to the second end 40 of the lower link plate 36.

One or more of the endplates 22, 24 and/or link plates 34, 36 may include a plurality of teeth 26, protrusions, or other friction enhancing surfaces configured to engage bone. The endplates 22, 24 may include one or more graft openings or windows 28 and the link plates 34, 36 may include a large central graft retaining opening or window 29 configured to receive bone graft or other suitable bone growth enhancing material.

In the linear configuration shown in FIGS. 1A-1E, the implant 10 is configured to be deployed through a guide tube or cannula in a fully collapsed orientation into a disc space between adjacent vertebral bodies. The cannula may be suitable for use during a minimally invasive surgical (MIS) procedure, for example. The disc space may be accessed through a posterior approach. The cannula may be docked on the disc space through Kambin's triangle, or the anatomical area that is bordered by the disc space, exiting nerve root, and traversing nerve root. The lateral legs 12, 14 and link plates 16 may be aligned along a central longitudinal axis A such that the implant 10 may be deployed through the cannula. In FIGS. 2A-2E, while still in the collapsed position, the first lateral leg 12 is articulated relative to the links plates 16 and second lateral leg 14.

In FIGS. 3A-3G, the second lateral leg 14 is articulated relative to the link plates 16 such that the two lateral legs 12, 14 are bent or angled relative to the central link plates 16 to form a widened U-shape configuration. The lateral legs 12, 14 are also non-uniformly expanded in height, thereby passively expanding the first end 38 of the link plates 34, 36 to a greater height than the second end 40 of the link plates 34, 36. In FIGS. 4A-4F, the first and second lateral legs 12, 14 are uniformly expanded in height such that the height of the upper and lower link plates 34, 36 are substantially parallel. In FIGS. 5A-5E, a smaller degree of expansion is shown for the first and second lateral legs 12, 14, with generally parallel upper and lower link plates 34, 36. Adjusting the heights of the anterior ends (e.g., front end 20) relative to the posterior ends (e.g., rear end 18) of the lateral legs 12, 14 may adjust the lordotic angle. Expanding the lateral legs 12, 14 differently than one another may allow for coronal adjustment. The surgeon may select the amount and degree of adjustment based on the patient's anatomy and the desired surgical outcome.

Figure 6:
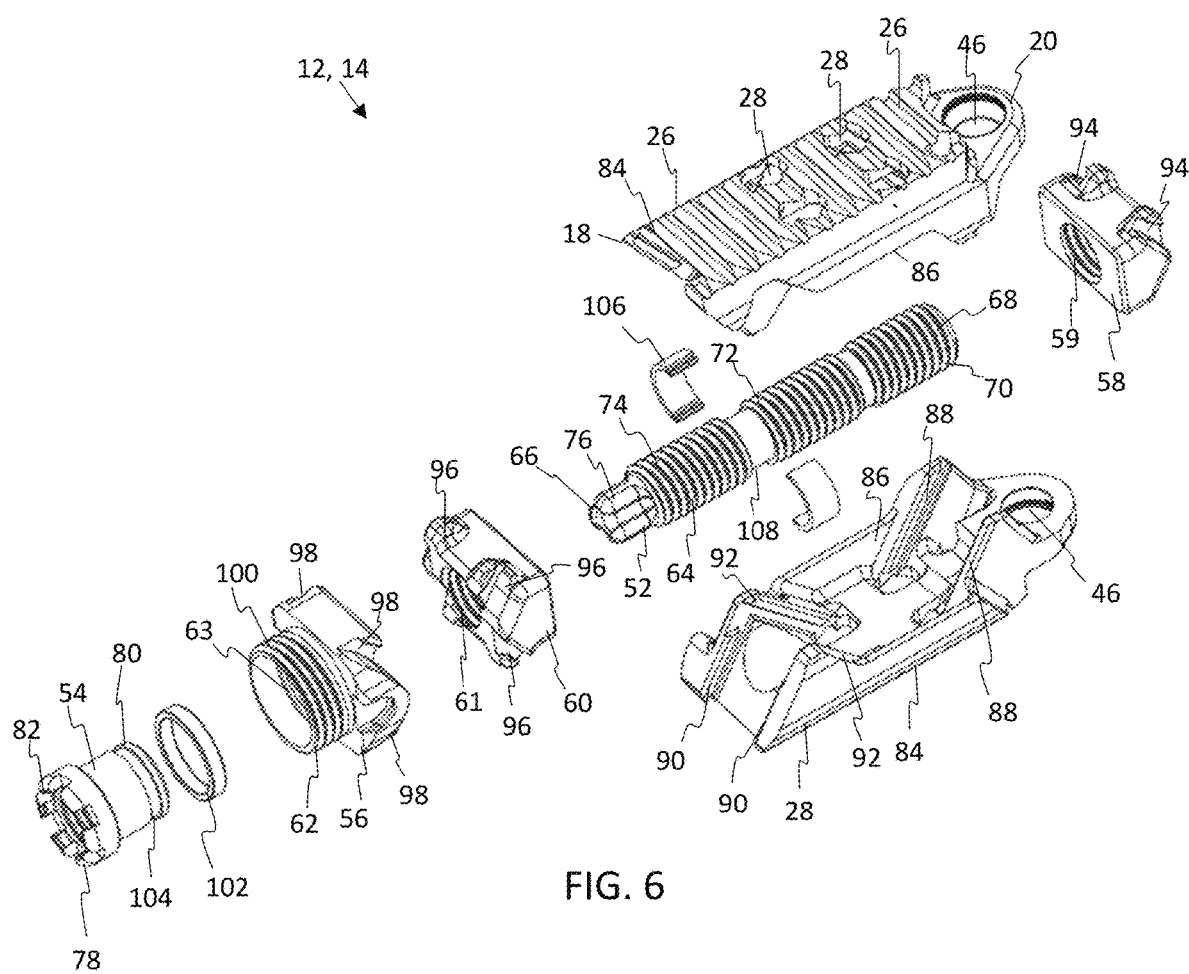
FIG. 6 is an exploded view of one of the expandable lateral legs according to one embodiment.

Turning now to FIG. 6, an exploded view of one of the lateral legs 12, 14 is shown. Each lateral leg 12, 14 includes an actuation assembly 50 including a drive screw or actuator 52 and a nut 54 configured to move a plurality of driving ramps 56, which expand the endplates 26, 28 in height. The plurality of driving ramps 56 may include a front ramp 58, a mid-ramp 60, and a rear ramp 62. The front ramp 58 may include a central longitudinal bore 59, the mid-ramp 60 may include a central longitudinal bore 61, and the rear ramp 62 may include a central longitudinal bore 63. The plurality of driving ramps 58, 60, 62 may be positioned along the length of the actuator 52 and are configured to engage and drive the upper and lower endplates 26, 28, respectively. When one or more of the driving ramps 58, 60, 62 are moved, they slide against the upper and lower endplates 26, 28, thereby providing for expansion of the leg 12, 14 in height. The expansion may include the ability to individually adjust the anterior and/or posterior heights of the lateral legs 12, 14.

Each of the lateral legs 12, 14 may include an actuation assembly 50 configured to independently expand the respective heights of the lateral legs 12, 14. The actuation assembly 50 includes a rotatable actuator 52 and rotatable nut 54 configured to move a plurality of internal ramps 56. Each lateral leg 12, 14 includes at least three driving ramps: front ramp 58, mid-ramp 60, and rear ramp 62, which interface with the actuator 52. The actuator 52 may include a shaft 64 extending from a proximal end 66 to a distal end 68. The shaft 64 may include a first threaded portion 70, a second threaded portion 72, and a third threaded portion 74. The second threaded portion 72 may be positioned between the first and third threaded portions 74. The threaded portions 70, 72, 74 may have the same or different attributes including outer diameters, handedness, thread form, thread angle, lead, pitch, etc.

Figure 7A:
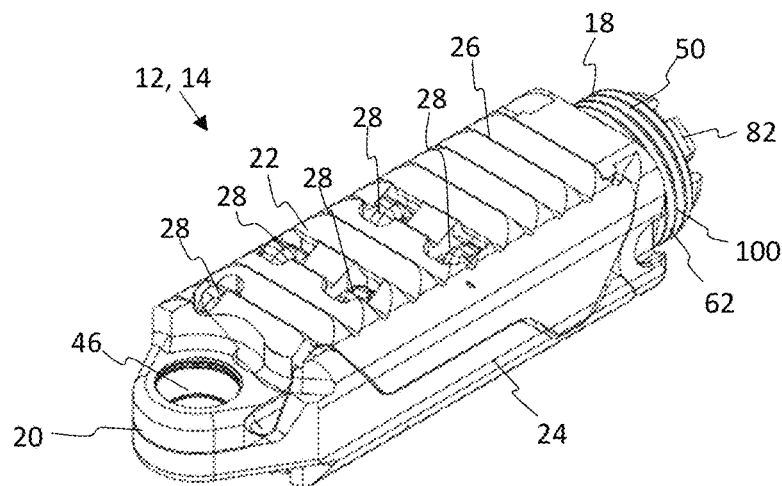
FIGS. 7A-7G show perspective, rear, side, top and cross-sectional views, respectively, of the lateral leg shown in FIG. 6 in a fully collapsed configuration.
Figure 7B:
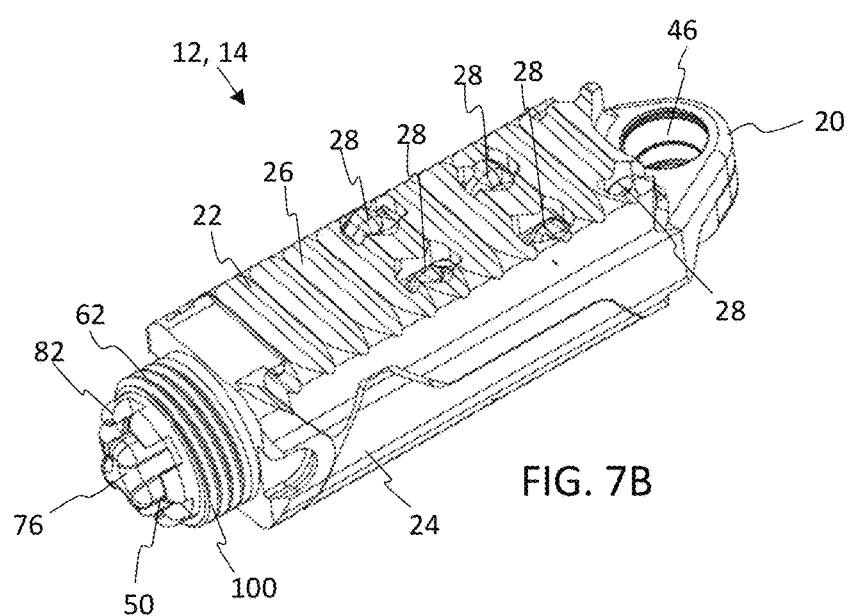
Figure 7C:
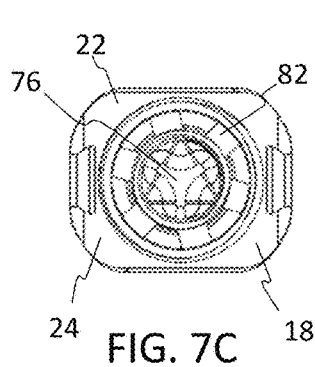
Figure 7D:
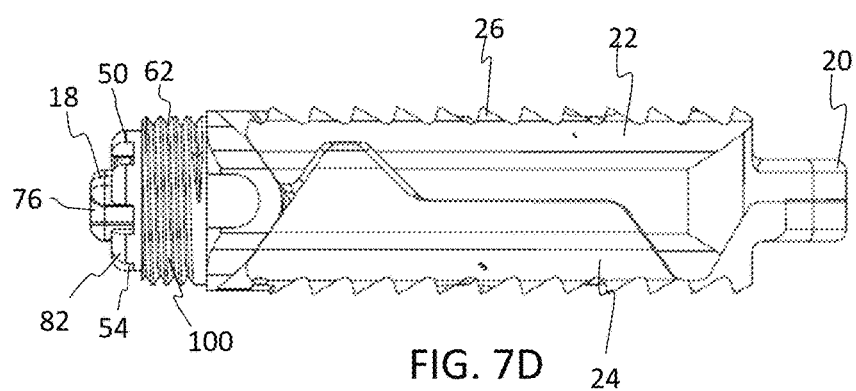
Figure 7E:
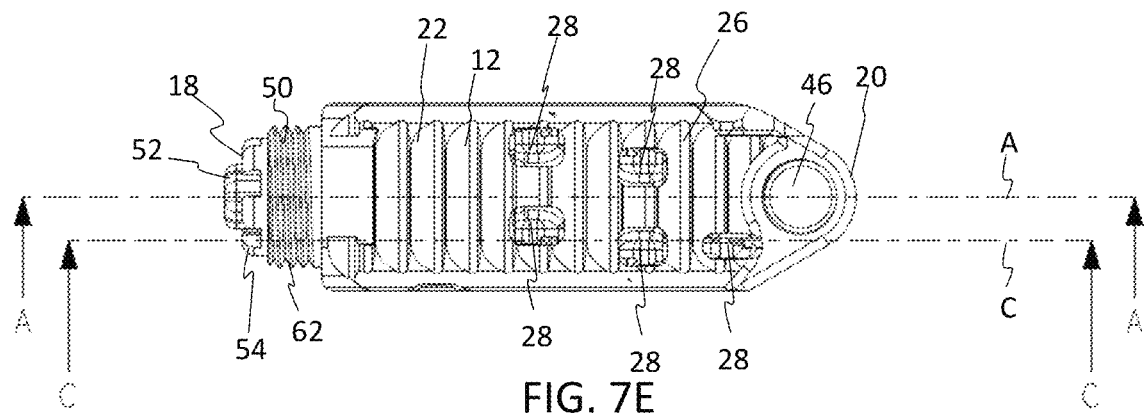
Figure 7F:
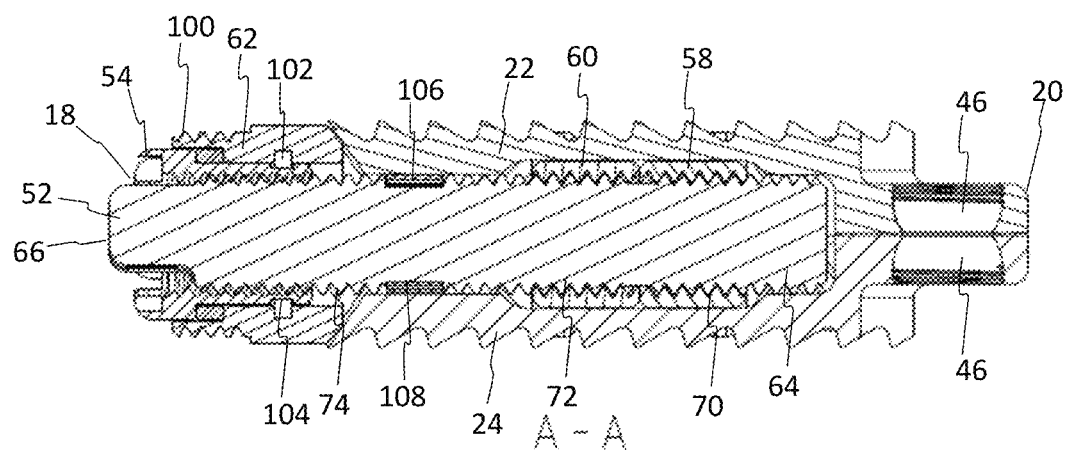
Figure 7G:
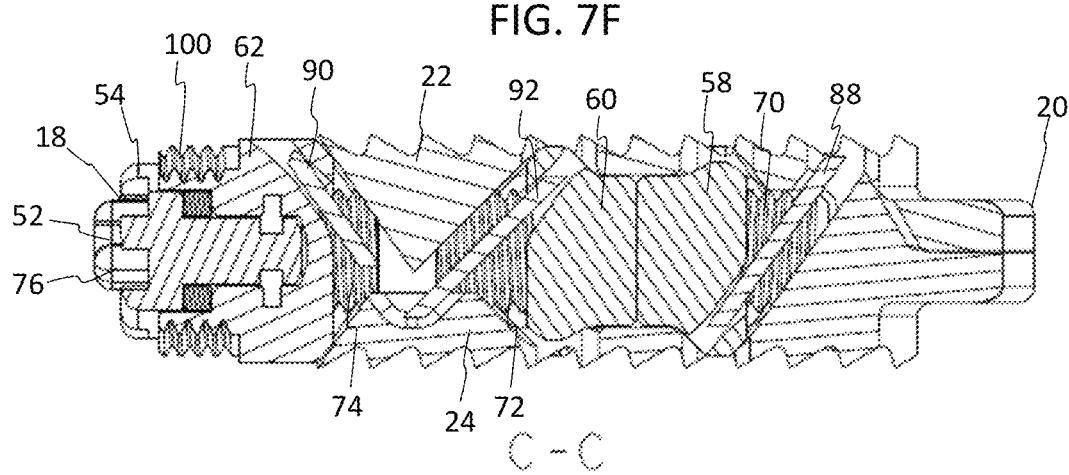
Figure 8A:
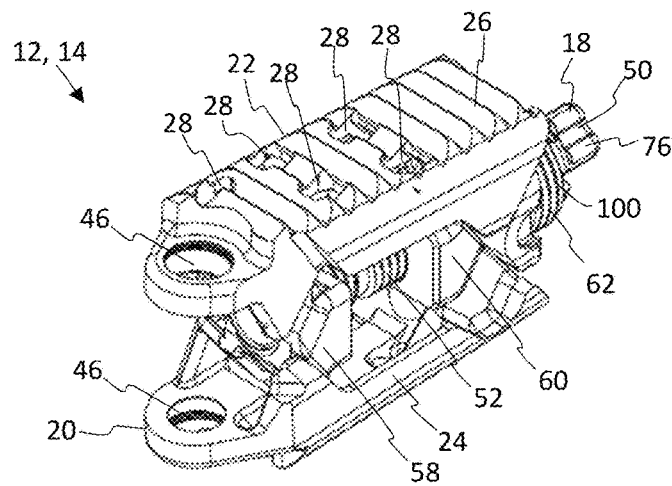
FIGS. 8A-8G show perspective, rear, side, top, and cross-sectional views, respectively, of the lateral leg shown in FIG. 6 in an expanded configuration.
Figure 8B:
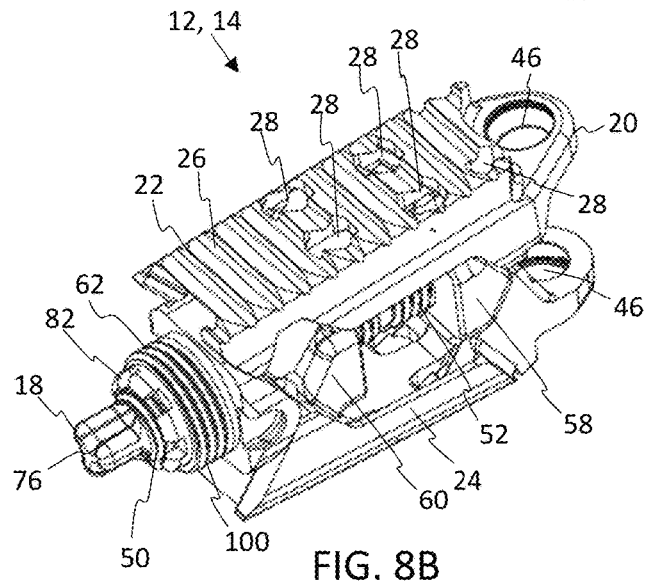
Figure 8C:
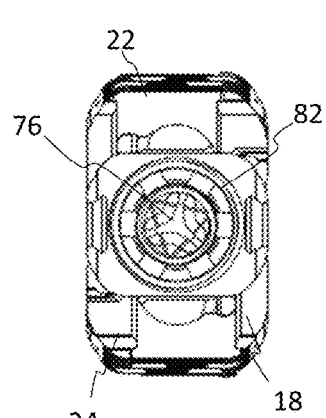
Figure 8D:
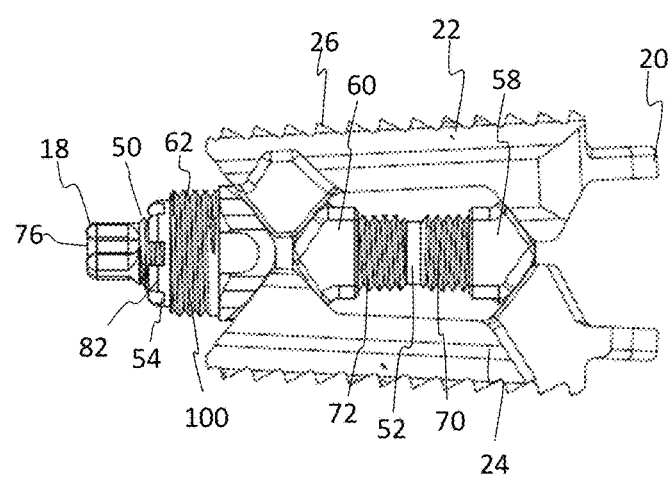
Figure 8E:
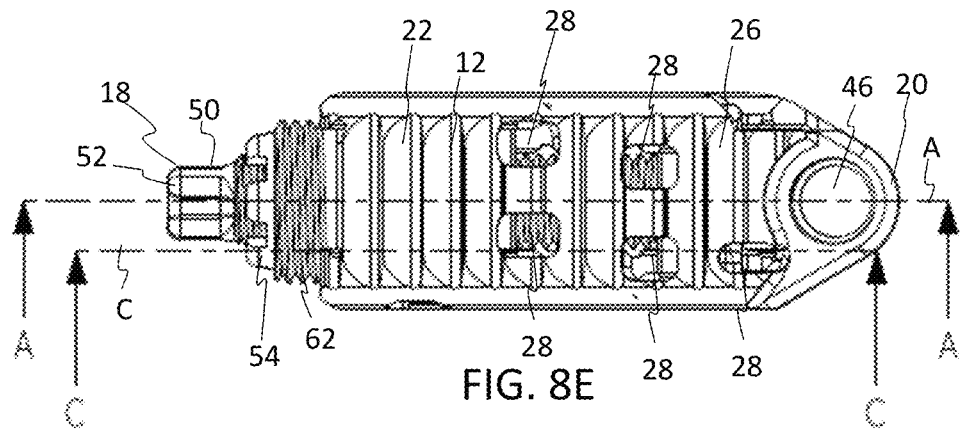
Figure 8F:
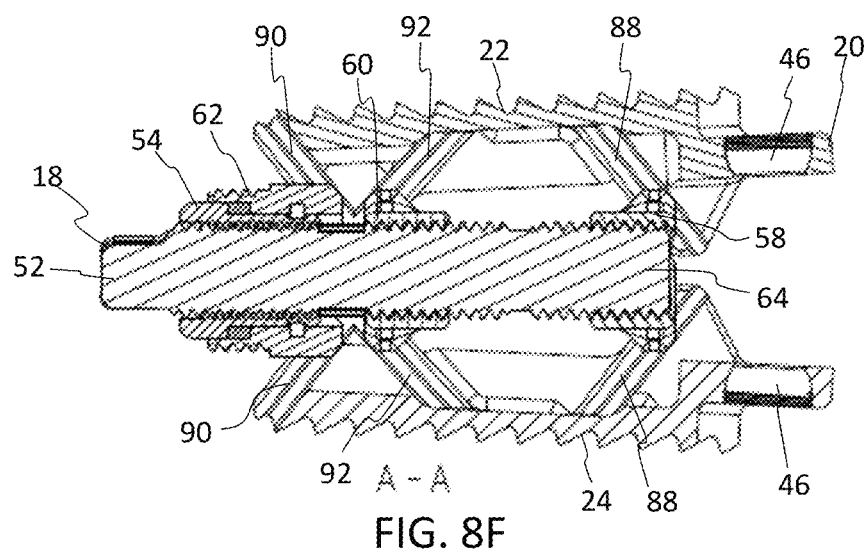
Figure 8G:
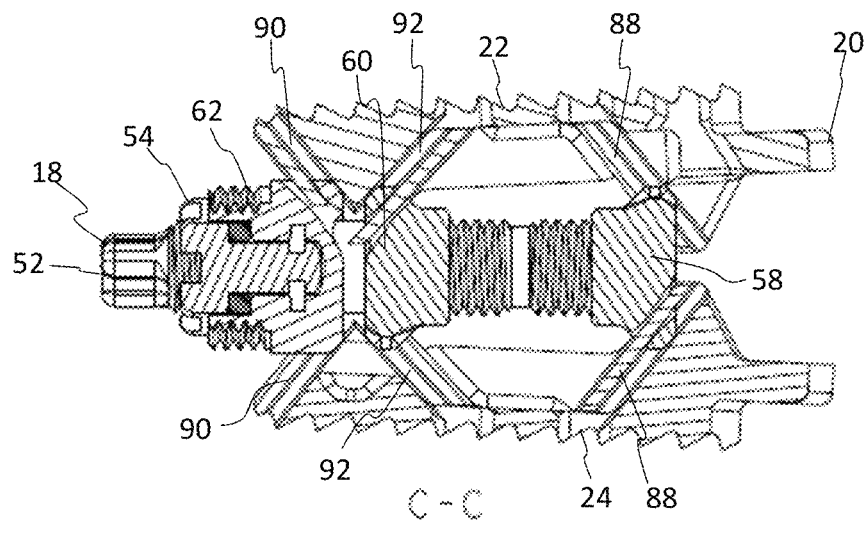
Figure 9A:
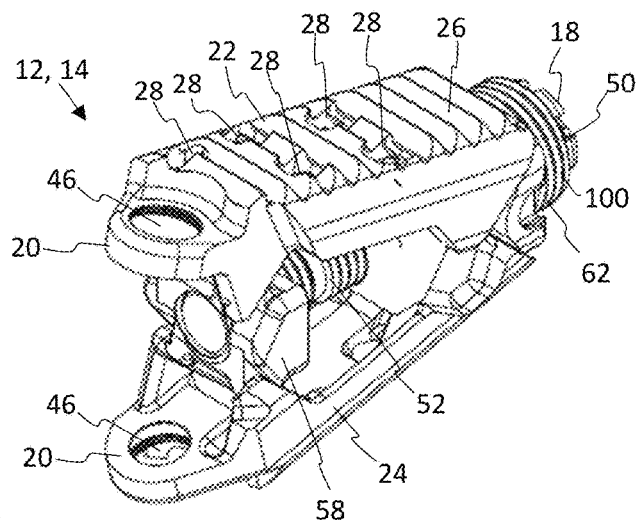
FIGS. 9A-9G show perspective, rear, side, top, and cross-sectional views, respectively, of the lateral leg shown in FIG. 6 in an expanded configuration with a greater anterior height.
Figure 9B:
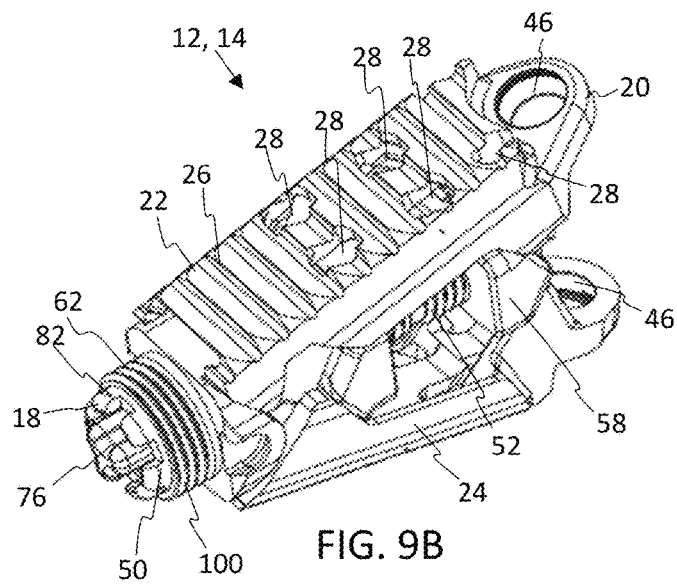
Figure 9C:
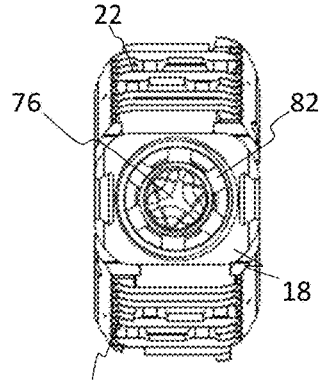
Figure 9D:
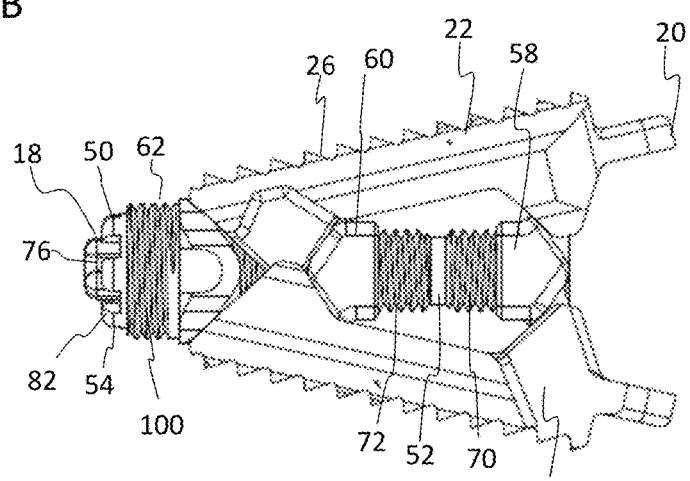
Figure 9E:
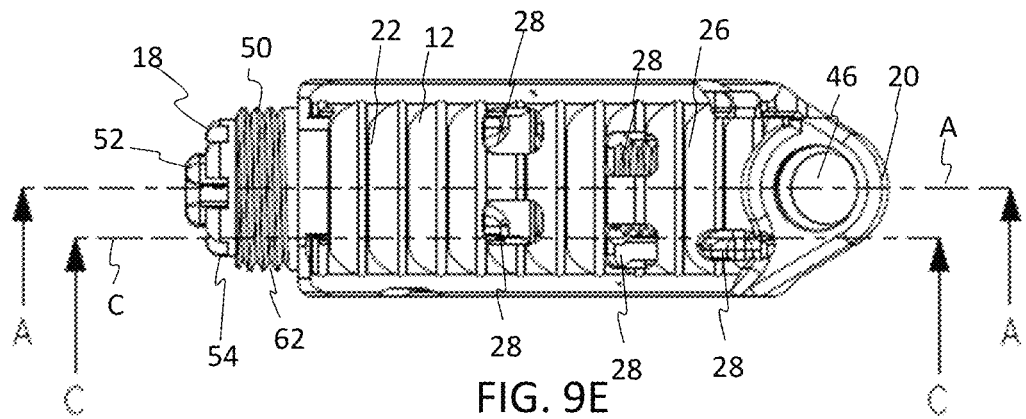
Figure 9F:
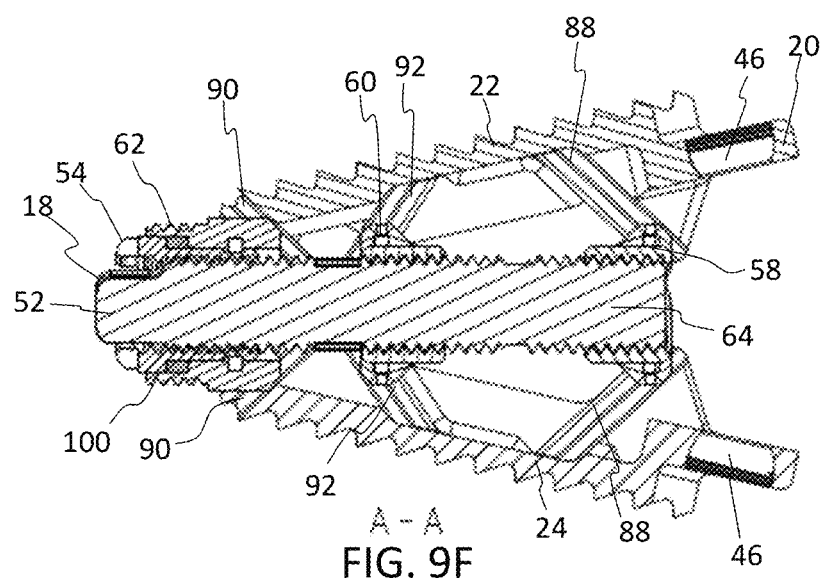
Figure 9G:
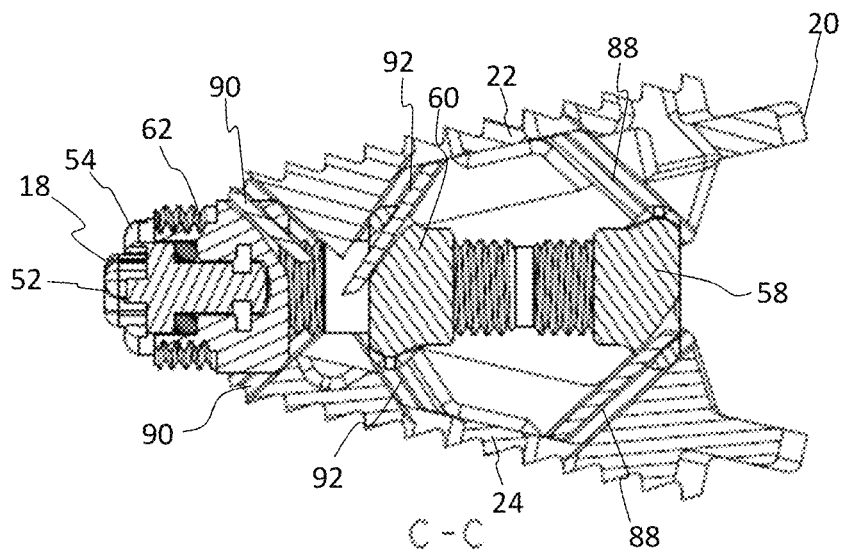
Figure 10:
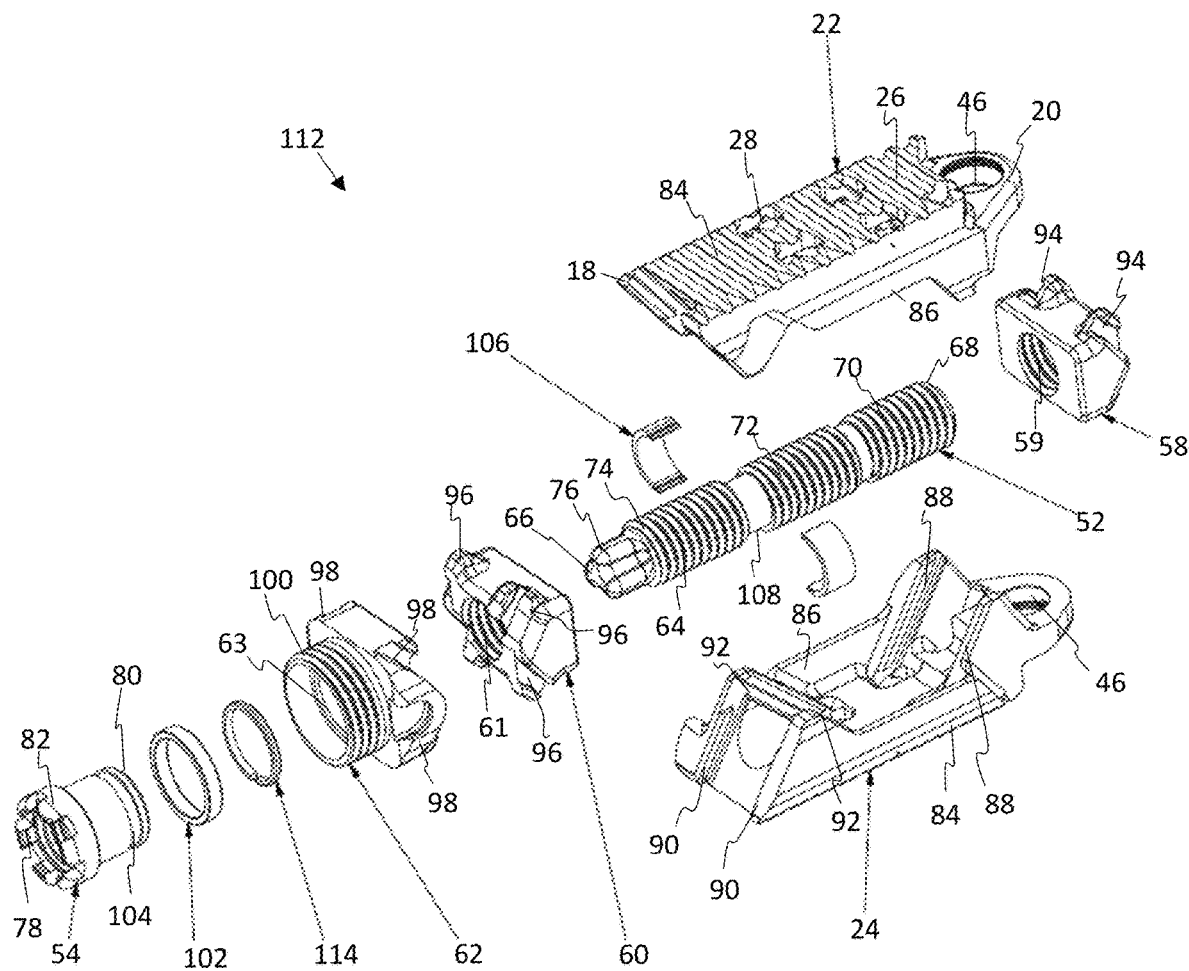
FIG. 10 is an exploded view of one of the expandable lateral legs according to another embodiment.
Figure 11E:
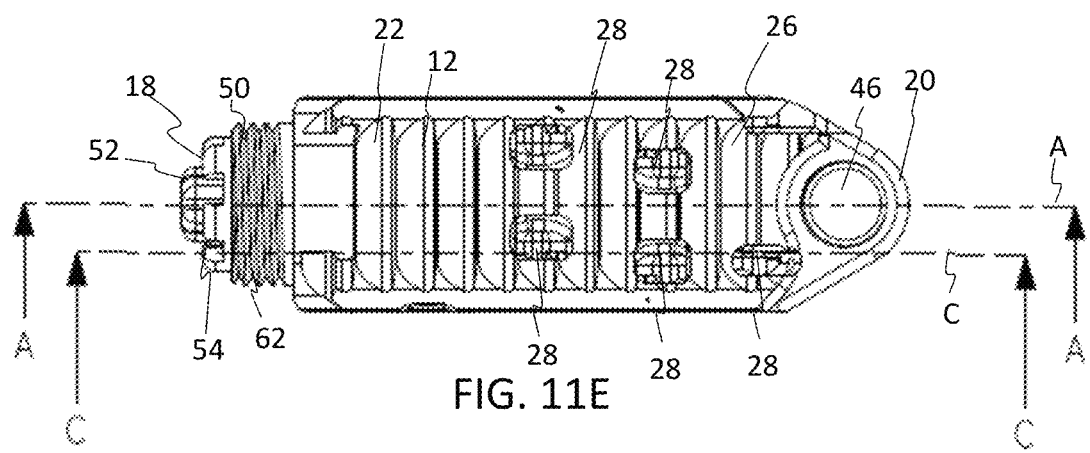
Figure 11F:
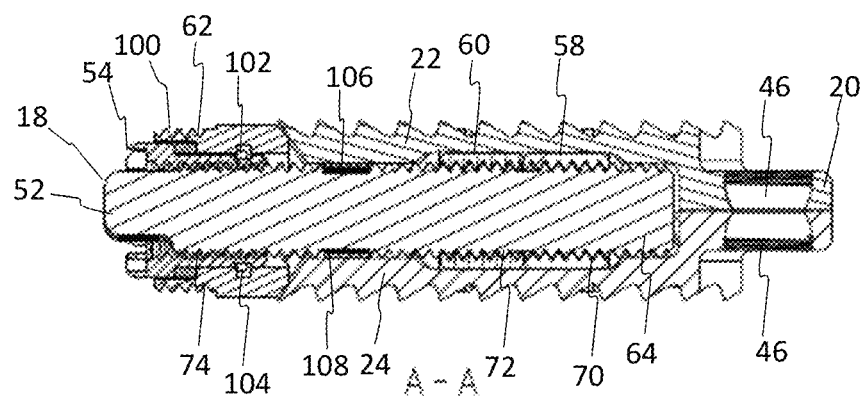
Figure 11G:
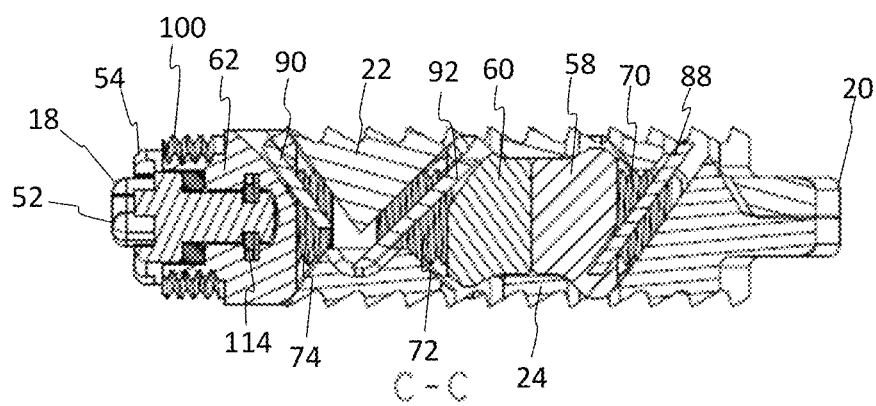
Figure 12A:
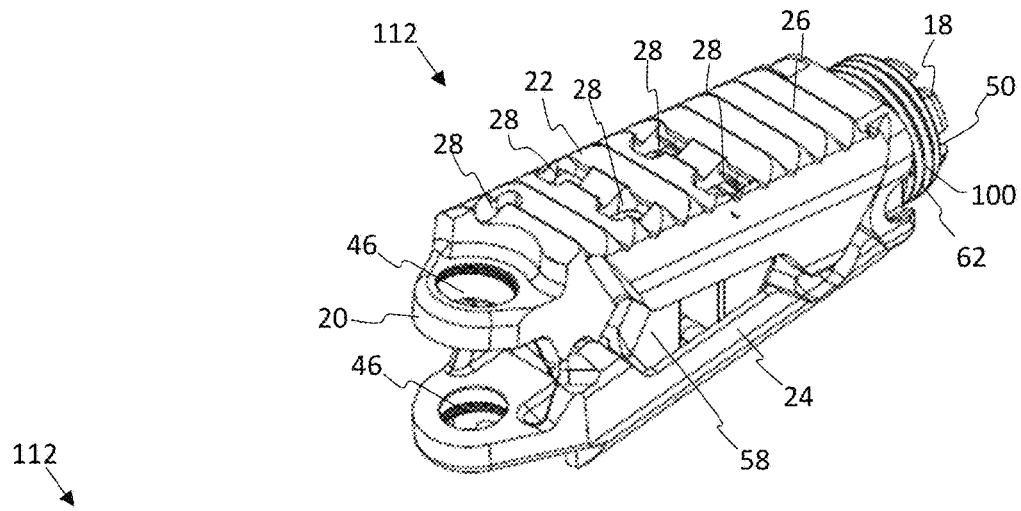
FIGS. 12A-12G show perspective, rear, side, top, and cross-sectional views, respectively, of the lateral leg shown in FIG. 10 in an expanded configuration.
Figure 12B:
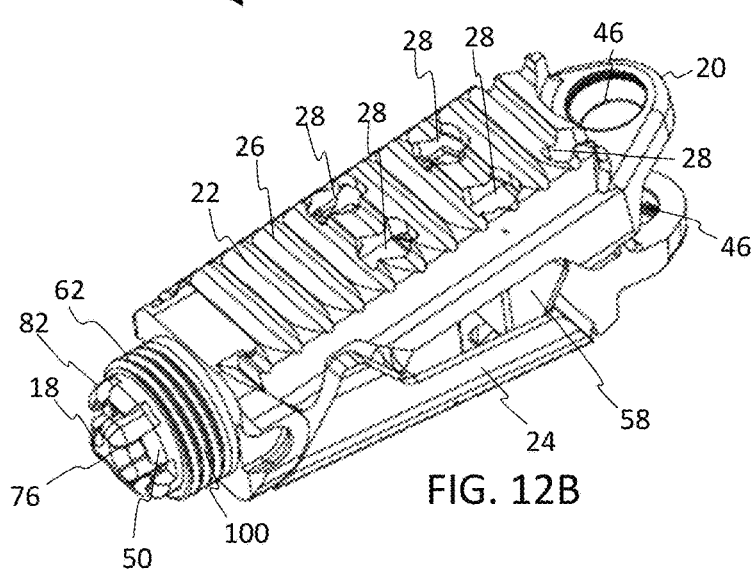
Figure 12C:
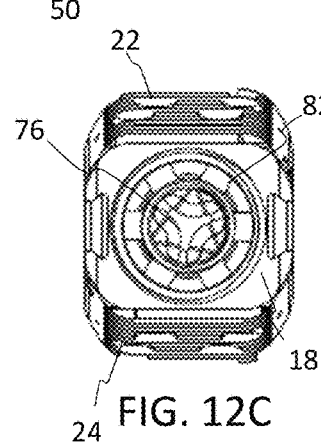
Figure 12D:
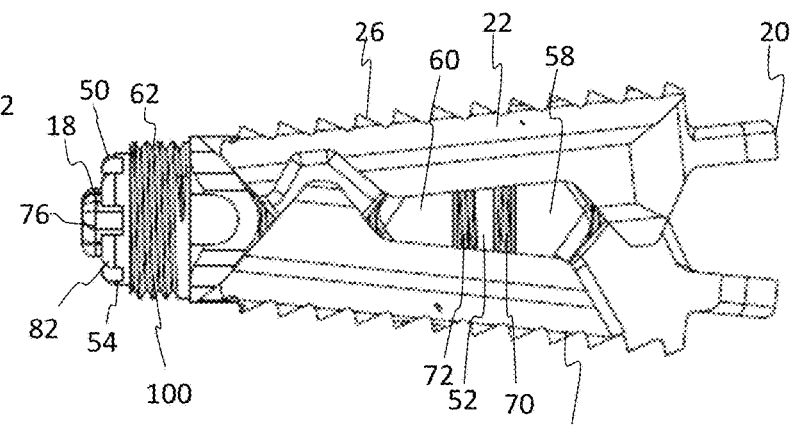
Figure 12E:
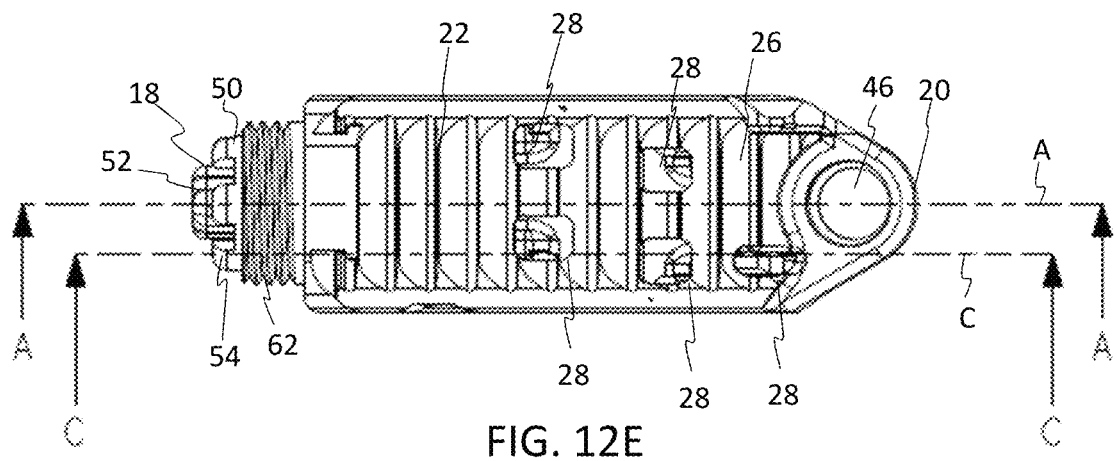
Figure 12F:
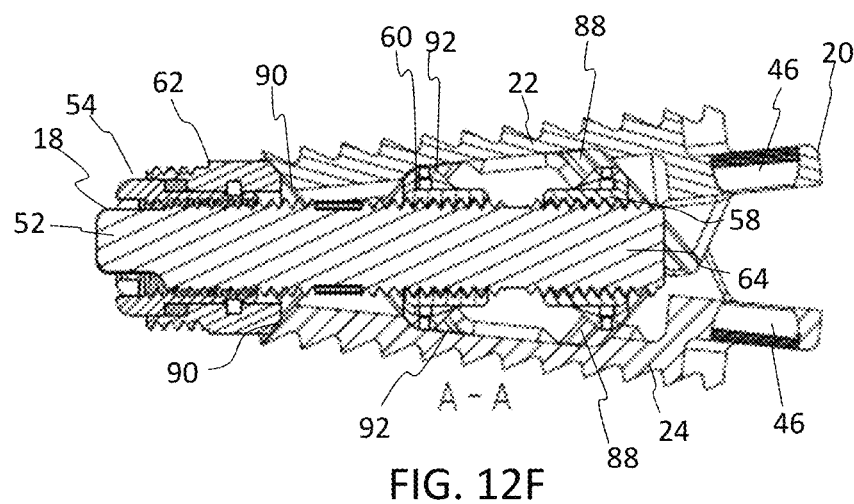
Figure 12G:
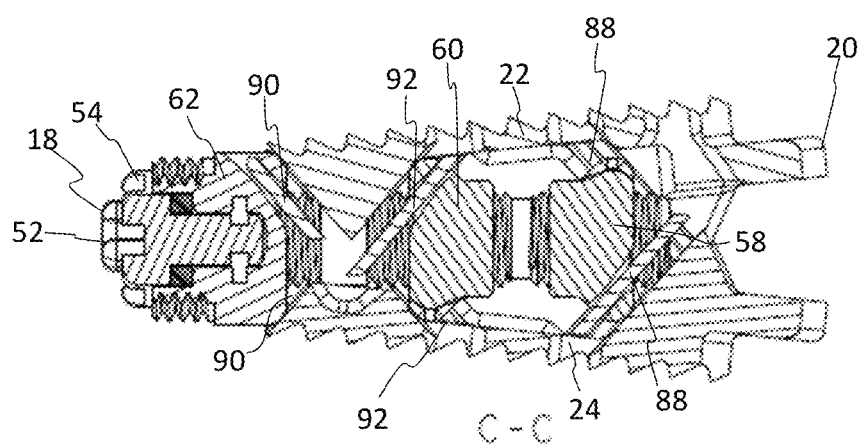
Figure 13A:
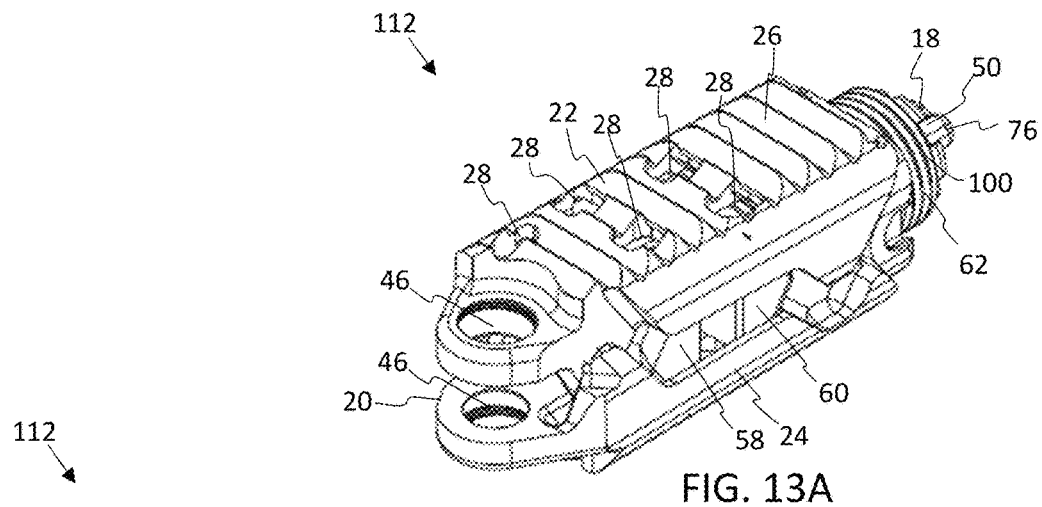
FIGS. 13A-13G show perspective, rear, side, top, and cross-sectional views, respectively, of the lateral leg shown in FIG. 10 in another expanded configuration.
Figure 13B:
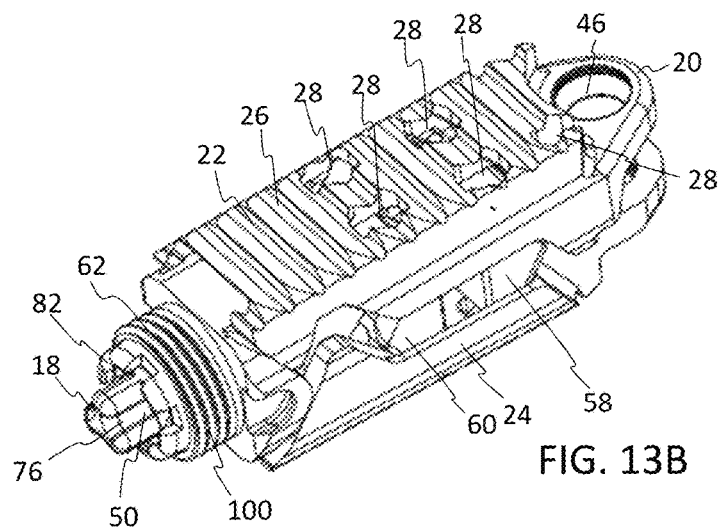
Figure 13C:
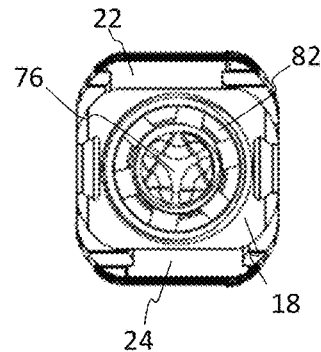
Figure 13D:
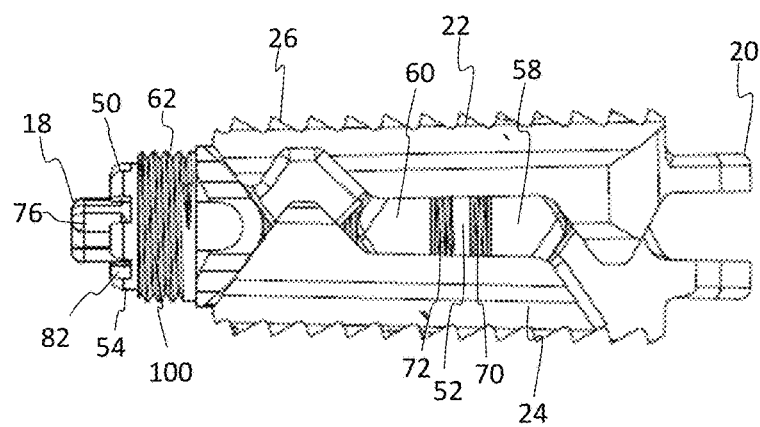
Figure 13E:
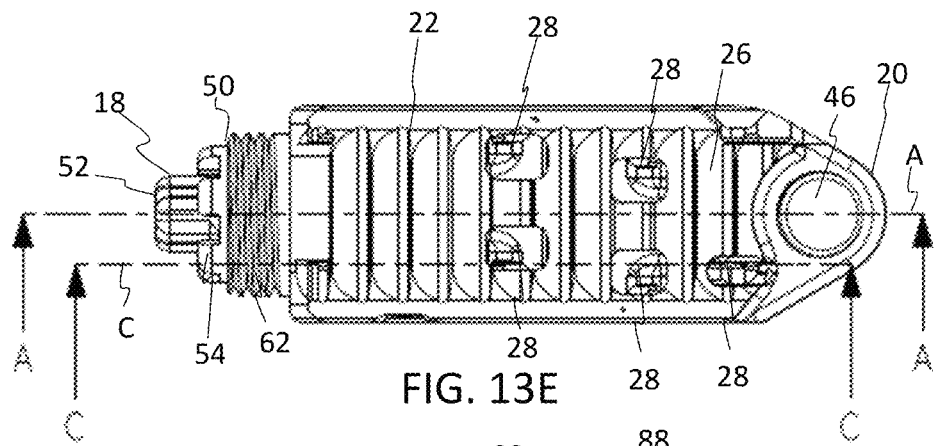
Figure 13F:
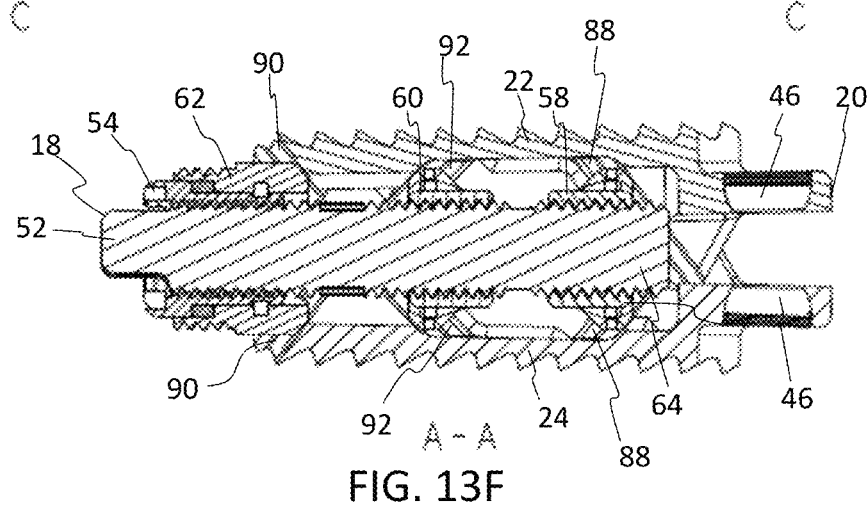
Figure 13G:
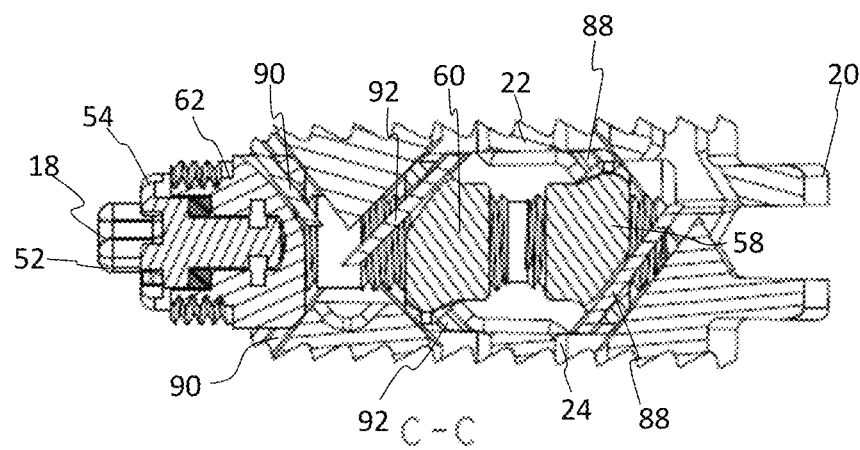
Figure 14A:
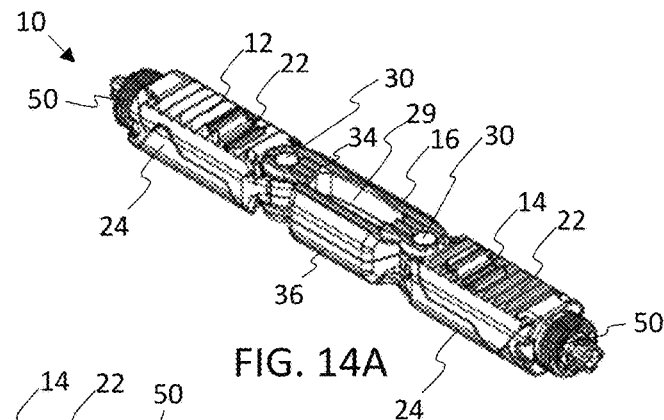
FIGS. 14A-14E show perspective, top, rear, side, and exploded views of the expandable fusion device according to one embodiment, in a fully collapsed and linear orientation configured to be inserted into the body.
Figure 14B:
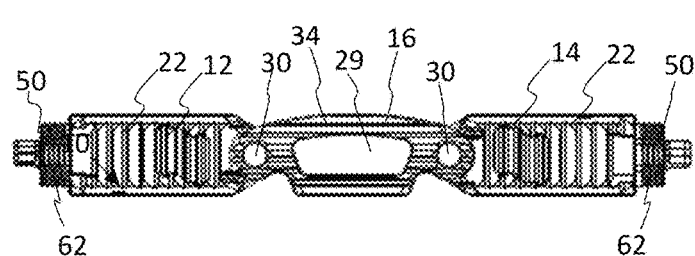
Figure 14C:
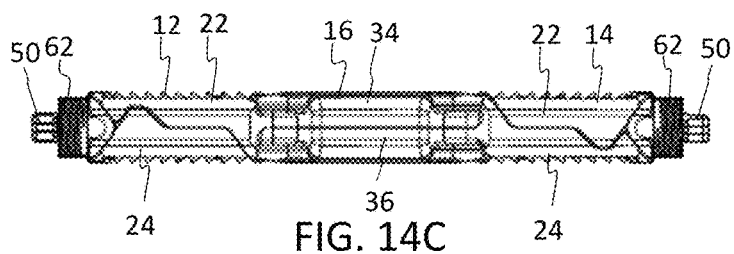
Figure 14D:
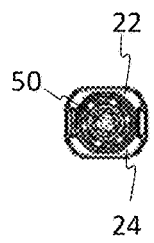
Figure 14E:
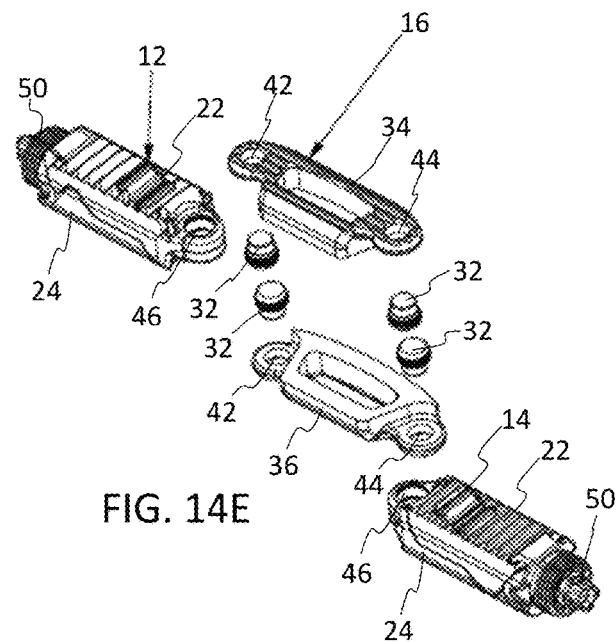
Figure 16A:
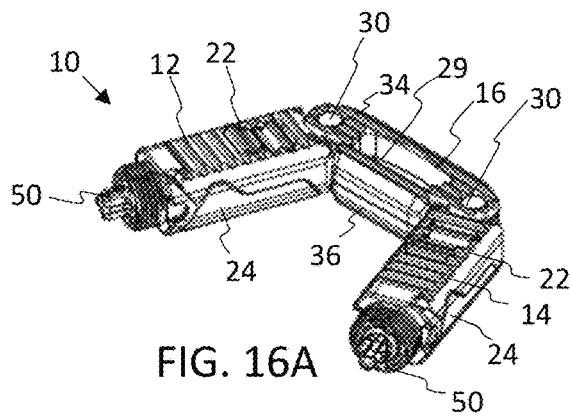
FIGS. 16A-16E show perspective, top, rear, side, and exploded views of the expandable fusion device in FIGS. 15A-15E with both of the lateral legs hinged relative to the link plates to form a widened U-shaped configuration, and the implant is in the fully collapsed position.
Figure 16B:
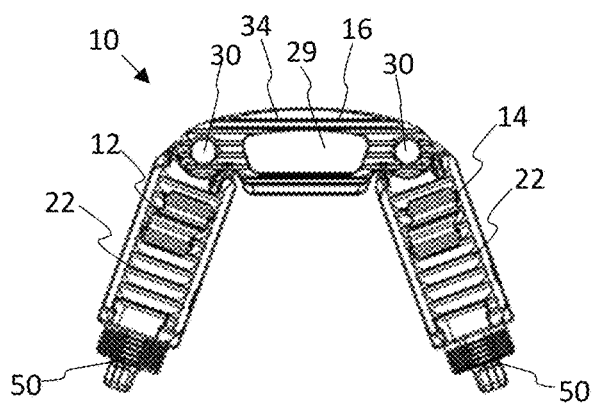
Figure 16C:
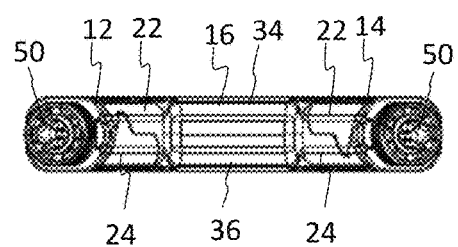
Figure 16D:
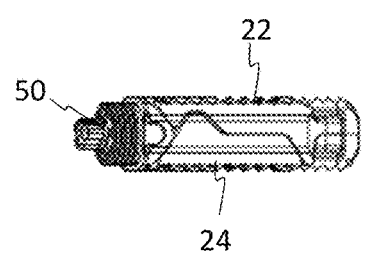
Figure 16E:
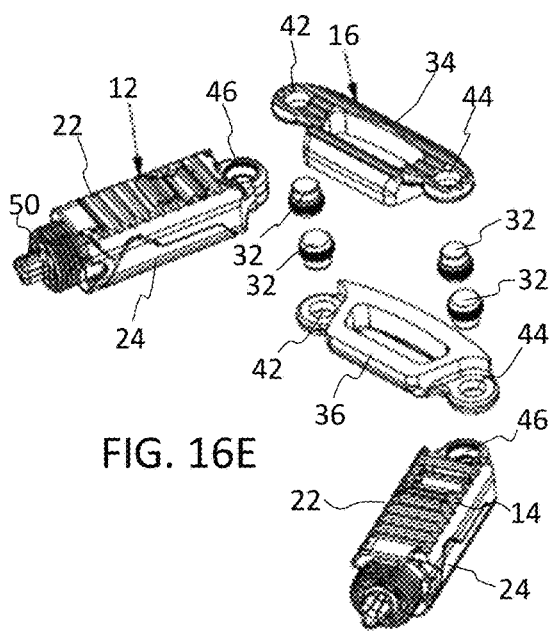
Figure 17A:
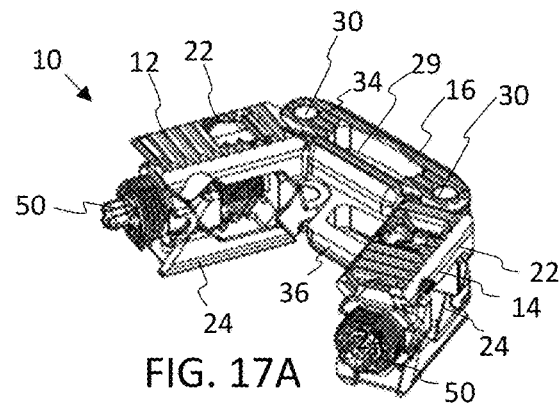
FIGS. 17A-17E show perspective, top, rear, side, and exploded views of the expandable fusion device in FIGS. 16A-16E with both lateral legs and attached link plates expanded in parallel.
Figure 17B:
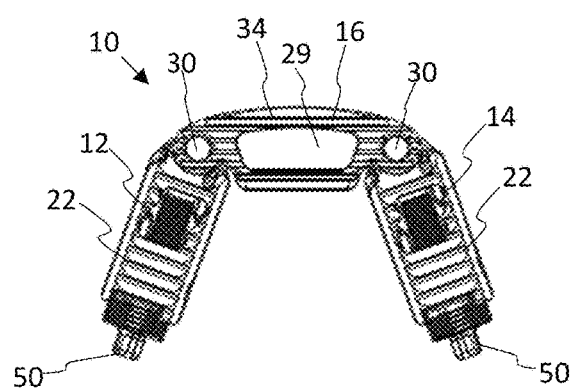
Figure 17C:
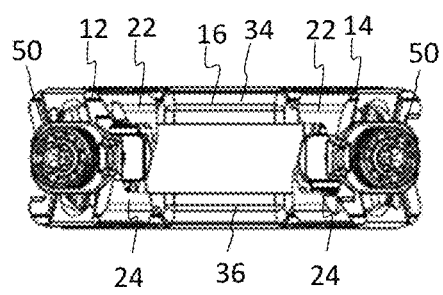
Figure 17D:
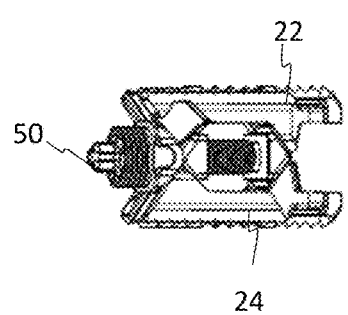
Figure 17E:
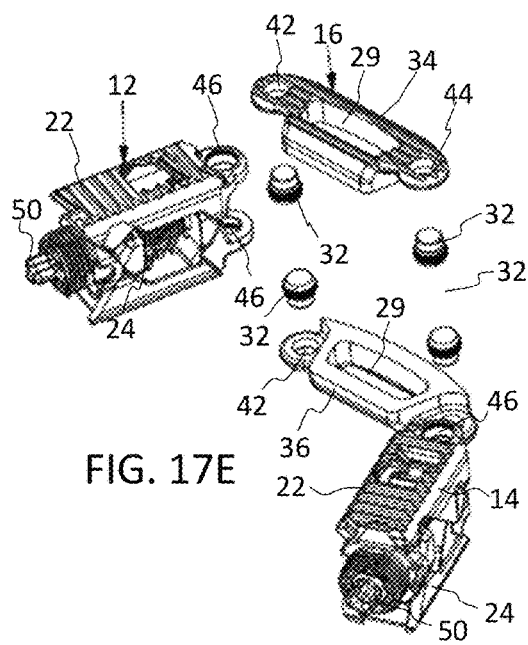
Figure 18A:
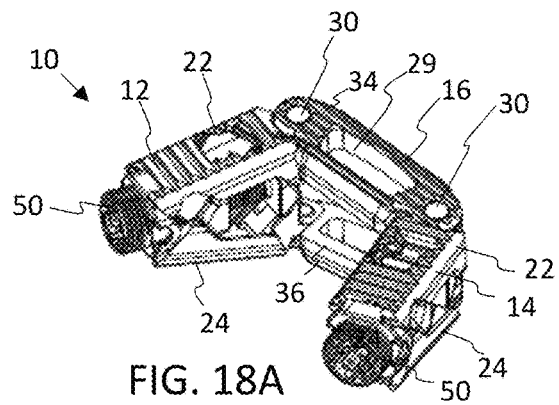
FIGS. 18A-18E show perspective, top, rear, side, and exploded views of the expandable fusion device in FIGS. 17A-17E with the lateral legs non-uniformly expanded.
Figure 18B:
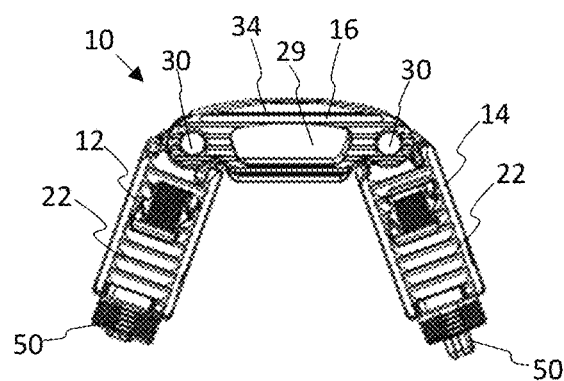
Figure 18C:
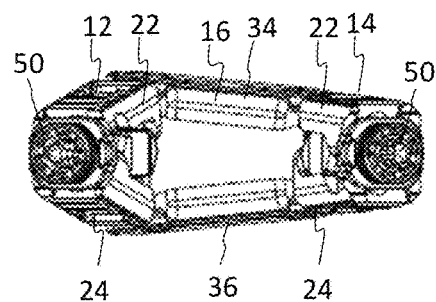
Figure 18D:
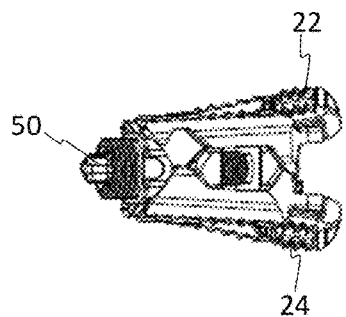
Figure 18E:
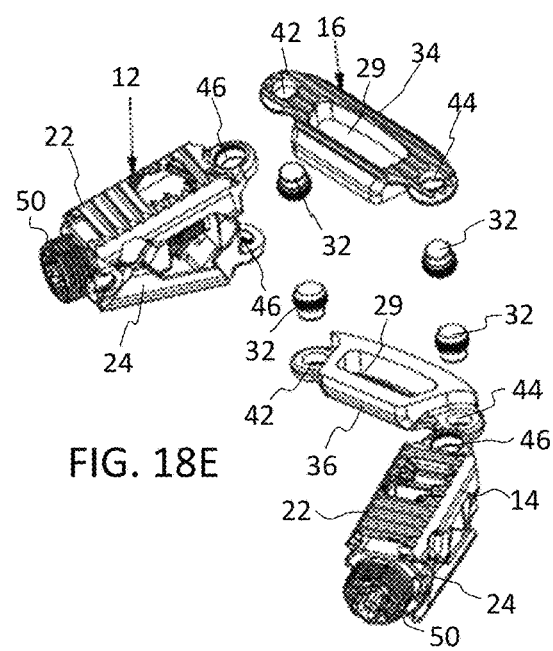
Figure 19A:
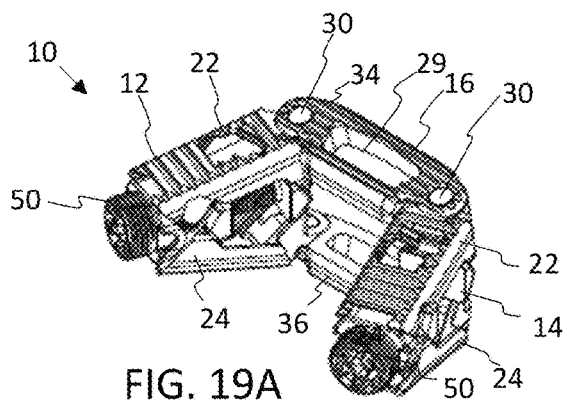
FIGS. 19A-19E show perspective, top, rear, side, and exploded views of the expandable fusion device in FIGS. 17A-17E with both lateral legs uniformly expanded.
Figure 19B:
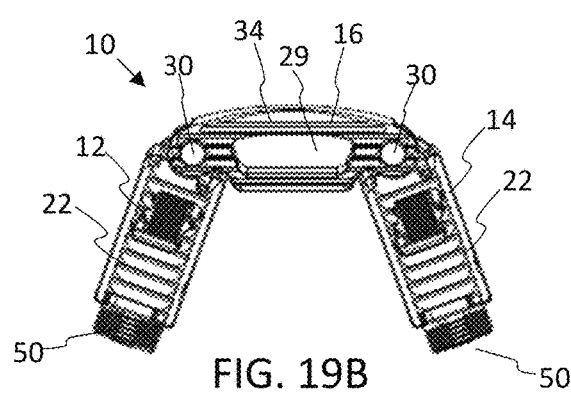
Figure 19C:
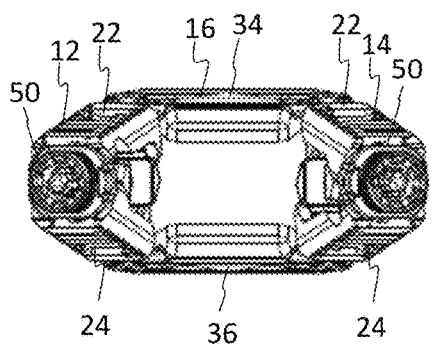
Figure 19D:
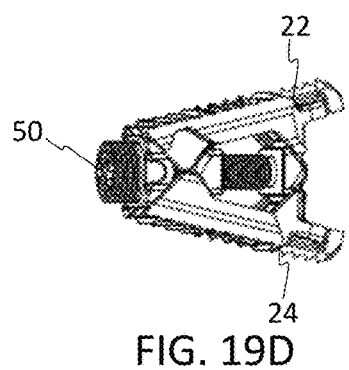
Figure 19E:
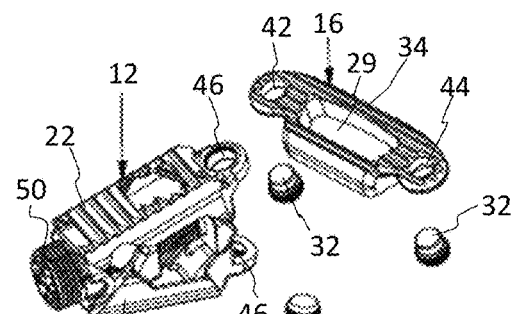

FIG. 7E shows the lateral leg 12 with a central longitudinal axis A and a longitudinal axis C offset to axis A. FIG. 7F shows FIG. 7E along line A-A and FIG. 7G shows FIG. 7E along line C-C. As best seen in FIG. 7F, the front driving ramp 58 includes a threaded bore 59, and the front driving ramp 58 is positioned on the first threaded portion 70 of the actuator 52. The front driving ramp 58 is threadedly moveable along the length of the first threaded portion 70. The mid-ramp 60 includes a threaded bore 61, and the mid-ramp 60 is positioned on the second threaded portion 72 of the actuator 52. The mid-ramp 60 is threadedly moveable along the length of the second threaded portion 72 of the actuator 72. The rear ramp 62 is engaged with the nut 54, which is positioned along the third threaded portion 74 and is moveable along the length of the third threaded portion 74. The driving ramps 56 are each moveable along their respective threaded portions 70, 72, 74 to move the upper and lower endplates 26, 28, and thereby expand the lateral leg 12, 14. The threaded portions 70, 72, 74 may have the same or different outer diameters and/or handedness. The proximal end 66 of the actuator shaft 64 may include a first instrument retention feature, such as a ribbed neck 76. The ribbed neck 76 may include knurled neck grips or other suitable engagement surfaces, which are configured to interface with a driver instrument to thereby rotate the actuator shaft 64.

The actuation assembly 50 may include a rotatable nut 54. The rotatable nut 54 may be configured to move the rear ramp 62 independent of the mid-ramp 60 and front ramp 58. The nut 54 may extend from a proximal end 78 to a distal end 80. The proximal end 78 may include a second instrument retention feature, such as a slotted head 82. The slotted head 82 may include slots or other suitable engagement surfaces configured to interface with a driver instrument to thereby rotate the nut 54. When only the nut 54 is rotated clockwise, the rear ramp 62 may be translated forward, decreasing it's distance to the front ramp 58 such that the posterior height increases and the anterior height decreases, thus decreasing the lordotic angle of the spacer. When the nut 54 remains stationary and only the actuator 52 is rotated clockwise, the mid ramp 60 moves away from the front ramp 58 increasing the anterior height, at the same time the rear ramp 62 moves away relative to the front ramp 58 as the actuator 52 advances through the nut 54. increasing the gap between the rear ramp 62 and the front ramp 58 increases the lordotic angle of the spacer. When both the actuator 52 and the nut 54 are rotated clockwise at the same time, the rear ramp 62 and front ramp 58 do not move relative to each other. Only the mid ramp 60 translates away from the front ramp 58 and towards the rear ramp 62. This results in expansion of the endplates 26, 28 in parallel. It will be appreciated that the movement of the driving ramps 58, 60, 62 and resulting expansion may be operated by the actuator 52 and/or nut 54 with any suitable configurations and mechanisms.

The driving ramps 58, 60, 62 engage with upper and lower endplates 26, 28 to thereby move the upper and lower endplates 26, 28 outwardly in height. It will be appreciated that the lower endplate 28 is identical, or a mirror image of, the upper endplate 26 and the description for the upper endplate 26 herein applies equally to the lower endplate 28. The upper endplate 26 includes an outer surface 84 configured to engage the adjacent vertebrae and an inner surface 86 configured to mate with the driving ramps 58, 60, 62. The inner surface 86 may include one or more ramped surfaces 88, 90, 92. In the embodiment shown, the inner surface 86 includes at least one first ramped surface 88 near the distal end of the endplate 26, 28, at least one second ramped surface 90 near the proximal end of the endplate 26, 28, and at least one third ramped surface 92 between the first and second ramped surfaces 88, 90. For example, the inner surface 86 may include a pair of first ramped surfaces 88, a pair of second ramped surfaces 90, and a pair of third ramped surfaces 92. The first and second ramped surfaces 88, 90 may face the proximal end, and the third ramped surface 92 may face the distal end of the endplate 26, 28.

The ramped surfaces 88, 90, 92 may be angled continuous surfaces with a given angle of slope. It is contemplated that the slope of the ramped surfaces 88, 90, 92 may be equal or can differ from each other. The ramped surfaces 88, 90, 92 may be generally straight ramped surfaces or may be curved ramped surfaces. The ramped surfaces 88, 90, 92 may include male slide ramps or protruding ramps. The first and second ramped surfaces 88, 90 may be spaced apart at an equal distance such that the ramped surfaces 88, 90 are substantially parallel to one another. The third ramped surface 92 may be angled opposite to the first and second ramped surfaces 88, 90. In this way the apex of the third ramp 92 may meet or near the apex of the second ramp 90 and the base of the third ramp 92 may extend toward the base of the first ramp 88. Although a specific arrangement of ramped surfaces 88, 90, 92 is shown, it is envisioned that the number, location, and configuration of ramped surfaces 88, 90, 92 may be modified or selected by one skilled in the art.

The driving ramps 58, 60, 62 may include one or more ramped surfaces 94, 96, 98. The ramped surfaces 94, 96, 98 of the driving ramps 58, 60, 62 may be configured and dimensioned to engage the corresponding ramped surfaces 88, 90, 92 of the upper and lower endplates 26, 28, respectively. For example, the front ramp 58 may include one or more ramped surfaces 94, mid-ramp 60 may include one or more ramped surfaces 96, and rear ramp 62 may include one or more ramped surfaces 98. For example, the front ramp 58 may include a first pair of upper ramped surfaces 94 and a second pair of lower ramped surfaces 94. The mid-ramp 60 may include a first pair of upper ramped surfaces 96 and a second pair of lower ramped surfaces 96. The rear ramp 62 may include a first pair of upper ramped surfaces 98 and a second pair of lower ramped surfaces 98. The ramped surfaces 94, 96, 98 may be angled continuous surfaces with a given angle of slope. It is contemplated that the slope of the ramped surfaces 94, 96, 98 may be equal or can differ from each other.

The ramped surfaces 94, 96, 98 may be generally straight ramped surfaces or may be curved ramped surfaces. The ramped surfaces 94, 96, 98 may include female slide ramps or recessed ramps configured to receive the male ramped surfaces 88, 90, 92 of the upper and lower endplates 26, 28, respectively. A dovetail type connection may be formed between the ramped surfaces for stability and reliability, although other mating and sliding engagements can be used. It will be appreciated that the male and female ramps may be reversed or may be otherwise configured to provide for slidable mating between the ramps.

The first ramped surface 88 of the endplate 26, 28 may be configured to slidably interface with the ramped surface 94 of the front driving ramp 58. The second ramped surface 90 of the endplate 26, 28 may be configured to slidably interface with the ramped surface 98 of the rear ramp 62. The third ramped surface 92 of the endplate 26, 28 may be configured to slidably interface with the ramped surface 96 of the mid-ramp 60. As one or more of the driving ramp 58, 60, 62 moves, the ramped surface or surfaces 94, 96, 98 pushes against the corresponding ramped surface or surfaces 88, 90, 92 of the upper and lower endplates 26, 28. In this manner, the individual driving ramps 58, 60, 62 control the rate of expansion of the upper and lower endplates 26, 28. The upper and lower endplate 26, 28 are pushed outwardly into the expanded configuration.

The actuation assembly 50 may further include one or more of the following features. The driving rear ramp 62 may include an outer threaded portion 100 at the proximal end which may be configured to be retained by an insertion instrument. One or more securing rings or washers 102 may be provided to secure the nut 54 to the assembly 50. For example, the securing washer 102 may be received in an annular channel 104 near the distal end 80 of the nut 54, thereby connecting the rear ramp 56 to the nut 54. One or more friction rings may also be provided to provide drag or thrust resistance to the nut 54 and/or driving ramps 58, 60, 62, respectively. A split ring 106 may be provided to capture and secure the actuator 52 in the assembly 50. The split ring 106 may be provided along a non-threaded portion 108 of the shaft 64, for example, having a reduced diameter between the second and third threaded portions 72, 74.

With emphasis on FIGS. 10-13, another embodiment of an expandable lateral leg 112 is shown. Lateral leg 112 is similar to lateral legs 12, 14, with the addition of a retaining ring or snap ring 114 in the actuation assembly 50. The retaining ring or snap ring 114 may be used to further secure the nut 54 to the rear driving ramp 56. The snap ring 114 may fit into a recessed groove inside the rear driving ramp 56, for example. Once installed, the exposed portion of the snap ring 114 may act as a shoulder to retain the rear driving ramp 56 to the nut 54. FIGS. 11A-11G show the expandable lateral leg 112 in its fully collapsed position. FIGS. 12A-12G show the expandable lateral leg 112 in one expanded position, where the front ramp 58 is advanced toward the distal end 20 and the mid-ramp 60 is advanced away from the front 58 toward the proximal end 18 of the lateral leg 112. FIGS. 13A-13G show the upper and lower endplates 22, 24 expanded substantially in parallel.

Turning now to FIGS. 14-19, the implant 10 may be articulated and/or expanded into a number of different configurations. In FIGS. 14A-14E the implant 10 is shown in a fully collapsed and linear orientation, which is configured to be inserted into the body of a patient, for example, through a cannula. In FIGS. 15A-15E, the first lateral leg 12 is articulated relative to the link plates 16 joining the first lateral leg 12 to the second lateral leg 14. For example, the first lateral leg 12 is hinged at an angle about pins 32 and link plates 16 and second lateral leg 14 remain in a linear orientation along longitudinal axis A. In FIGS. 16A-16E, the first and second lateral legs 12, 14 are both articulated. For example, the first lateral leg 12 is hinged at a first angle relative to the link plates 16 and the second lateral leg 14 is hinged at a second angle relative to the link plates 16. The first and second angles may be the same or different. In this widened orientation, the implant 10 has a large footprint configured to maximize contact with the vertebral bodies. In FIGS. 17A-17E, the lateral legs 12, 14 are shown expanded in parallel, which thereby provides for the link plates 34, 36 expanded in parallel as well. In FIGS. 18A-18E, the lateral legs 12, 14 are non-uniformly expanded relative to one another. By expanding one lateral leg 12, 14 more or less than the other, coronal adjustments may be made to the spine. In FIGS. 19A-19E, both of the lateral legs 12, 14 are shown uniformly expanded with greater anterior heights and the attached link plates 34, 36 are passively expanded in parallel.

Figure 20:
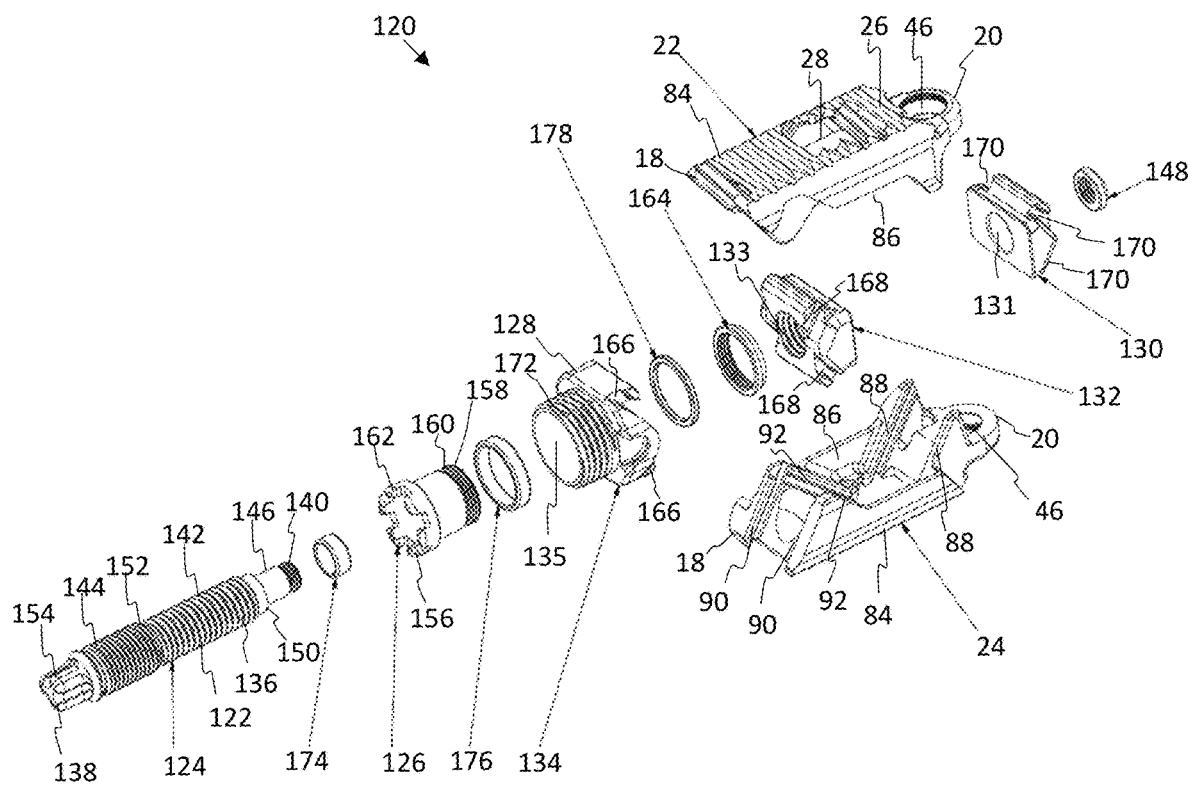
FIG. 20 is an exploded view of one of the expandable lateral legs according to another embodiment.
Figure 21A:
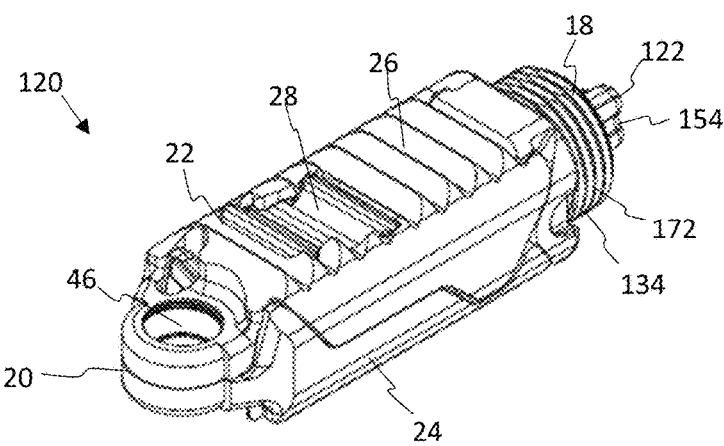
FIGS. 21A-21H show perspective, rear, side, front, top, and cross-sectional views of the lateral leg of FIG. 21 in a fully collapsed position.
Figure 21B:
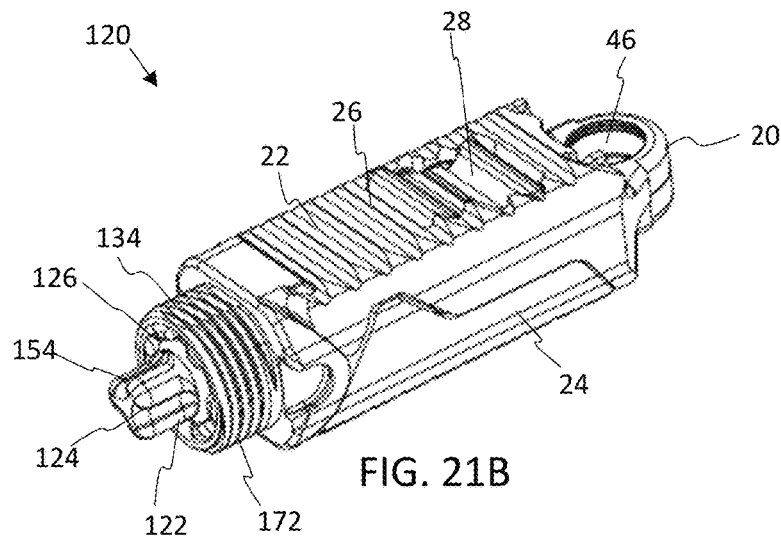
Figure 21C:
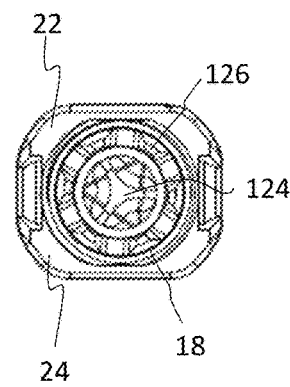
Figure 21D:
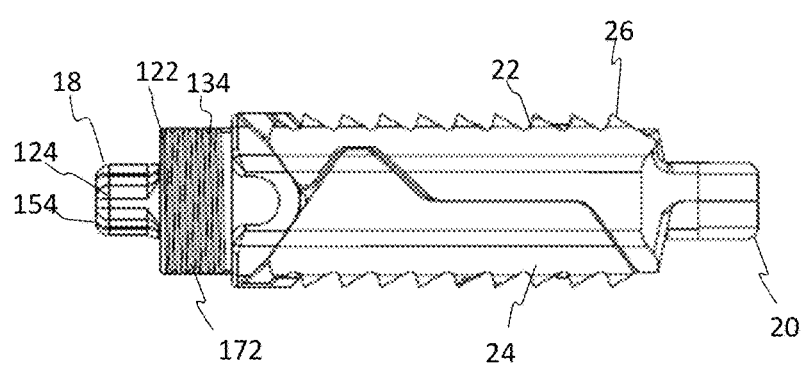
Figure 21E:
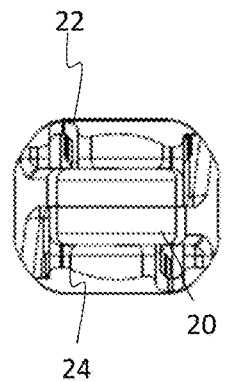
Figure 21F:
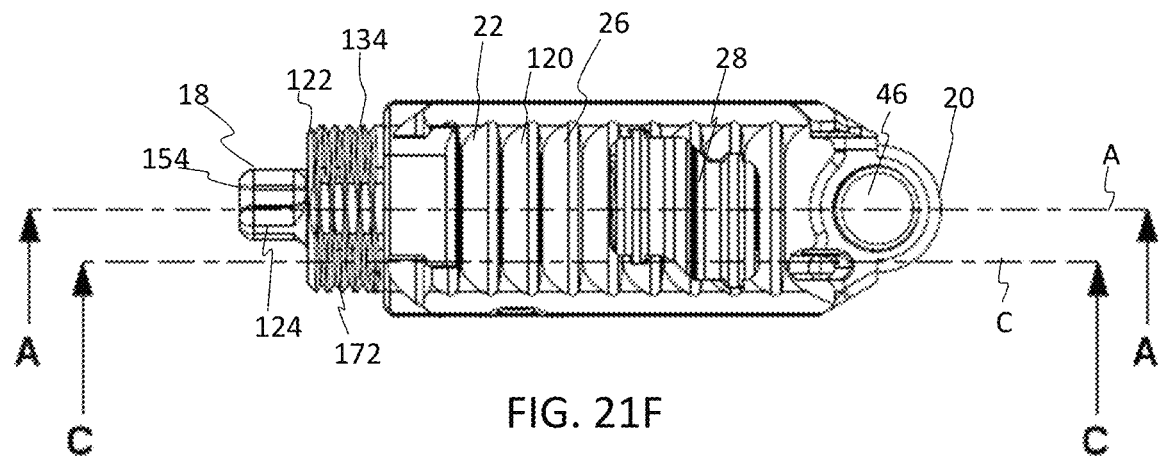
Figure 21G:
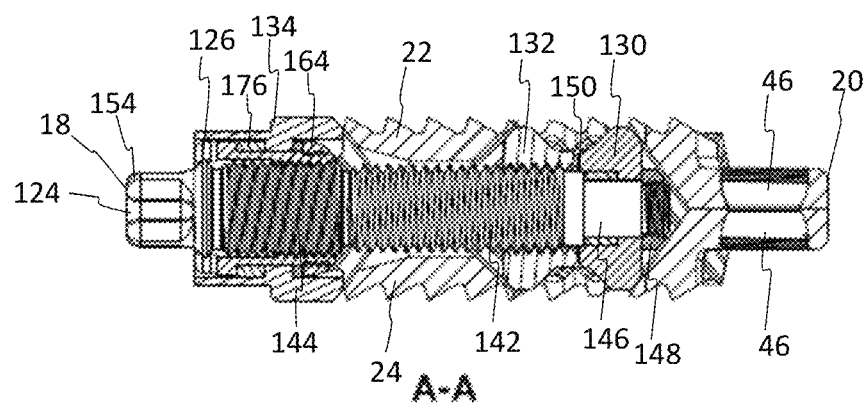
Figure 21H:
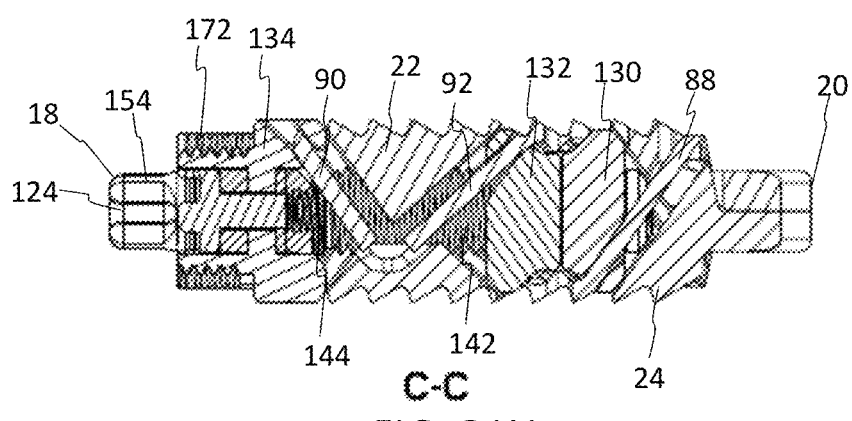

Turning now to FIG. 20, another embodiment of an expandable lateral leg 120 is shown. Lateral leg 120 is similar to lateral legs 12, 14, 112 except an alternative actuation assembly 122 is provided. The upper and lower endplates 22, 24 are the same or similar to the endplates described herein except the endplates 22, 24 include a single central graft window 28. The lateral leg 120 includes an actuation assembly 122 with an actuator 124 and a nut 126 configured to move a plurality of internal ramps 128, which expand the endplate 22, 24 in height. The plurality of ramps 128 may include a plurality of driving ramps including a front ramp 130, a mid-ramp 132, and a rear ramp 134. The front ramp 130 may include a central longitudinal bore 131, the mid-ramp 132 may include a central longitudinal bore 133, and the rear ramp 134 may include a central longitudinal bore 135. The plurality of driving ramps 130, 132, 134 may be positioned along the length of the actuator 124 and are configured to engage and drive the upper and lower endplates 22, 24, respectively. When one or more of the driving ramps 130, 132, 134 are moved and slide against the upper and lower endplates 22, 24, the lateral leg 120 expands in height. The expansion may include the ability to individually adjust the anterior and/or posterior heights of the lateral legs 120.

The actuation assembly 122 is configured to expand the height of the respective lateral legs 120. The actuation assembly 122 includes rotatable drive screw or actuator 124 and rotatable drive nut 126 configured to move a plurality of internal ramps 128. Each lateral leg 120 includes at least three driving ramps: front ramp 130, mid-ramp 132, and rear ramp 134, which interface with the actuator 124. The actuator 124 may include a shaft 136 extending from a proximal end 138 to a distal end 140. The shaft 136 includes a first threaded portion 142, a second threaded portion 144, and a non-threaded portion 146. The first threaded portion 142 may be positioned between the non-threaded portion 146 and the second threaded portion 144. The first and second threaded portions 142, 144 may have the same or different attributes including outer diameters, handedness, thread form, thread angle, lead, pitch, etc.

Figure 22A:
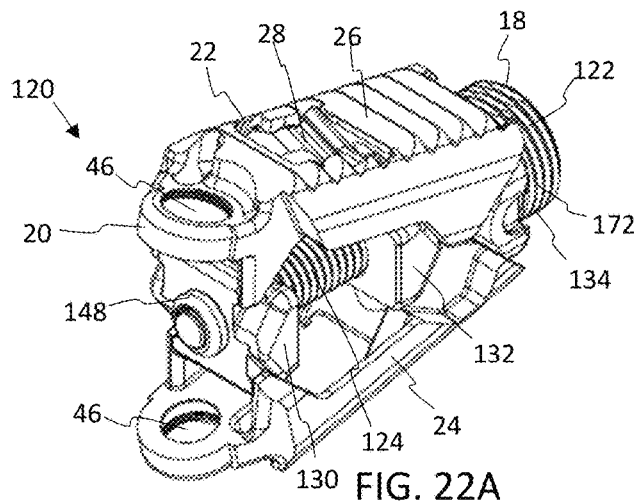
FIGS. 22A-22H show perspective, rear, side, front, top, and cross-sectional views of the lateral leg of FIG. 21 in one expanded position.
Figure 22B:
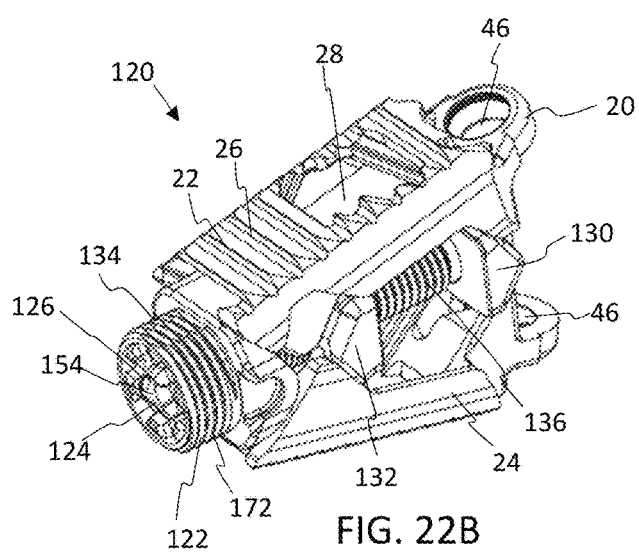
Figure 22C:
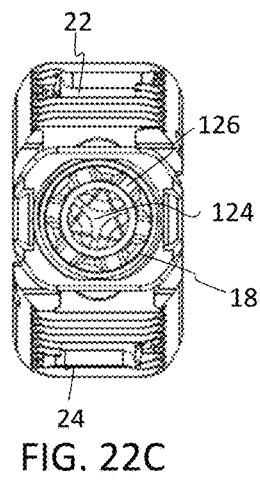
Figure 22D:
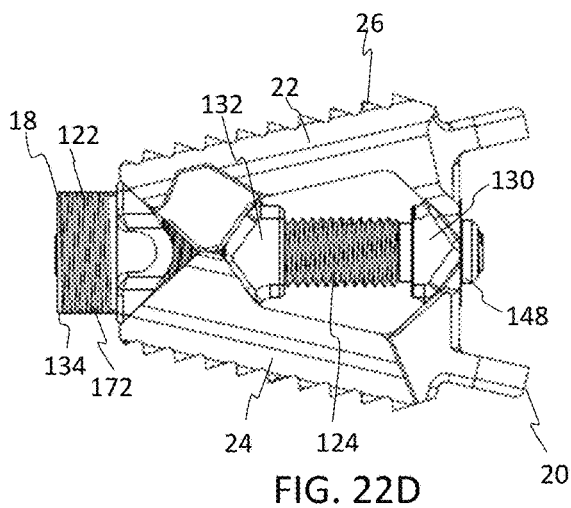
Figure 22E:
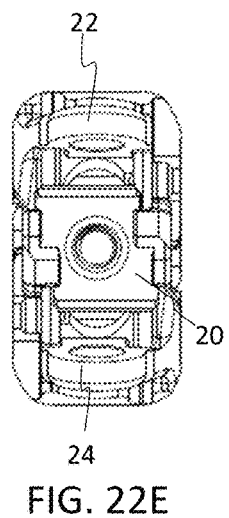
Figure 22F:
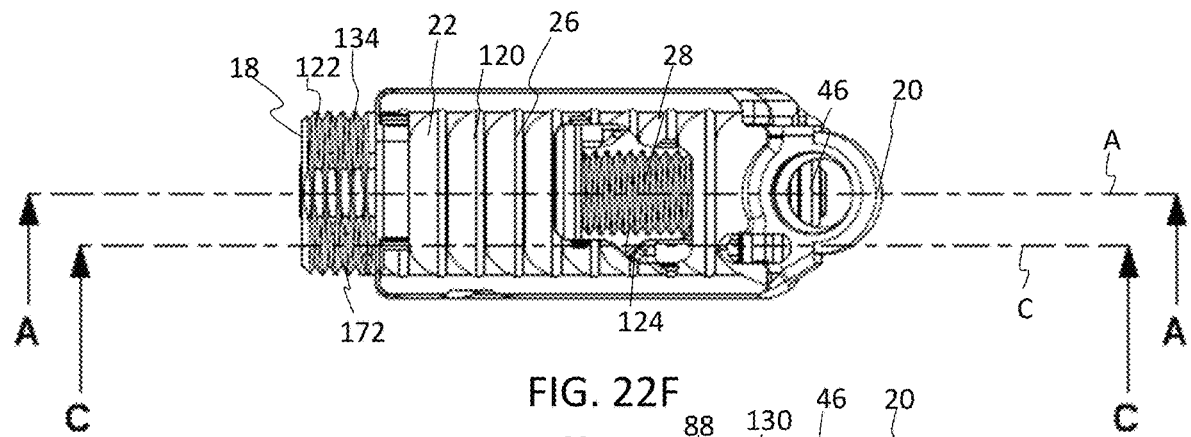
Figure 22G:
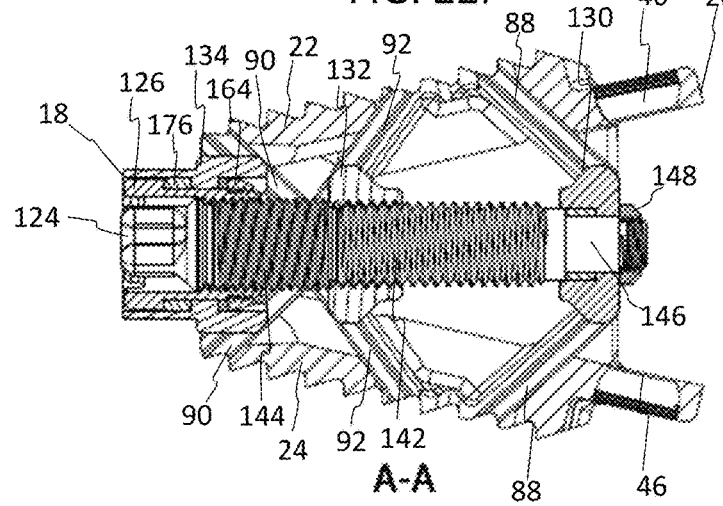
Figure 22H:
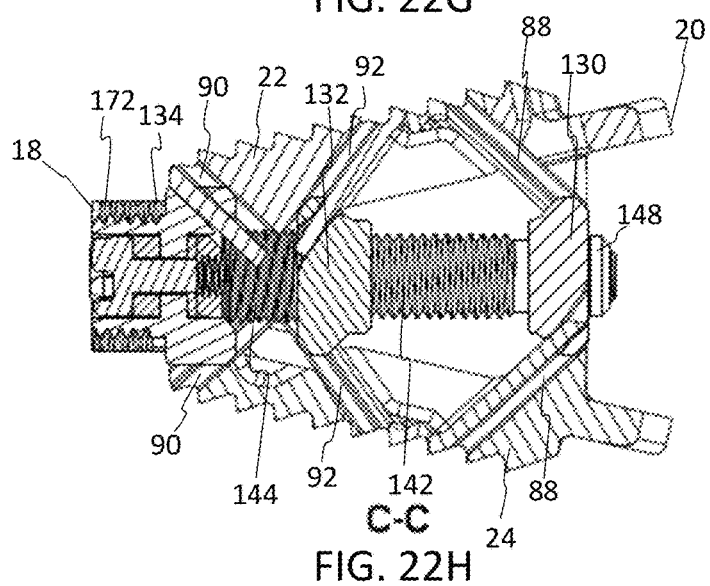
Figure 23A:
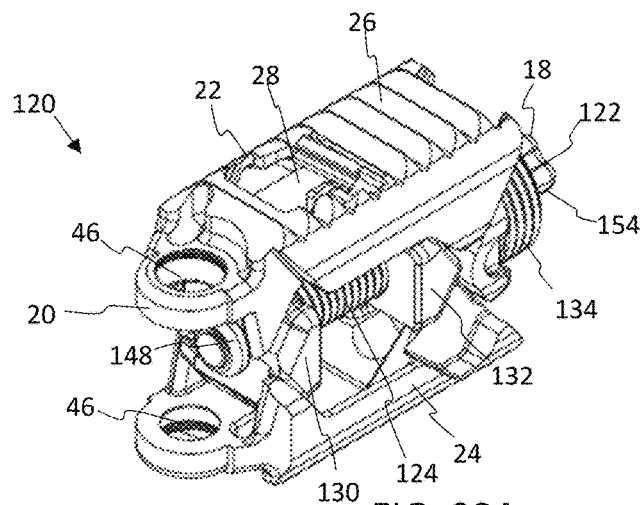
FIGS. 23A-23H show perspective, rear, side, front, top, and cross-sectional views of the lateral leg of FIG. 21 with the endplates expanded in parallel.
Figure 23B:
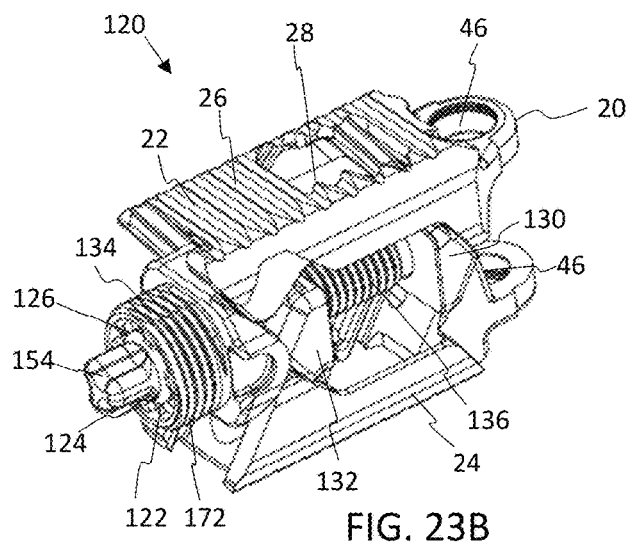
Figure 23C:
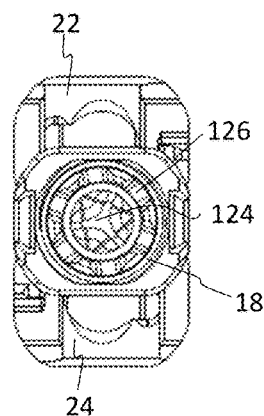
Figure 23D:
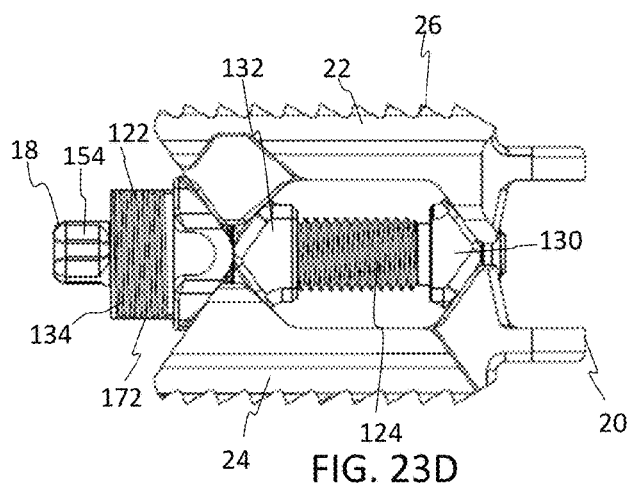
Figure 23E:
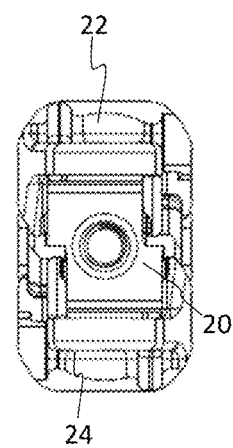
Figure 23F:
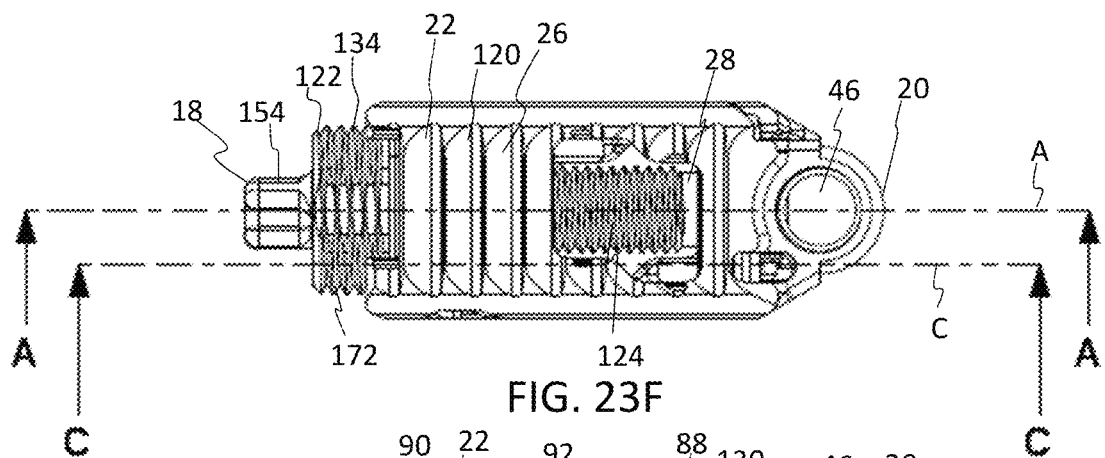
Figure 23G:
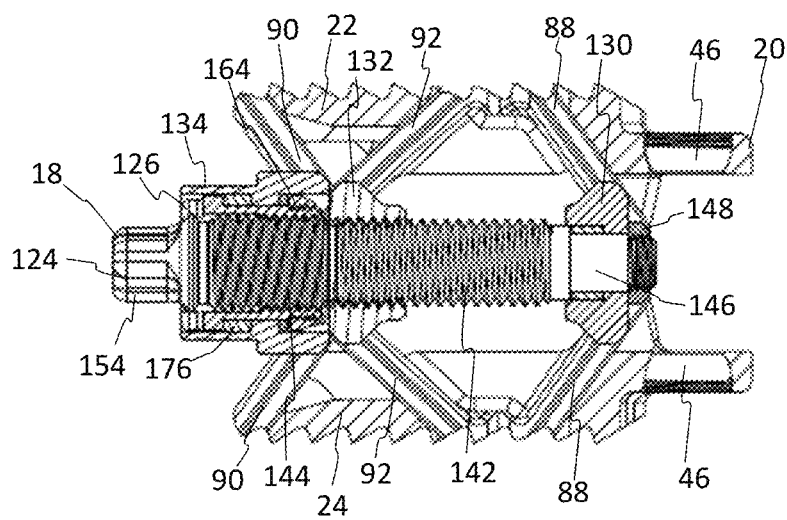
Figure 23H:
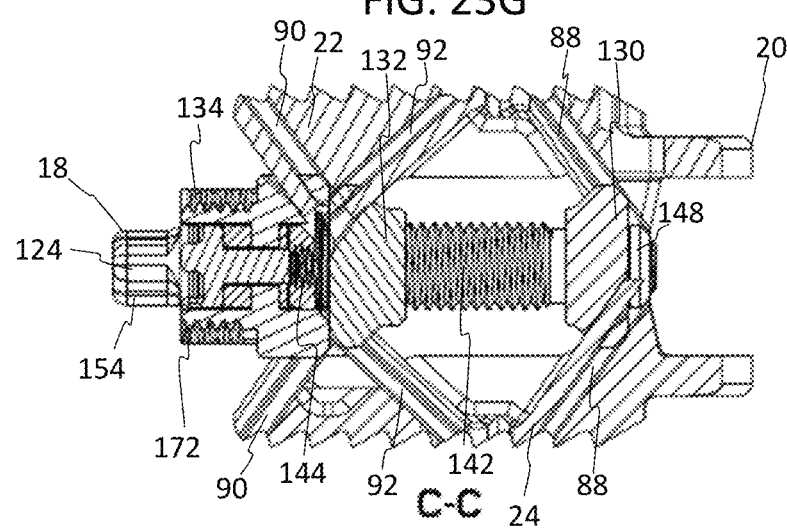
Figure 24A:
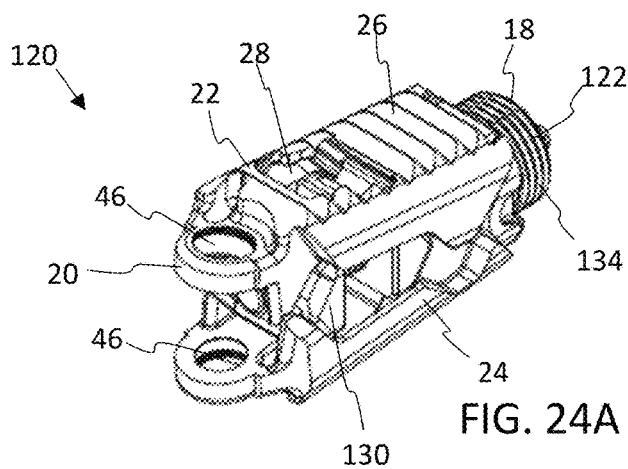
FIGS. 24A-24H show perspective, rear, side, front, top, and cross-sectional views of the lateral leg of FIG. 21 in another expanded position.
Figure 24B:
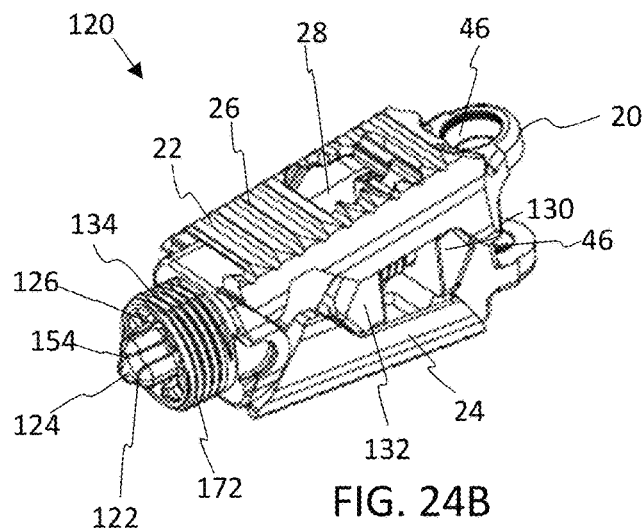
Figure 24C:
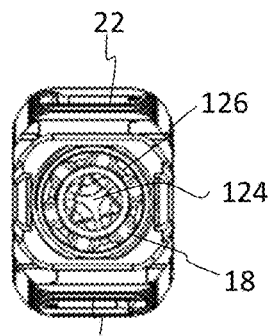
Figure 24D:
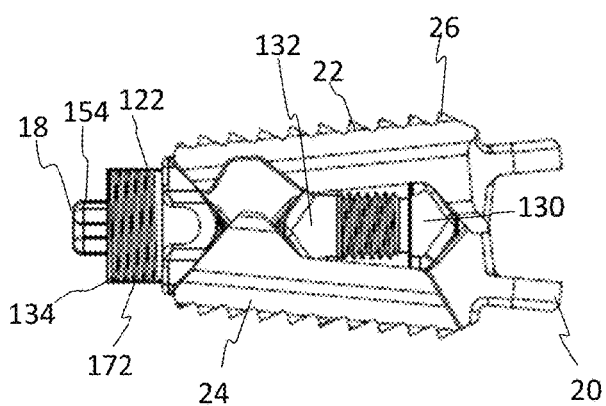
Figure 24E:
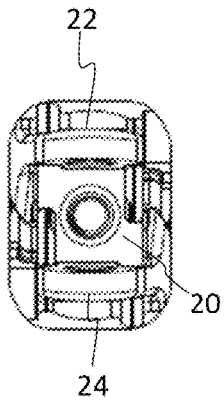
Figure 24F:
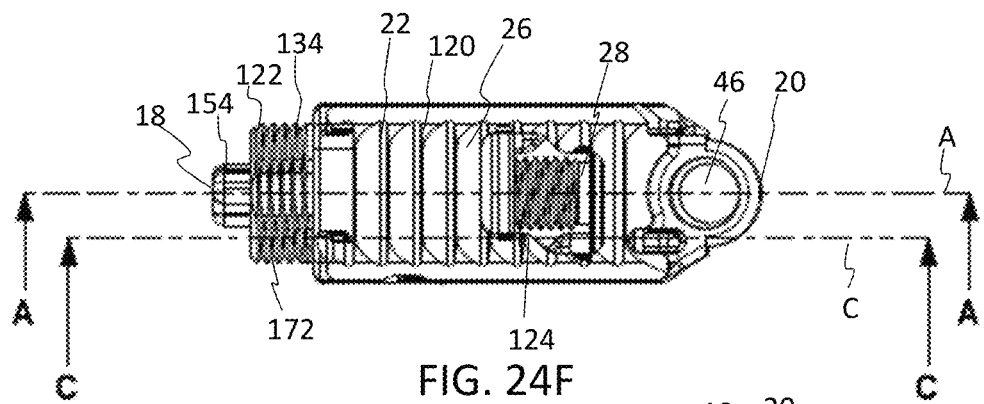
Figure 24G:
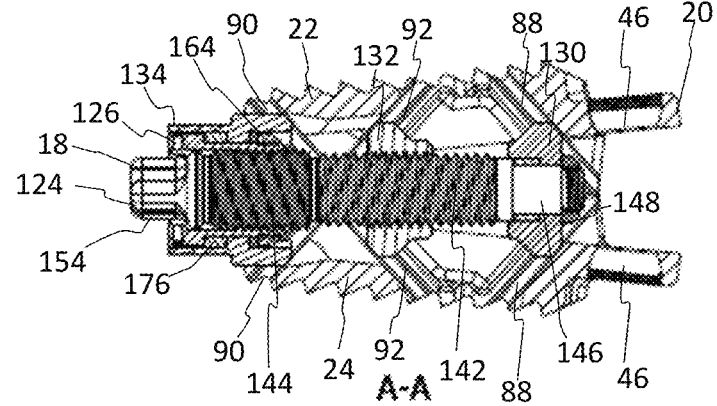
Figure 24H:
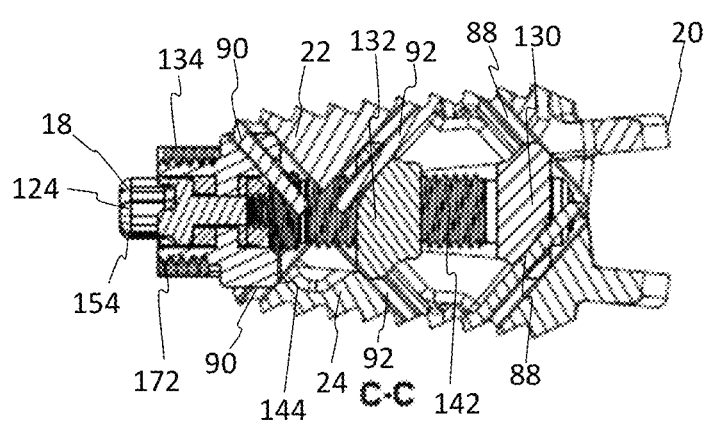
Figures 25A, 25B:
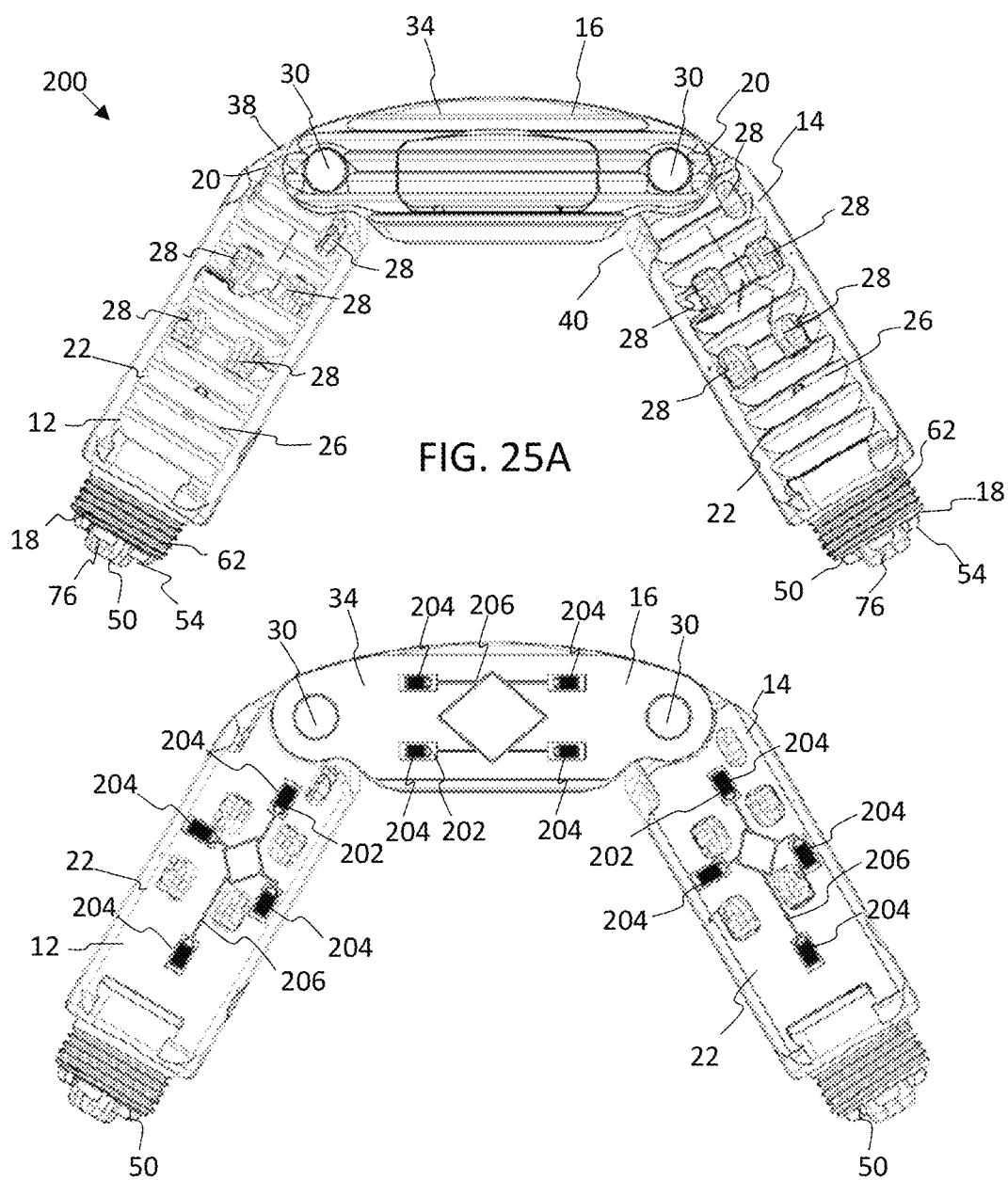
FIGS. 25A-25D show top, partial cross-sectional, and perspective views of an embodiment of the implant having one or more strain gauges configured to measure the forces acting on the endplates and/or the link plates.
Figure 25C:
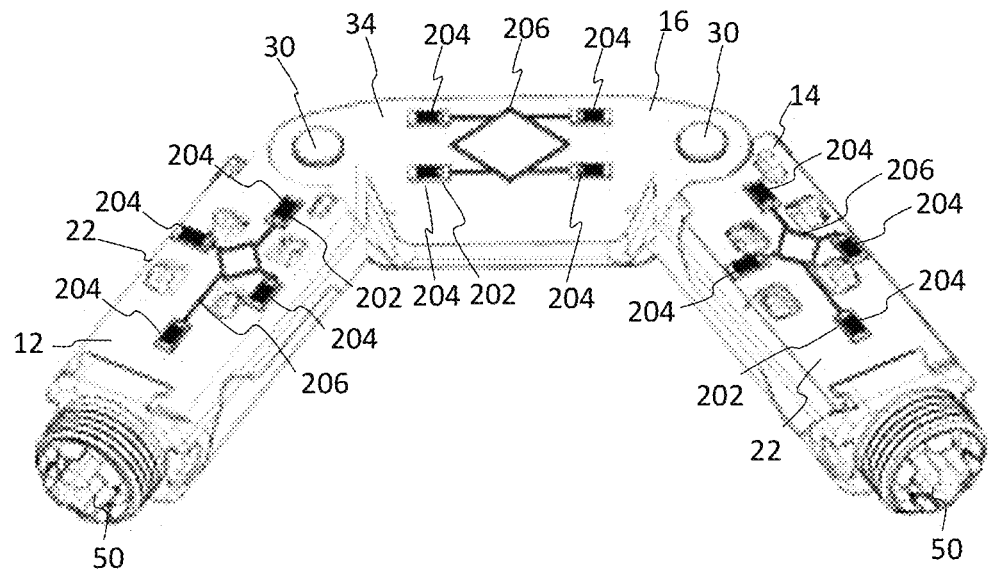
Figure 25D:
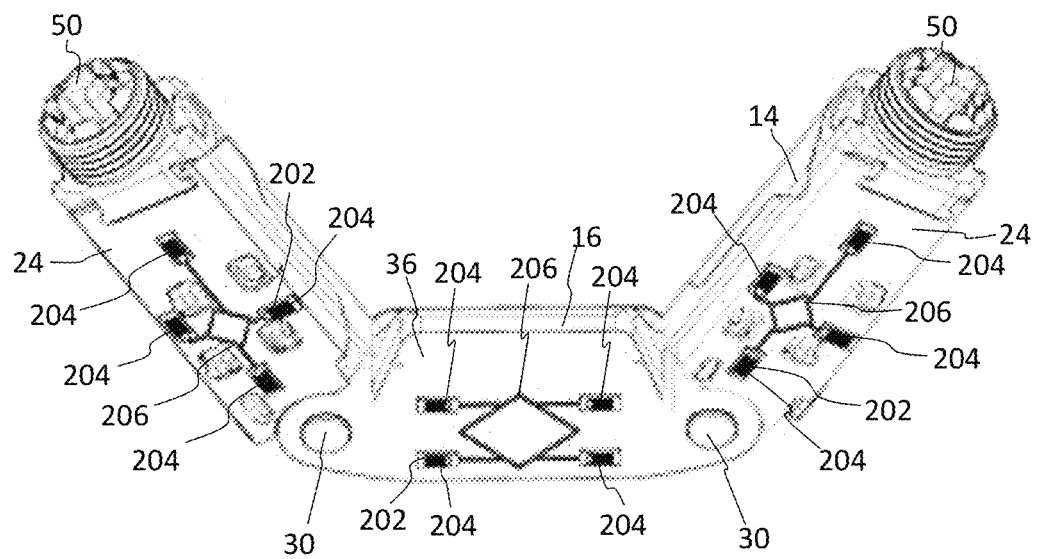

In FIGS. 21A-21H, the lateral leg 120 is shown in a fully collapsed configuration. In FIGS. 22A-22H, the lateral leg 120 is shown expanded in height with a greater anterior height. In FIGS. 23A-23H, the lateral leg 120 is shown expanded with the endplates 22, 24 generally in parallel. In FIGS. 24A-24H, the lateral leg 120 is shown expanded to a lesser degree with an increased anterior height. As best seen in FIG. 22G, the front driving ramp 130 includes a non-threaded bore 131, which is positioned on the non-threaded portion 146 of the actuator 124. The front driving ramp 130 may be located between internally threaded locking cap 148 and a shoulder 150 defined between the first threaded portion 142 and the non-threaded portion 146. In this manner, the front ramp 130 is secured to the actuator shaft 136.

The mid-ramp 132 includes a threaded bore 133, which is positioned on the first threaded portion 142 and is moveable along the length of the first threaded portion 142 in order to move the mid-ramp 132 and thereby move the upper and lower endplates 22, 24 to expand the lateral leg 120. The rear ramp 134 is engaged with the nut 126, which is positioned along the second threaded portion 144 in order to move the rear ramp 134. The rear ramp 134 is moveable along the length of the second threaded portion 144 to move the upper and lower endplates 22, 24 and expand the lateral leg 120. The first threaded portion 142 may have a smaller outer diameter and different handedness than the second threaded portion 144. The first threaded portion 142 may transition to the second threaded portion 144 at a second shoulder 152.

The proximal end 138 of the actuator shaft 136 may include a first instrument retention feature, such as a ribbed neck 154. The ribbed neck 154 may include knurled neck grips or other suitable engagement surfaces, which are configured to interface with a driver instrument to thereby rotate the actuator shaft 136.

The actuation assembly 122 may also include rotatable drive nut 126. The rotatable nut 126 may be configured to move the rear ramp 134 independent of the mid-ramp 132 and front ramp 130. The nut 126 may extend from a proximal end 156 to a distal end 158. The distal end 158 may include an outer threaded portion 160 configured to mate with a threaded cap or internally threaded ring 164. In an alternative embodiment, the threaded portion 160 may be configured to mate with a corresponding internal threaded portion in the bore 135 through the rear driving ramp 134. The proximal end 156 may include a second instrument retention feature, such as a slotted head 162. The slotted head 162 may include slots or other suitable engagement surfaces configured to interface with a driver instrument to thereby rotate the nut 126. When only the nut 126 is rotated clockwise, the rear ramp 134 may be translated forward, decreasing it's distance to the front ramp such that posterior height increases and the anterior height decreases. When the nut 126 remains stationary and only the actuator 124 is rotated clockwise, increasing the gap between the rear ramp 62 and the front ramp 58 increases the lordotic angle of the spacer When both the actuator 124 and the nut 126 are rotated clockwise at the same time, the rear ramp 134 and mid-ramp 132 may slide together, thereby moving the endplates 22, 24 in parallel. It will be appreciated that the movement of the driving ramps 130, 132, 134 and resulting expansion may be operated by the actuator 124 and/or nut 126 with any suitable configurations and mechanisms.

The driving ramps 130, 132, 134 may include one or more ramped surfaces 166, 168, 170. The ramped surfaces 166, 168, 170 of the driving ramps 130, 132, 134 may be configured and dimensioned to engage the corresponding ramped surfaces 88, 90, 92 of the upper and lower endplates 22, 24, respectively. For example, the rear ramp 134 may include one or more ramped surfaces 166, mid-ramp 132 may include one or more ramped surfaces 168, and front ramp 130 may include one or more ramped surfaces 170. The ramped surfaces 166, 168, 170 may be angled continuous surfaces with a given angle of slope. It is contemplated that the slope of the ramped surfaces 166, 168, 170 may be equal or can differ from each other. The ramped surfaces 166, 168, 170 may be generally straight ramped surfaces or may be curved ramped surfaces. The ramped surfaces 166, 168, 170 may include female slide ramps or recessed ramps configured to receive the male ramped surfaces 88, 90, 92 of the endplates 22, 24. It will be appreciated that the male and female ramps may be reversed or may be otherwise configured to provide for slidable mating between the ramps.

The second ramped surface 90 of the endplate 22, 24 may be configured to slidably interface with the ramped surface 166 of the rear ramp 134. The first ramped surface 88 of the endplate 22, 24 may be configured to slidably interface with the ramped surface 170 of the front ramp 130. The third ramped surface 92 of the endplate 22, 24 may be configured to slidably interface with the ramped surface 168 of the driving mid-ramp 132. As one or more of the driving ramps 130, 132, 134 moves, the ramped surface or surfaces 166, 168, 170 pushes against the corresponding ramped surface or surfaces 88, 90, 92 of the upper and lower endplates 22, 24, respectively. In this manner, the individual driving ramps 130, 132, 134 control the rate of expansion of the upper and lower endplates 22, 24, which thereby controls the expansion of the anterior, posterior, and central heights of upper and lower endplates 22, 24. Accordingly, movement of the driving ramps 130, 132, 134, causes the upper and lower endplate 22, 24 to be pushed outwardly into the expanded configurations.

The lateral leg 120 may further include one or more of the following features. The rear ramp 134 may include an outer threaded portion 172 at the proximal end which may be configured to be retained by an insertion instrument. One or more friction rings or washers 174, 176, 178 may be provided to provide drag or thrust resistance to one or more of the moveable components in the assembly 122. The friction rings 174, 176, 178 may include PEEK washers or may be composed of another suitable material. For example, friction ring 174 may be provided to apply resistance to the drive screw 124. Friction ring 176 may be provided to apply resistance to the drive nut 126. A thrust washer 178 may be provided to apply resistance to the rear driving ramp 134.

In order to improve the access profile of the interbody implant 10 while maximizing cortical bone contact surface area, methods and systems of installing, articulating and/or expanding the implant may include one or more of the following. The implant may enter the disc space with a linear configuration and articulate to increase surface area contact on the anterior apophyseal ring. The orientation and position of the interbody implant in its final implanted position may be optimized by pre-/intra-op scans and/or normal population statistics that determine bone mineral density maps of the vertebral body. Robotic and/or navigation guidance may be used to correctly orient the interbody. Further details of robotic and/or navigational systems can be found in U.S. Patent Publication No. 2017/0239007, which is incorporated herein by reference in its entirety for all purposes.

In one embodiment, the implant may be implanted with one or more of the following steps: (1) A determination may be made on final optimal implant location to optimize bone mineral density of the contacted bone/implant interface. (2) Robotic and/or navigation may be used to determine the potential trajectories that will allow for this optimal implant location to be achieved. (3) A cannula may be docked on the disc space through Kambin's triangle, or the anatomical area that is bordered by the disc space, exiting nerve root, and traversing nerve root. (4) The expandable interbody may be inserted in a linear, non-expanded orientation. (5) The expandable interbody is actuated into the widened U-shaped footprint that fully maximizes surface contact area with the vertebral body. (6) The lateral legs of the expandable interbody are then expanded. If necessary, an additional portal may be used on the contralateral side of the disc space to provide an additional window through which to attach a driver and expand the opposite lateral leg. The expansion in height may be provided to precisely restore normal spinal alignment and evenly distribute the load across the vertebral endplates.

The expandable fusion devices described herein may be manufactured from a number of biocompatible materials including, but not limited to, titanium, stainless steel, titanium alloys, non-titanium metallic alloys, polymeric materials, plastics, plastic composites, PEEK, ceramic, and elastic materials.

The features of the embodiments described herein may provide one or more of the following advantages. A small insertion profile, such as an 8 mm insertion width into the disc space, may reduce the required skin, fascia, muscle, and/or ligamentous disruption. A controlled lordosis may be provided through placement of the interbody around the lateral anterior edges of the vertebral body and independent control of the anterior and posterior aspects of the cage. The large footprint and implant placement may serve to reduce the concerns of subsidence as well as increase the stability profile of the implant. The implant may have full independent control for adjustment of sagittal and coronal balance. It will be appreciated that different or additional advantages may also be achieved based on the disclosure herein.

Turning now to FIGS. 25A-27D, an embodiment of an implant 200 including one or more strain gauges 202 is shown. Implant 200 is similar to implant 10 described herein with the addition of the strain gauges 202 in the endplates 22, 24 and/or link plates 16. By adding one or more strain gauges 202, the implant 200 may measure the force, pressure, tension, and/or weight distribution across the surface area of the endplates 22, 24 and/or link plates 16. This may reduce the probability of subsidence and/or allow for precise placement of the implant 200 to provide a stable construct between interbody and bone.

In order to enhance precision placement of the implant 200 with equal distribution of force across the endplates 22, 24 and/or link plates 34, 36, one or more strain gauges 202 with one or more differential motion sensors 204 may be affixed to the endplates 22, 24 and/or link plates 34, 36. One or more sensors 204 may be distributed across the upper and lower endplates 22, 24 and/or upper and lower link plates 34, 36. The strain gauges 202 may be distributed across the implant 200 in order to provide the ability to measure differential pressures across the implant 200.

The strain gauge 202 may include a plurality of sensors 204 and a circuitry 206 connecting the sensors 204. The strain gauges 202 may include, for example, a thin strip of metal designed to measure mechanical load by changing resistance when stressed. The strain gauge 202 may be embedded in or affixed to the material of the endplates 22, 24 and/or link plates 34, 36. The strain gauge 202 may be recessed into or placed near the outer surfaces of the endplates 22, 24 and/or link plates 34, 36. In one embodiment, the strain gauge 202 is embedded within a 3D printed material. For example, the strain gauge 202 may be embedded within a 3D printed titanium material forming the endplates 22, 24 and/or link plates 34, 36. The gauges 202 and sensors 204 may be embedded within the foundation of the 3D printed endplates 22, 24 and/or link plates 34, 36, thereby providing complete integration between the material contacting the vertebral body and the sensors 204 registering the strain on that endplate 22, 24 and/or link plate 34, 36.

Figure 26A:
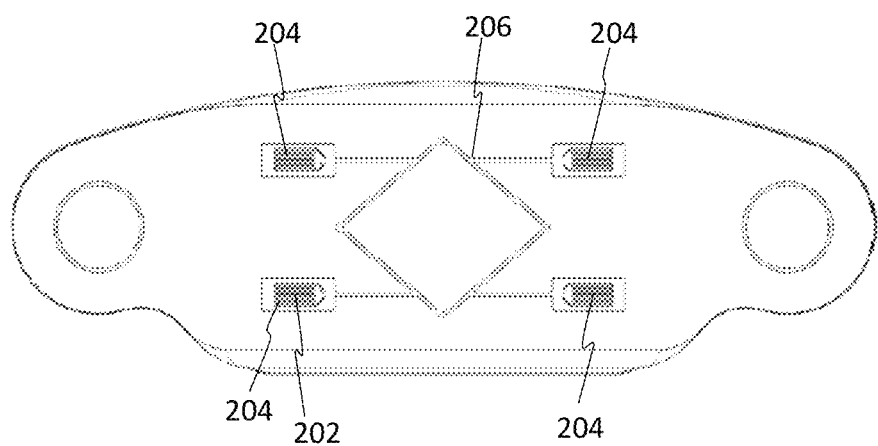
FIGS. 26A-26C show alternative arrangements for the strain gauges and circuitry configurations.
Figure 26B:
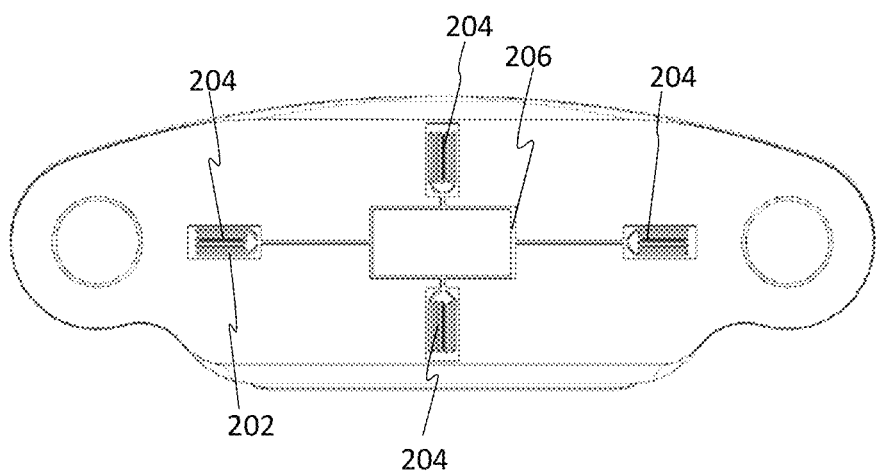
Figure 26C:
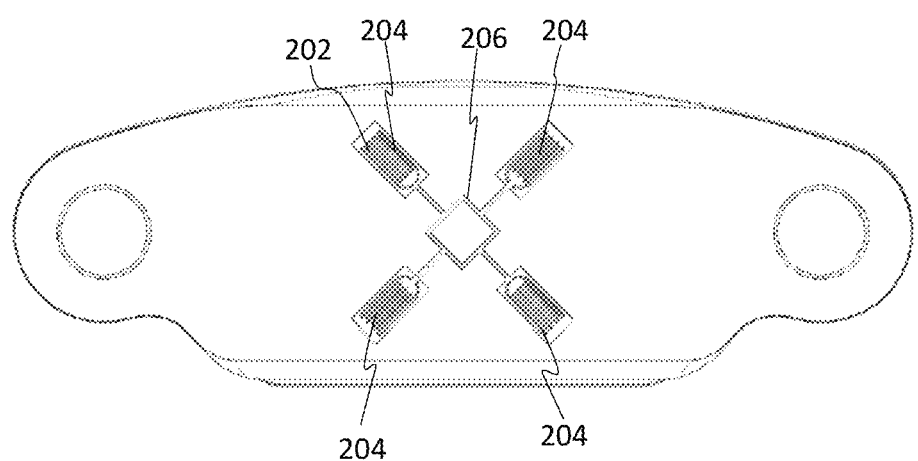
Figure 27A:
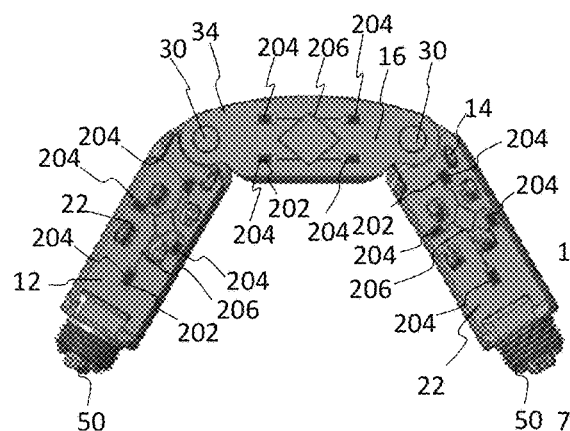
FIGS. 27A-27D show an embodiment of the implant with various strain gauges embedded in the endplates and link plates.
Figure 27B:
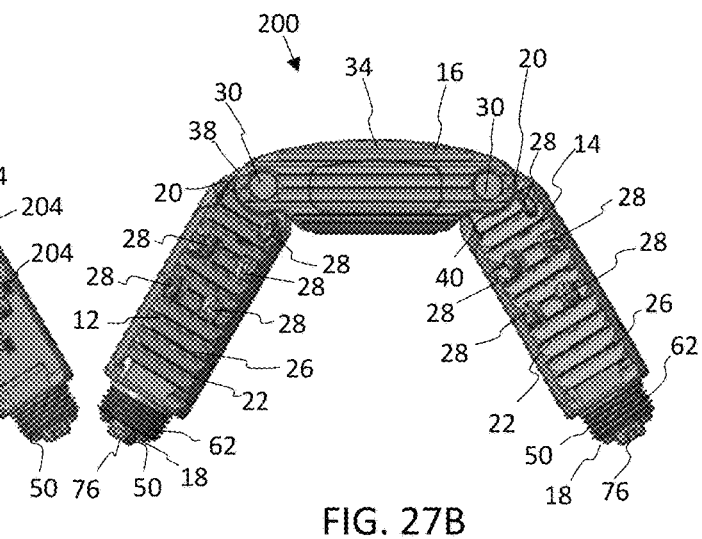
Figure 27C:
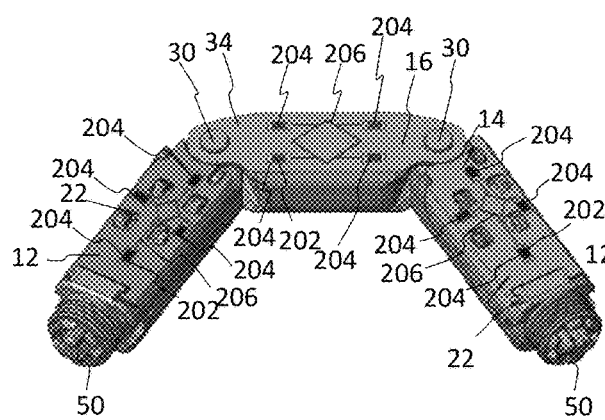
Figure 27D:
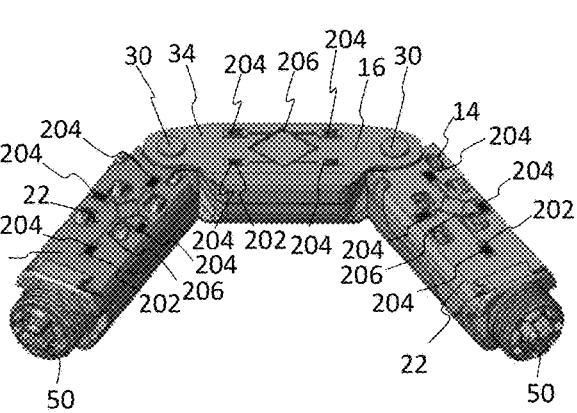

As shown in FIGS. 26A-26C, alternative arrangements for the strain gauges 202 are shown. The strain gauge resistance changes may be measured in a bridge circuit 206 to allow for precise measurement of small resistance changes. The circuit 206 may include a full-bridge, half-bridge, or quarter-bridge circuit. In the embodiments shown, the circuit 206 is a full-bridge configuration, which may be more sensitive to resistance changes. The gauge 202 may include four sensors 204 connected to legs of the circuit 206. In FIG. 26A, a first pair of sensors 204 are aligned and a second pair of sensors 204 are aligned such that the first and second pairs of sensors 204 are arranged in parallel. In FIG. 26B, a first pair of sensors 204 are aligned and a second pair of sensors 204 are aligned such that the sensors 204 are arranged in perpendicular. In FIG. 26C, the full-bridge system has four strain gauge sensors 204 with an X-type configuration with each sensor 204 connected to the four legs of the bridge circuit 206.

As shown in FIGS. 27A-27D, a first type of strain gauge 202 may be provided on lateral legs 12, 14 and a second type of strain gauge 202 may be provided on link plates 16. The positions of the sensors 204 may be identified through different circuitries 206 designed to measure the forces acting on the endplates 22, 24 and/or link plates 34, 36 throughout the surface area of the implant 200. The expansion of the implant 200 in its final implanted position may be optimized with the strain gauges 202 to measure the forces registering contact with both the superior and inferior vertebral bodies.

The features of the embodiments described herein may provide one or more of the following advantages. The integrated 3D printed endplates with embedded sensors 204 may allow for endplates 22, 24 and/or link plates 34, 36 to be printed with embedded sensors 204 in a one step process. The strain gauges 202 may help to improve surgeon understanding of the forces that are acting on the interbody placement. The ability to measure forces acting on the implant 200 may allow for measurements in the change in electrical resistance to create an understanding of the external forces acting on the implant 200. Increased endplate-to-bone contact may result of the measurement capabilities to increase the equal distribution of contact with the vertebral body across the surface area of the implant 200.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

What is claimed is:

1. An expandable implant comprising:
    a first lateral leg and a second lateral legs, each of the first lateral leg and the second lateral leg including:
        upper and lower endplates configured to engage adjacent vertebrae;
        an actuator assembly including a rotatable actuator having a shaft and a rotatable nut; and
        a plurality of driving ramps including a front ramp, a mid-ramp, and a rear ramp positioned along the shaft of the actuator, wherein the upper and lower endplates are engaged with the plurality of driving ramps, and wherein rotation of the actuator and/or the nut causes movement of one or more of the driving ramps, thereby causing an expansion in height of the upper and lower endplates; and
    at least one link plate including a first link plate and a second link plate, wherein the first link plate is pivotably connected to the upper endplates of the first and second lateral legs, and the second link plate is pivotably connected to the lower endplates of the first and second lateral legs.

2. The expandable implant of claim 1, wherein the first and second lateral legs and the at least one link plate are positionable along a central longitudinal axis of the implant, thereby forming a linear orientation configured to be inserted through a cannula.

3. The expandable implant of claim 1, wherein the first and second lateral legs are pivotable about a respective first and second hinge, thereby allowing for a widened U-shaped configuration of the implant.

4. The expandable implant of claim 1, wherein the first and second link plates passively expand when either or both of the first and second lateral legs are expanded.

5. The expandable implant of claim 1, wherein the rotatable nut is configured to move the rear ramp independent of the mid-ramp and the front ramp.

6. The expandable implant of claim 1, wherein the shaft of the actuator includes a first threaded portion, a second threaded portion, and a third threaded portion, and wherein the front ramp is positioned on the first threaded portion, the mid-ramp is positioned on the second threaded portion, and the rear ramp is positioned on the third threaded portion of the actuator.

7. The expandable implant of claim 1, wherein the shaft of the actuator includes a first threaded portion, a second threaded portion, and a non-threaded portion, and wherein the front ramp is positioned on the non-threaded portion of the actuator, the mid-ramp is positioned on the first threaded portion, and the rear ramp is positioned on the second threaded portion.

8. The expandable implant of claim 7, wherein the first threaded portion has a smaller outer diameter and different handedness than the second threaded portion.

9. An expandable implant comprising:
    upper and lower link plates each extending from a first end to a second end; and
    first and second lateral legs, each including:
        upper and lower endplates configured to engage adjacent vertebrae;
        an actuator assembly including a rotatable actuator having a shaft and a rotatable nut;
        a plurality of driving ramps including a front ramp, a mid-ramp, and a rear ramp positioned along the shaft of the actuator, wherein the upper and lower endplates are engaged with the plurality of driving ramps, and wherein rotation of the actuator and/or the nut causes movement of one or more of the driving ramps, thereby causing an expansion in height of the upper and lower endplates; and
    wherein the upper link plate is pivotably coupled to the first lateral leg at the first end of the upper link plate and is pivotably coupled to the second lateral leg at the second end of the upper link plate, and the lower link plate is pivotably coupled to the first lateral leg at the first end of the lower link plate and is pivotably coupled to the second lateral leg at the second end of the lower link plate, and
    wherein the upper and lower link plates passively expand when either or both of the first and second lateral legs are expanded.

10. The expandable implant of claim 9, wherein the first and second lateral legs and upper and lower link plates are positionable along a central longitudinal axis of the implant, thereby forming a linear orientation configured to be inserted through a cannula.

11. The expandable implant of claim 9, wherein the first and second lateral legs are pivotable, thereby allowing for a widened U-shaped configuration of the implant.

12. The expandable implant of claim 9, wherein the rotatable nut is configured to move the rear ramp independent of the mid-ramp and the front ramp.

13. The expandable implant of claim 9, wherein the shaft of the actuator includes a first threaded portion, a second threaded portion, and a third threaded portion, and wherein the front ramp is positioned on the first threaded portion, the mid-ramp is positioned on the second threaded portion, and the rear ramp is positioned on the third threaded portion of the actuator.

14. The expandable implant of claim 9, wherein the shaft of the actuator includes a first threaded portion, a second threaded portion, and a non-threaded portion, and wherein the front ramp is positioned on the non-threaded portion of the actuator, the mid-ramp is positioned on the first threaded portion, and the rear ramp is positioned on the second threaded portion.

* * * * *